United States Patent
Liu et al.

(10) Patent No.: US 11,319,341 B2
(45) Date of Patent: *May 3, 2022

(54) IMMUNE-STIMULATING SOLUBLE DOXORUBICIN-CONJUGATED COMPLEX

(71) Applicant: Yafei (Shanghai) Biopharmaceutical Co., Ltd., Shanghai (CN)

(72) Inventors: Cheng Liu, Shanghai (CN); Yuan Liu, Shanghai (CN)

(73) Assignee: Yafei (Shanghai) Biopharmaceutical Co., Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/796,436

(22) Filed: Feb. 20, 2020

(65) Prior Publication Data

US 2020/0247842 A1  Aug. 6, 2020

Related U.S. Application Data

(63) Continuation-in-part of application No. 15/991,150, filed on May 29, 2018, now abandoned, which is a
(Continued)

(51) Int. Cl.
*A61K 38/00* (2006.01)
*C07K 1/107* (2006.01)
(Continued)

(52) U.S. Cl.
CPC .......... *C07K 1/1077* (2013.01); *A61K 31/704* (2013.01); *A61K 47/542* (2017.08);
(Continued)

(58) Field of Classification Search
None
See application file for complete search history.

(56) References Cited

U.S. PATENT DOCUMENTS

| | | | |
|---|---|---|---|
| 6,291,638 B1 * | 9/2001 | Fiume .................. | A61K 47/645 530/324 |
| 2009/0175873 A1 * | 7/2009 | Liu ..................... | C07K 5/06026 424/139.1 |
| 2016/0144050 A1 * | 5/2016 | Kim ...................... | A61K 38/14 514/1.3 |

* cited by examiner

*Primary Examiner* — Jeanette M Lieb
(74) *Attorney, Agent, or Firm* — Lewis Kohn & Walker LLP; David M. Kohn; Kari Moyer-Henry

(57) ABSTRACT

Doxorubicin derivatives for targeted activation by Legumain, its preparation method and use. The doxorubicin derivatives are obtained by condensation between the amino group of compound A and the carboxyl group of compound B and have the following structure:

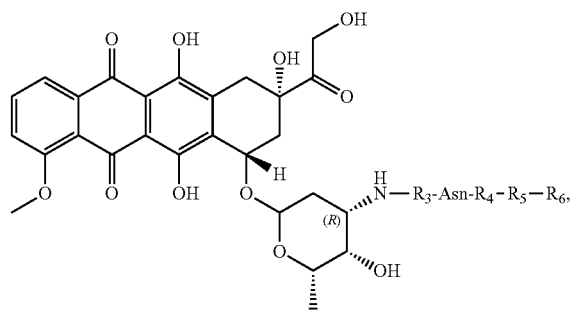

compounds A and B have the following structures, respectively:

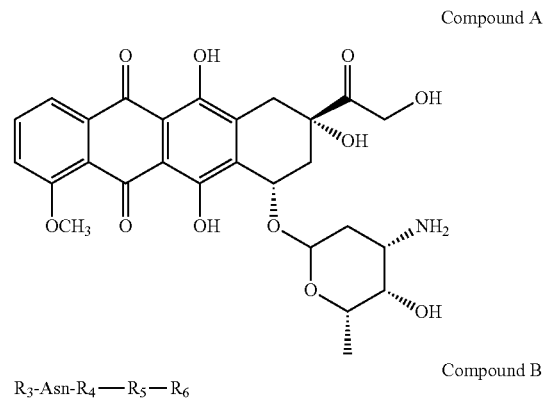

Compound A

Compound B $R_3$-Asn-$R_4$—$R_5$—$R_6$ wherein $R_3$ in compound B is Leu or absent; $R_4$ is any one amino acid selected from the group consisting of Ala and Thr; $R_5$ is any one amino acid selected from the group consisting of Ala, Thr and Asn; $R_6$ is

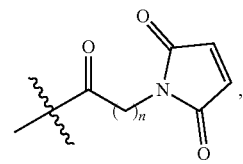

wherein n=1-20; or

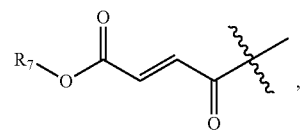

wherein $R_7$ is substituted or unsubstituted, linear or branched, saturated or unsaturated C1-C20 fatty hydrocarbon, or substituted or unsubstituted C6-C20 aromatic hydrocarbon. The doxorubicin derivatives of the present invention
(Continued)

are specifically tumor-targeted and have a long in vivo metabolic half-life, as compared with doxorubicin. They exhibit an efficient and safe anti-tumor effect and could be used to prepare an anti-tumor drug.

7 Claims, 2 Drawing Sheets

Related U.S. Application Data continuation of application No. 14/655,869, filed on Dec. 21, 2016, now Pat. No. 9,982,011.

(51) Int. Cl.
*C07K 5/103* (2006.01)
*C07H 15/26* (2006.01)
*C07H 15/252* (2006.01)
*A61K 47/65* (2017.01)
*A61K 47/54* (2017.01)
*A61K 31/704* (2006.01)

(52) U.S. Cl.
CPC ............ *A61K 47/545* (2017.08); *A61K 47/65* (2017.08); *C07H 15/252* (2013.01); *C07H 15/26* (2013.01); *C07K 5/101* (2013.01); *C07K 5/1008* (2013.01)

IMMUNE-STIMULATING SOLUBLE DOXORUBICIN-CONJUGATED COMPLEX

RELATED APPLICATIONS

This application is a continuation-in-part of U.S. patent application Ser. No. 15/991,150 filed May 29, 2018, which is a continuation of U.S. patent application Ser. No. 14/655,869 filed Dec. 12, 2016, now U.S. Pat. No. 9,982,011, which claims priority under 35 U.S.C. 371 from International Patent Application No. PCT/CN13/001620 filed on Dec. 23, 2013, which claims priority from Chinese patent application No. 2012 1 0573744.3 filed on Dec. 26, 2012, the contents of which are hereby incorporated by reference herein.

TECHNICAL FIELD

The present invention relates to an anti-tumor drug compound, in particular, to the preparation and use of an immune-stimulating soluble doxorubicin-conjugated complex.

TECHNICAL BACKGROUND

We have previously published the invention. Aspartame targets the activated doxorubicin derivative (Patent No. 201210573744.3). EMC-AANL-DOX binds albumin through the EMC group to form a large coupling in the blood. Molecules that specifically recognize activated compounds in tumors through aspartase. Based on this patent, through further compound screening and systematic biological research, we have developed immunosuppressive cell targeting and soluble doxorubicin-conjugated complexes. New compounds with curative effect.

SUMMARY OF INVENTION

The technical problem to be solved by the present invention is to overcome the above-mentioned shortcomings, and research and design an immune-stimulating soluble doxorubicin-conjugated complex. Due to the combination of appropriate compound linker, the toxicity of cytotoxic drugs is reduced, and targeted aggregation in the tumor microenvironment can stimulate the immune system and activate efficiently.
The present disclosure provides a compound having the following structure or a pharmaceutically acceptable salt thereof:
In one or more embodiments, the compound can be prepared by the following methods, but is not limited to these preparation methods, including the following steps:
Step 1: Preparation of tripeptide-PABC or tetrapeptide: coupling amino acid residues and isolating the formed tripeptide-PABC or tetrapeptide, that is, C-A;
Step 2: Preparation of MI-S: selecting a compound suitable for the MI-S group of this patent, and performing condensation or cyclization to obtain MI-S with a carboxyl group at one end;
Step 3: Preparation of MI-S-C-A: Intermediate (MI-S-C-A) obtained by coupling C-A obtained in step 1 and MI-S obtained in step 2 with amino and carboxyl groups;
Step 4. Covalently combine the carboxyl or hydroxyl activation product of the A-terminus of the compound MI-S-C-A obtained in step 3 with the amino group of the optional drug to form Immune-stimulating Soluble doxorubicin-conjugated complexes.

The present invention also provides a pharmaceutical composition comprising a compound of Formula I or a pharmaceutically acceptable salt thereof disclosed herein, and a pharmaceutically acceptable carrier.

In one or more embodiments, the cancer is selected from the group consisting of: liver cancer, kidney cancer, thyroid cancer, colorectal cancer, bladder cancer, brain cancer, breast cancer, cervical cancer, rectal cancer, esophageal cancer, lung cancer (e.g., bronchial lung cancer, Including undifferentiated small cell and non-small cell), nasopharyngeal cancer, pancreatic cancer, prostate cancer, skin cancer, gastric cancer, uterine cancer, ovarian cancer, testicular cancer, blood cancer (such as chronic or acute leukemia, including lymphocytic And granulocytic leukemia), malignant lymphoma, fibrosarcoma, soft tissue sarcoma, osteosarcoma, rhabdomyosarcoma, Ewing's sarcoma, nephroblastoma, neuroblastoma, thyroid cancer and squamous cell carcinoma of the head and neck.

The invention also provides the use of the compound of formula I or a pharmaceutically acceptable salt thereof in the preparation of an immunotherapeutic medicament.

In one or more embodiments, the immunotherapeutics can be used to stimulate the proliferation of T cells and invasion of lesions, inhibit tumor-associated macrophages, and/or promote stimulation of immune responses.

The experimental design idea of the present invention is to first synthesize a large number of compounds with different structures, and then use these compounds to study the working mechanism of the asparagine peptide endonuclease. Since the active center of the asparaginide endonuclease is located at the bottom of the balloon-like indentation, the substrate peptide needs to be close to the enzyme active center at the bottom of the balloon to be activated. At this time, the molecular structure connecting the adjacent end of the substrate peptide directly determines its activation efficiency. Based on this, we screened different C groups and found that the asparagine peptide endonuclease preferably recognizes the ALA-ALA-ASN sequence and cleaves the ASN amide bond, and at the same time the amino acids on both sides of the ALA-ALA-ASN sequence Residues or groups have a great influence on the binding force of the compound to the enzyme protein, that is, the screening of A, MI-S, we linked different synthetic A and MI-S groups to doxorubicin and then screened for activation efficiency under the conditions of tumor tissue or asparagine endonuclease. In the end, a Doxorubicin conjugates complex QHL-087 with reduced toxicity of Doxorubicin and increased solubility, targeted aggregation of tumor sites, and significantly enhanced activation characteristics was obtained.

Through experimental screening and determination, the added functional groups do not affect drug release and improve activation efficiency. Therefore, compared with the previous generation of doxorubicin derivative, the immuno-stimulant soluble doxorubicin derivative increases anti-tumor effect.

It was found through experimental measurement that: 1. Doxorubicin-conjugated complex of the present invention can aggregate in the tumor micro-environment 2. the Doxorubicin-conjugated complex of the present invention has increased water solubility 3. the MI-S group in the Doxorubicin-conjugated complex of the present invention the effect of the difference on activation efficiency is very large. The longer the chain length of MI-S, the steric relationship is not conducive to the combination of the compound and the enzyme, and the activation efficiency is reduced. The chain length of MI-S is too short or all are alkanes. When the base chain is used, the binding ability to A is insufficient, and the solubility of the compound cannot be improved.

Thus, the compound of the present invention has the characteristics of water solubility, long half-life, and high activation. Compared with doxorubicin, epirubicin, and comparative patented invention, the compound of the present invention reduces the toxicity of the compound and improves the anti-tumor effect. Curative effect, more dosage forms can be prepared at the same time, and it has very good application prospects.

EMBODIMENTS

Figure 1:
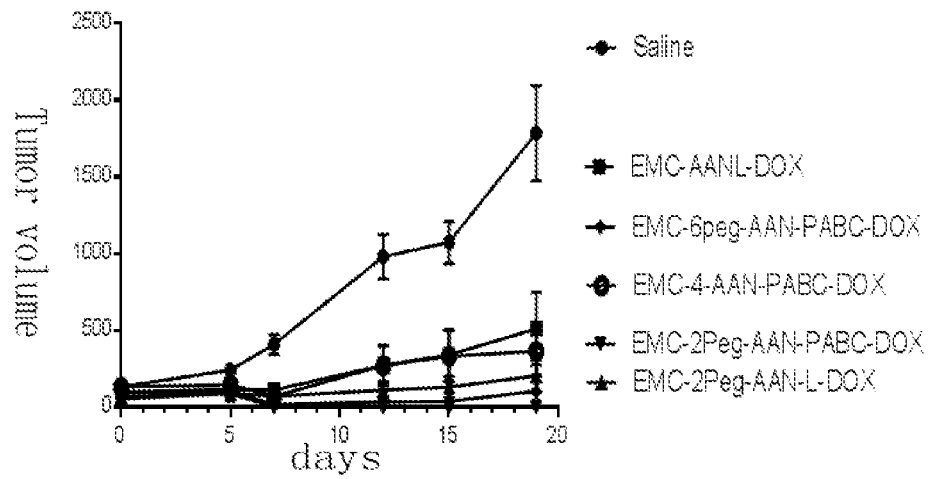
FIG. 1: The efficacy of drugs in HT1080 tumor.

The technical solution of the present invention is further described below in combination with specific embodiments
When MI is monomaleimido, C is preferably AAN, and D is doxorubicin, the compound table is as follows:

| Compound number | S1 | S2 | S3 | A |
|---|---|---|---|---|
| QHL-001 | / | 2peg | / | PABC-NH$_2$ |
| QHL-002 | / | 3peg | / | PABC-NH$_2$ |
| QHL-003 | / | 4peg | / | PABC-NH$_2$ |
| QHL-004 | / | 6peg | / | PABC-NH$_2$ |
| QHL-005 | / | 2peg | / | PABC-OH |
| QHL-006 | / | 3peg | / | PABC-OH |
| QHL-007 | / | 4peg | / | PABC-OH |
| QHL-008 | / | 6peg | / | PABC-OH |
| QHL-009 | / | 2peg | / | Leu |
| QHL-010 | / | 3peg | / | Leu |
| QHL-011 | / | 4peg | / | Leu |
| QHL-012 | / | 6peg | / | Leu |
| QHL-013 | / | 2peg | Glu | PABC-NH$_2$ |
| QHL-014 | / | 3peg | Glu | PABC-NH$_2$ |
| QHL-015 | / | 4peg | Glu | PABC-NH$_2$ |
| QHL-016 | / | 6peg | Glu | PABC-NH$_2$ |
| QHL-017 | / | 2peg | Glu | PABC-OH |
| QHL-018 | / | 3peg | Glu | PABC-OH |
| QHL-019 | / | 4peg | Glu | PABC-OH |
| QHL-020 | / | 6peg | Glu | PABC-OH |
| QHL-021 | / | 2peg | Glu | Leu |
| QHL-022 | / | 3peg | Glu | Leu |
| QHL-023 | / | 4peg | Glu | Leu |
| QHL-024 | / | 6peg | Glu | Leu |
| QHL-025 | / | 2peg | ASP | PABC-NH$_2$ |
| QHL-026 | / | 3peg | ASP | PABC-NH$_2$ |
| QHL-027 | / | 4peg | ASP | PABC-NH$_2$ |
| QHL-028 | / | 6peg | ASP | PABC-NH$_2$ |
| QHL-029 | / | 2peg | ASP | PABC-OH |
| QHL-030 | / | 3peg | ASP | PABC-OH |
| QHL-031 | / | 4peg | ASP | PABC-OH |
| QHL-032 | / | 6peg | ASP | PABC-OH |
| QHL-033 | / | 2peg | ASP | Leu |
| QHL-034 | / | 3peg | ASP | Leu |
| QHL-035 | / | 4peg | ASP | Leu |
| QHL-036 | / | 6peg | ASP | Leu |
| QHL-037 | C$_2$—COOH | 2peg | Glu | PABC-NH$_2$ |
| QHL-038 | C$_2$—COOH | 2peg | Glu | PABC-OH |
| QHL-039 | C$_2$—COOH | 2peg | Glu | Leu |
| QHL-040 | C$_2$—COOH | 2peg | ASP | PABC-NH$_2$ |
| QHL-041 | C$_2$—COOH | 2peg | ASP | PABC-OH |
| QHL-042 | C$_2$—COOH | 2peg | ASP | Leu |
| QHL-043 | C$_2$—COOH | 3peg | Glu | PABC-NH$_2$ |
| QHL-044 | C$_2$—COOH | 3peg | Glu | PABC-OH |
| QHL-045 | C$_2$—COOH | 3peg | Glu | Leu |
| QHL-046 | C$_2$—COOH | 3peg | ASP | PABC-NH$_2$ |
| QHL-047 | C$_2$—COOH | 3peg | ASP | PABC-OH |
| QHL-048 | C$_2$—COOH | 3peg | ASP | Leu |
| QHL-049 | C$_2$—COOH | 4peg | Glu | PABC-NH$_2$ |
| QHL-050 | C$_2$—COOH | 4peg | Glu | PABC-OH |
| QHL-051 | C$_2$—COOH | 4peg | Glu | Leu |
| QHL-052 | C$_2$—COOH | 4peg | ASP | PABC-NH$_2$ |
| QHL-053 | C$_2$—COOH | 4peg | ASP | PABC-OH |
| QHL-054 | C$_2$—COOH | 4peg | ASP | Leu |
| QHL-055 | C$_2$—COOH | 6peg | Glu | PABC-NH$_2$ |
| QHL-056 | C$_2$—COOH | 6peg | Glu | PABC-OH |
| QHL-057 | C$_2$—COOH | 6peg | Glu | Leu |
| QHL-058 | C$_2$—COOH | 6peg | ASP | PABC-NH$_2$ |
| QHL-059 | C$_2$—COOH | 6peg | ASP | PABC-OH |
| QHL-060 | C$_2$—COOH | 6peg | ASP | Leu |
| QHL-061 | C$_3$—COOH | 2peg | Glu | PABC-NH$_2$ |
| QHL-062 | C$_3$—COOH | 2peg | Glu | PABC-OH |
| QHL-063 | C$_3$—COOH | 2peg | Glu | Leu |
| QHL-064 | C$_3$—COOH | 2peg | ASP | PABC-NH$_2$ |
| QHL-065 | C$_3$—COOH | 2peg | ASP | PABC-OH |
| QHL-066 | C$_3$—COOH | 2peg | ASP | Leu |
| QHL-067 | C$_3$—COOH | 3peg | Glu | PABC-NH$_2$ |
| QHL-068 | C$_3$—COOH | 3peg | Glu | PABC-OH |
| QHL-069 | C$_3$—COOH | 3peg | Glu | Leu |
| QHL-070 | C$_3$—COOH | 3peg | ASP | PABC-NH$_2$ |
| QHL-071 | C$_3$—COOH | 3peg | ASP | PABC-OH |
| QHL-072 | C$_3$—COOH | 3peg | ASP | Leu |
| QHL-073 | C$_3$—COOH | 4peg | Glu | PABC-NH$_2$ |
| QHL-074 | C$_3$—COOH | 4peg | Glu | PABC-OH |
| QHL-075 | C$_3$—COOH | 4peg | Glu | Leu |
| QHL-076 | C$_3$—COOH | 4peg | ASP | PABC-NH$_2$ |
| QHL-077 | C$_3$—COOH | 4peg | ASP | PABC-OH |
| QHL-078 | C$_3$—COOH | 4peg | ASP | Leu |
| QHL-079 | C$_3$—COOH | 6peg | Glu | PABC-NH$_2$ |
| QHL-080 | C$_3$—COOH | 6peg | Glu | PABC-OH |
| QHL-081 | C$_3$—COOH | 6peg | Glu | Leu |
| QHL-082 | C$_3$—COOH | 6peg | ASP | PABC-NH$_2$ |
| QHL-083 | C$_3$—COOH | 6peg | ASP | PABC-OH |
| QHL-084 | C$_3$—COOH | 6peg | ASP | Leu |
| QHL-085 | C$_2$—COOH | 2peg | / | PABC-NH$_2$ |
| QHL-086 | C$_2$—COOH | 2peg | / | PABC-OH |
| QHL-087 | C$_2$—COOH | 2peg | / | Leu |
| QHL-088 | C$_2$—COOH | 3peg | / | PABC-NH$_2$ |
| QHL-089 | C$_2$—COOH | 3peg | / | PABC-OH |
| QHL-090 | C$_2$—COOH | 3peg | / | Leu |
| QHL-091 | C$_2$—COOH | 4peg | / | PABC-NH$_2$ |
| QHL-092 | C$_2$—COOH | 4peg | / | PABC-OH |
| QHL-093 | C$_2$—COOH | 4peg | / | Leu |
| QHL-094 | C$_2$—COOH | 6peg | / | PABC-NH$_2$ |
| QHL-095 | C$_2$—COOH | 6peg | / | PABC-OH |
| QHL-096 | C$_2$—COOH | 6peg | / | Leu |
| QHL-097 | C$_3$—COOH | 2peg | / | PABC-NH$_2$ |
| QHL-098 | C$_3$—COOH | 2peg | / | PABC-OH |
| QHL-099 | C$_3$—COOH | 2peg | / | Leu |
| QHL-100 | C$_3$—COOH | 3peg | / | PABC-NH$_2$ |
| QHL-101 | C$_3$—COOH | 3peg | / | PABC-OH |
| QHL-102 | C$_3$—COOH | 3peg | / | Leu |
| QHL-103 | C$_3$—COOH | 4peg | / | PABC-NH$_2$ |
| QHL-104 | C$_3$—COOH | 4peg | / | PABC-OH |
| QHL-105 | C$_3$—COOH | 4peg | / | Leu |
| QHL-106 | C$_3$—COOH | 6peg | / | PABC-NH$_2$ |
| QHL-107 | C$_3$—COOH | 6peg | / | PABC-OH |
| QHL-108 | C$_3$—COOH | 6peg | / | Leu |
| QHL-109 | C$_3$—COOH | / | Glu | PABC-NH$_2$ |
| QHL-110 | C$_3$—COOH | / | Glu | PABC-OH |
| QHL-111 | C$_3$—COOH | / | Glu | Leu |
| QHL-112 | C$_3$—COOH | / | ASP | PABC-NH$_2$ |
| QHL-113 | C$_3$—COOH | / | ASP | PABC-OH |
| QHL-114 | C$_3$—COOH | / | ASP | Leu |
| QHL-115 | C$_6$—COOH | / | Glu | PABC-NH$_2$ |
| QHL-116 | C$_6$—COOH | / | Glu | PABC-OH |
| QHL-117 | C$_6$—COOH | / | Glu | Leu |

-continued

| Compound number | S1 | S2 | S3 | A |
|---|---|---|---|---|
| QHL-118 | C$_6$—COOH | / | ASP | PABC-NH$_2$ |
| QHL-119 | C$_6$—COOH | / | ASP | PABC-OH |
| QHL-120 | C$_6$—COOH | / | ASP | Leu |
| QHL-121 | C$_6$—COOH | / | Gly | Leu |
| QHL-122 | C$_6$—COOH | / | Ala | Leu |
| QHL-123 | C$_6$—COOH | / | Val | Leu |
| QHL-124 | C$_6$—COOH | / | Leu | Leu |
| QHL-125 | C$_6$—COOH | / | Ile | Leu |
| QHL-126 | C$_6$—COOH | / | Met | Leu |
| QHL-127 | C$_6$—COOH | / | Phe | Leu |
| QHL-128 | C$_6$—COOH | / | Trp | Leu |
| QHL-129 | C$_6$—COOH | / | Ser | Leu |
| QHL-130 | C$_6$—COOH | / | Thr | Leu |
| QHL-131 | C$_6$—COOH | / | Cys | Leu |
| QHL-132 | C$_6$—COOH | / | Tyr | Leu |
| QHL-133 | C$_6$—COOH | / | Asn | Leu |
| QHL-134 | C$_6$—COOH | / | Gln | Leu |
| QHL-135 | C$_6$—COOH | / | Lys | Leu |
| QHL-136 | C$_6$—COOH | / | Arq | Leu |
| QHL-137 | C$_6$—COOH | / | His | Leu |

When A is PABC-OH, the synthetic route is as follows:

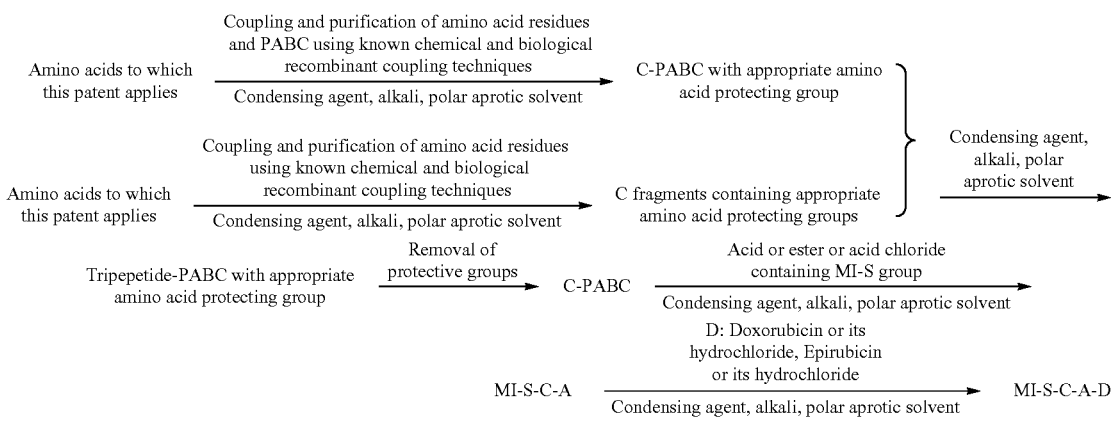

Examples of the base used in the production method include, for example, an organic base such as triethylamine, pyridine, N, N-diisopropylethylamine, 4-dimethylaminopyridine, 1,2,2,6,6-Pentamethylpiperidine, etc., or inorganic bases, such as sodium carbonate, potassium carbonate, sodium bicarbonate and potassium bicarbonate. Examples of the condensing agent used in the preparation method include, for example, HBTU, DMC, HATU, HOBT, DIC, DCC, EDCI, DEPBT, etc. The solvent used in the preparation method may be any solvent, as long as the solvent itself is inert in the reaction and does not inhibit the reaction. Such solvents include halogenated hydrocarbon solvents such as dichloromethane and chloroform, aromatic hydrocarbon solvents such as benzene and toluene, and aprotic solvents such as acetonitrile, N, N-dimethylformamide, and dimethyl. Sulfoxide, etc., ester solvents, such as methyl acetate and ethyl acetate, etc., ether solvents, such as tetrahydrofuran, or a mixture of these solvents. The reaction in this preparation method can be performed in a temperature range from 150° C. to ice cooling.

Example 1 Synthesis of QHL-095

As shown in the figure below, taking QHL-095 as an example, the specific synthesis process is as follows:

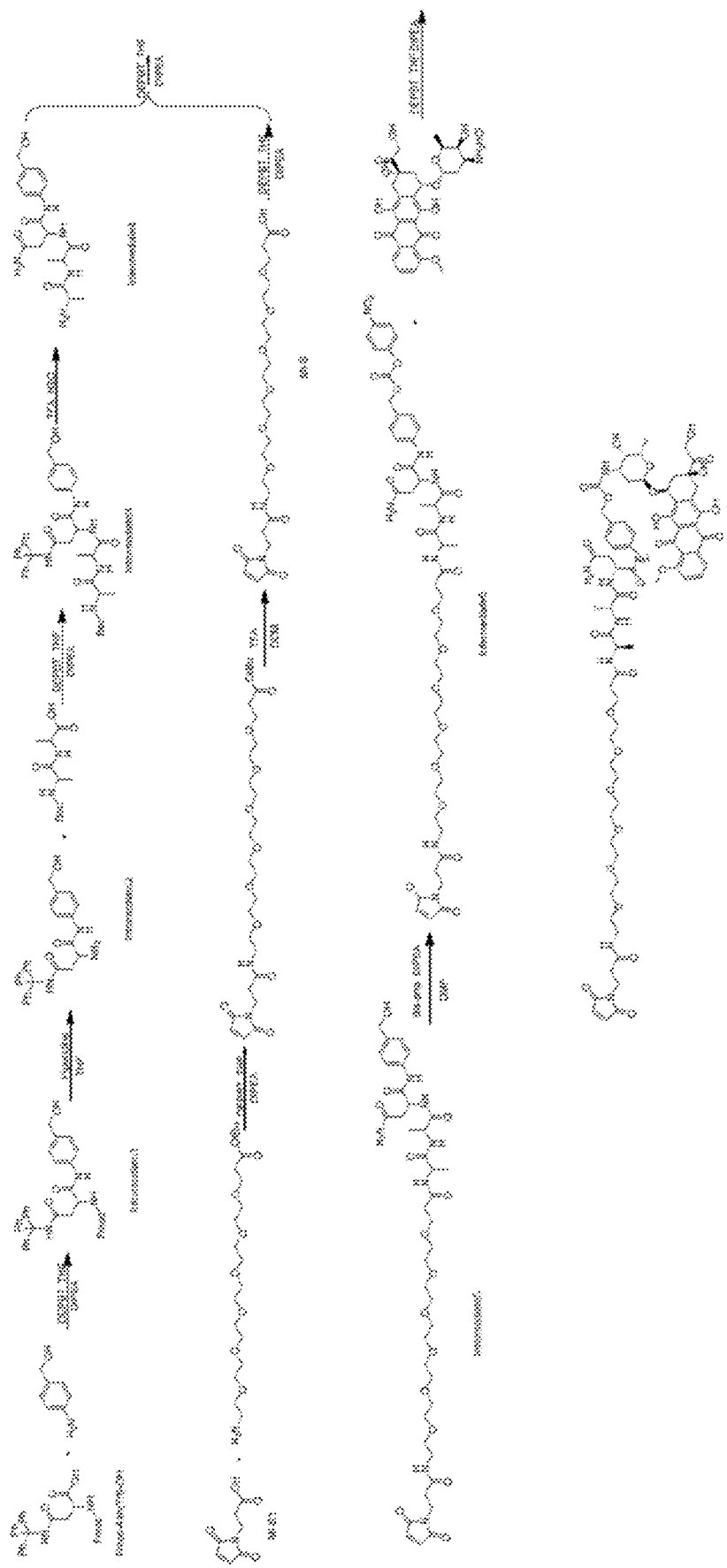

1. Synthesis of Intermediate 1

80 g Fmoc-Asn(Trt)-OH was dissolved in 500 ml THF into a 2 L single-neck reaction flask. 46.6 g DEPBT was added and stirred at room temperature for 15 minutes, added 16 g PABC, and reacted for 30 minutes at room temperature. Added DIPEA 45 ml, protected with nitrogen, and reacted at room temperature for 3 hours. The reaction was monitored by TLC.

The solvents were removed by evaporation under reduced pressure, a small amount of DMF (180 ml) was added to dissolve it, and the residue was drop-wise to 3 L of water under stirring to precipitate a pale yellow solid. After repeated washing with water for 2-3 times, suction filtration was performed to collect the solid and vacuum drying to obtain an off-white solid (Yield: >90%).

2. Synthesis of Intermediate 2

Intermediate 1 was dissolved in 500 ml THF and into 2 L three-necked flask, the temperature was lowered to 0-5° C. with an ice-salt bath, and 100 ml of piperidine was added drop-wise. After the drop-wise addition was completed, the reaction was gradually returned to room temperature for 1 hour. The reaction was monitored by TLC. The solvent was removed under reduced pressure, the residue was dissolved with a small amount of DMF, the solution was added drop-wise to the stirring 2 L water, mechanically stirred for 30 min, filtered with suction, repeated washing with water 2-3 times, filtered with suction, the filter cake was added to 800 ml of methyl tert-butyl ether, stirred for 30 minutes, then filtered with suction. The filter cake was washed twice with PE:EA=10:1, filtered with suction, and the filter cake was collected. After drying under vacuum, 80 g of off-white solid was obtained with a purity of 70%.

3. Synthesis of Intermediate 3

50 ml THF, 5.04 g Boc-Ala-Ala-OH, 3.89 g DEPBT were added orderly to a dry and clean 250 ml single-neck reaction flask, and the reaction was reacted at room temperature for 10 minutes. 2.6 g of NH2-Asn(Trt)-PABC was added, protected by nitrogen, and reacted at room temperature 15 min, Add DIPEA 3.5 ml dropwise, protected by nitrogen, the reaction was reacted at room temperature for 3 hours. The solvent was removed under reduced pressure, the residue was washed by water 2-3 times, and filtered to obtain a pale yellow solid, 3.7 g. The product was purified by column to obtain 2.0 g, purity: 94.8%, yield: 26.6%.

4. Synthesis of Intermediate 4

1.8 g of Intermediate 3 was added to a 250 ml single-necked reaction flask. TFA 28.5 ml was added with stirring, 1.5 ml of water was added drop-wise, and the reaction was allowed to proceed at room temperature for 30 min. The reaction was monitored by TLC. The solvent was removed under reduced pressure. Methyl t-butyl ether was used to wash the residue and filtered to obtain a solid, and the solid was dissolved by Dioxane:water=1:1 solution, 1N sodium hydroxide was added to adjust the pH to 13, and the mixture was stirred at room temperature for 40 min. The solvent was removed under reduced pressure. Purified by silica column to obtain 450 mg of product. Yield: 47.5%.

5. Synthesis of MI-S Intermediate

DMF (15 ml), MI-S1 (338 mg, 2 mmol) and DEPBT (717.6 mg, 2.4 mmol) were added to a 100 ml single-necked flask. Protected by nitrogen, and reacted for 15 min at room temperature. R3-b (819 mg, 2 mmol) was added to the solution, stirred to dissolve, reacted at room temperature for 15 min, added DIPEA 137 μl drop-wise, protected by nitrogen, reacted at room temperature for 3 h, monitored by TLC, R3-a was completely reacted, and the solvent was removed under reduced pressure. The crude product was dissolved in methanol and passed through a reversed-phase high pressure column to obtain the intermediate R3-1 (720 mg, yield: 64.3%).

6. Synthesis of MI-S

The intermediate obtained in the previous step (720 mg, 1.28 mmol) was added to a 100 ml single-mouth reaction flask, 15 ml of dichloromethane was added to dissolve, 5 ml of TFA was added drop-wise, 0.25 ml of water was added drop-wise, and the mixture was reacted at room temperature for 30 min. It was washed with methyl tert-butyl ether and filtered with suction to obtain a solid. The sample was passed through a reverse phase column with silica gel to obtain 242 mg of the product. Yield: 37.5%.

7. Synthesis of Intermediate 5

Intermediate 4 (150 mg, 0.395 mmol) and EMC-6Peg-COOH (239 mg, 0.474 mmol) were added to a 100 ml single-necked flask, dissolved in DMF (15 ml), protected by nitrogen, reacted at room temperature for 15 minutes, and DIPEA 137 μl was added drop-wise, and replaced by nitrogen protected, reacted at room temperature for 3 h, the completion of Intermediate 4 was completely reacted, the solvent was removed under reduced pressure, the crude product was dissolved in methanol, and passed through a reversed-phase high pressure silica gel column to obtain Intermediate 595 mg (Yield: 21%).

8. Synthesis of Intermediate 6

25 ml DMF, Intermediate 5 (300 mg, 0.346 mmol), Bis-PNP (316 mg, 1.04 mmol) were added to a 100 ml single-necked reaction bottle in sequence, protected by nitrogen, reacted at room temperature for 15 minutes, and 258 μl DIPEA was added drop-wise, protected by nitrogen. The mixture was reacted at room temperature for 3 hours. The raw materials were monitored by HPLC. The solvent was removed under reduced pressure, and the product was purified by silica gel column to obtain 150 mg product. Yield: 42%.

9. Synthesis of Final Product QHL-095

84 mg Doxorubicin hydro-chloride (1.0 eq, 0.145 mmol) and 150 mg of intermediate 6 (1.0 eq, 0.145 mmol) were added to a 100 mL reaction flask. The mixture reaction was reacted at room temperature for 15 minutes under nitrogen protection, and 75 μl DIPEA was added drop-wise. The solvent was removed under reduced pressure. The crude product was dissolved in methanol and purified by a reverse-phase high pressure column to obtain QHL-095 (49 mg red solid, yield: 23.8%).

Example 2 Synthesis of QHL-116

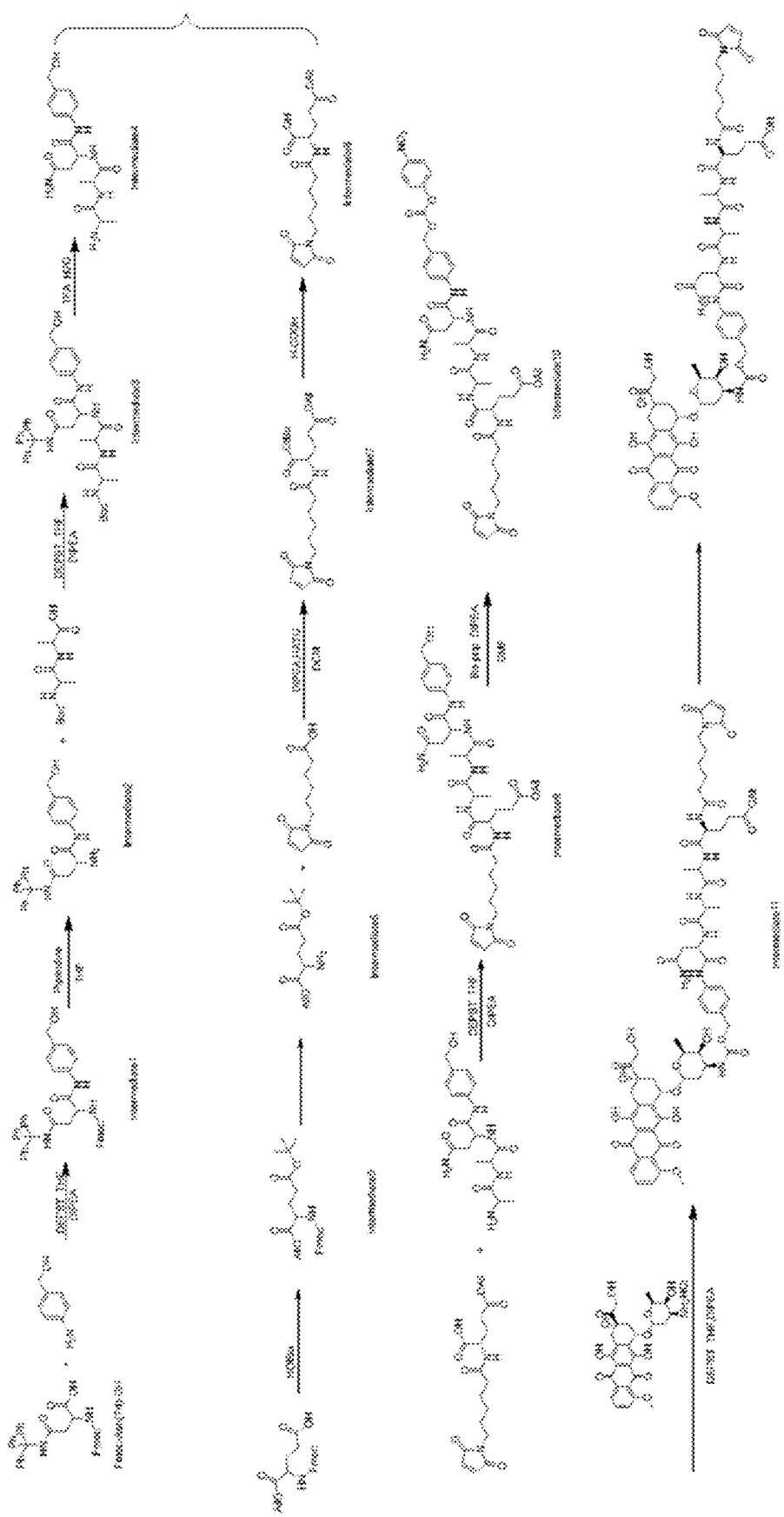

1. Synthesis of Intermediate 1

80 g Fmoc-Asn(Trt)-OH was dissolved in 500 ml THF into a 2 L single-neck reaction flask. 46.6 g DEPBT was added and stirred at room temperature for 15 minutes, added 16 g PABC, and reacted for 30 minutes at room temperature. Added DIPEA 45 ml, protected with nitrogen, and reacted at room temperature for 3 hours. The reaction was monitored by TLC.

The solvents were removed by evaporation under reduced pressure, a small amount of DMF (180 ml) was added to dissolve it, and the residue was drop-wise to 3 L of water under stirring to precipitate a pale yellow solid. After repeated washing with water for 2-3 times, suction filtration was performed to collect the solid and vacuum drying to obtain an off-white solid (Yield: >90%).

2. Synthesis of Intermediate 2

Intermediate 1 was dissolved in 500 ml THF and into 2 L three-necked flask, the temperature was lowered to 0-5° C. with an ice-salt bath, and 100 ml of piperidine was added drop-wise. After the drop-wise addition was completed, the reaction was gradually returned to room temperature for 1 hour. The reaction was monitored by TLC. The solvent was removed under reduced pressure, the residue was dissolved with a small amount of DMF, the solution was added drop-wise to the stirring 2 L water, mechanically stirred for 30 min, filtered with suction, repeated washing with water 2-3 times, filtered with suction, the filter cake was added to 800 ml of methyl tert-butyl ether, stirred for 30 minutes, then filtered with suction. The filter cake was washed twice with PE:EA=10:1, filtered with suction, and the filter cake was collected. After drying under vacuum, 80 g of off-white solid was obtained with a purity of 70%.

3. Synthesis of Intermediate 3

50 ml THF, 5.04 g Boc-Ala-Ala-OH, 3.89 g DEPBT were added orderly to a dry and clean 250 ml single-neck reaction flask, and the reaction was reacted at room temperature for 10 minutes. 2.6 g of NH2-Asn(Trt)-PABC was added, protected by nitrogen, and reacted at room temperature 15 min, Add DIPEA 3.5 ml dropwise, protected by nitrogen, the reaction was reacted at room temperature for 3 hours. The solvent was removed under reduced pressure, the residue was washed by water 2-3 times, and filtered to obtain a pale yellow solid, 3.7 g. The product was purified by column to obtain 2.0 g, purity: 94.8%, yield: 26.6%.

4. Synthesis of Intermediate 4

1.8 g of Intermediate 3 was added to a 250 ml single-necked reaction flask. TFA 28.5 ml was added with stirring, 1.5 ml of water was added drop-wise, and the reaction was allowed to proceed at room temperature for 30 min. The reaction was monitored by TLC. The solvent was removed under reduced pressure. Methyl t-butyl ether was used to wash the residue and filtered to obtain a solid, and the solid was dissolved by Dioxane:water=1:1 solution, 1N sodium hydroxide was added to adjust the pH to 13, and the mixture was stirred at room temperature for 40 min. The solvent was removed under reduced pressure. Purified by silica column to obtain 450 mg of product. Yield: 47.5%.

5. Synthesis of Intermediate 5

Fmoc-Glu(OAll)-COOH (1.554 g, 3.79 mmol) was dissolved in 10 ml of a mixed solution of DCM and THF-.HOtBu 2.72 ml was added drop-wise with stirring. Protected by nitrogen reacted for 16 hours at room temperature. The reaction was monitored by TLC. The solvent was removed under reduced pressure and purified on a silica gel column. Yield: 79.5%.

6. Synthesis of Intermediate 10 ml THF, intermediate 5 (1.4 g, 3 mmol) were added to a dry and clean 250 ml single-necked reaction bottle in turn, stirred to dissolve, the reaction was cooled to 0-5° C. by ice-salt bath, 3 ml of piperidine was added drop-wise, and the temperature was gradually increased to the room temperature reacted for 2 hours. The reaction was monitored by TLC. The solvent was removed under reduced pressure. The residue was purified by silica gel column. The fluent containing the product was collected and dried under reduced pressure to constant weight to obtain 583 mg of the product. Yield: 80%.

7. Synthesis of Intermediate 7

15 ml THF, 583 mg intermediate 6, 932.8 mg DEPBT were added to a dry and clean 250 ml single-necked reaction bottle in turn, reacted for 10 minutes at room temperature, and 506.4 mg of maleimide caproic acid was added, protected by nitrogen, and reacted at room temperature for 15 min, and then 1.3 ml DIPEA was added dropwise, protected by nitrogen, reacted at room temperature for 3 hours. The solvent was removed under reduced pressure, the residue was washed with water 2-3 times, and filtered with suction to obtain a pale yellow solid 800 mg. The solid was purified by silica gel column to obtain 628 mg product. Purity: 94.8%; Yield: 59.9%.

8. Synthesis of Intermediate 8

10 ml dichloromethane and 872 mg intermediate 7 were added to a 100 ml single-mouth reaction bottle in turn. Stirred to dissolve, 3 ml TFA was added drop-wise. The mixture was reacted at room temperature for 2 hours. The raw materials was completely reacted. The solvent was removed under reduced pressure under vacuum. The residue was washed with methyl tert-butyl ether and filtered with suction to obtain a solid. The solid was purified on a silica gel column. The eluent containing the product was collected and dried under reduced pressure to constant weight to obtain 459 mg of the product. Yield: 60.3%.

9. Synthesis of Intermediate 9

15 ml THF, 459 mg intermediate 8, and 434 mg DEPBT were sequentially added to a dry and clean 250 ml single-necked flask, reacted for 10 min at room temperature, 457.8 mg of intermediate 4 was added, protected by nitrogen, and reacted for 15 min at room temperature. 627 µl DIPEA was added drop-wise, protected by nitrogen, reacted at room temperature for 3 hours, removed the solvent under reduced pressure, washed with water 2-3 times, and filtered with suction to obtain a light yellow solid 750 mg, which was purified by silica gel column to obtain 655 mg product. Yield: 63.2%.

10. Synthesis of Intermediate 10

25 ml DMF, Intermediate 9 (655 mg, 0.88 mmol), Bis-PNP (804 mg, 2.64 mmol) were added to a 100-ml single-necked reaction bottle in sequence, protected by nitrogen, reacted at room temperature for 15 minutes, and 258 µl DIPEA was added drop-wise, protected by nitrogen. The reaction was performed at room temperature for 3 hours, and the reaction was monitored by HPLC. The solvent was removed under reduced pressure and purified by silica gel column to obtain 335 mg of the product. Yield: 42%.

11. Synthesis of Intermediate 11

214.3 mg Doxorubicin hydrochloride (1.0 eq, 0.369 mmol) and 335 mg intermediate 10 (1.0 eq, 0.369 mmol) were added to a 100 mL reaction flask, and reacted at room temperature for 15 minutes under nitrogen protection. DIPEA 190 µl was added drop-wise. After 4 hours of reaction at room temperature the solvent was removed under reduced pressure. The crude product was dissolved in methanol and purified by a reversed-phase high pressure column to obtain intermediate 11 (115 mg of a red solid, yield: 23.8%).

12. Synthesis of End Products 15 ml of THF, intermediate 11 (115 mg, 0.0877 mmol), tri-n-butyltin hydrogen (76 mg, 0.2631 mmol) were sequentially added to a 100 mL reaction flask, and the reaction solution was saturated with nitrogen. Tetrakis (triphenylphosphine) palladium (0) (14.2 mg, 0.012 mmol) was then added, and the mixture was stirred at room temperature overnight. Monitored by TLC until conversion was completely. The contents of the flask were then filtered through celite and the residue was washed with THF. The filtrate was concentrated under reduced pressure. The obtained crude product was purified by a silica gel column to obtain 100 mg (yield: 90%) of the target compound.

Example 3 Synthesis of QHL-006

The MI-S group in QHL-006, the synthetic route is as follows:

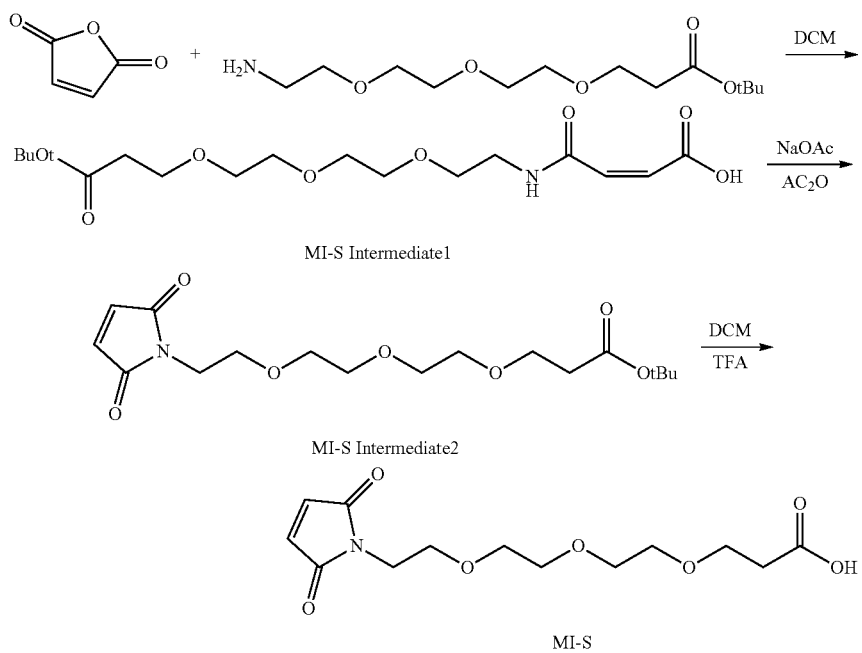

1. Synthesis of MI-S Intermediate-1 in QHL-006

Maleic anhydride (245 mg, 2.5 mmol), 10 ml dichloromethane were added to a dry and clean 100 ml single-mouth reaction flask, stirred and dissolved, $NH_2$-3Peg-COOtBu (624 mg, 2.25 mmol) was added, and the mixture was reacted at room temperature for 6 hours. Monitored by LC-MS until maleic anhydride was completely reaction. The reaction solvent was removed under reduced pressure, and purified by the silica gel column to obtain MI-S Intermediate-1 (456 mg, yield: 48.6%).

2. Synthesis of MI-S Intermediate-2 in QHL-006

456 mg MI-S Intermediate-1 was added to a 100 ml single-necked reaction flask, 10 ml acetic anhydride was added and dissolved by stirring, and NaOAC (98.7 mg, 1.216 mmol) was weighed in and added slowly in batches. The reaction solution was heated to 110° C. and reacted for 3 h. LC-MS monitored the completion of MI-S Intermediate-1, cooled to room temperature, The reaction solution was removed under reduced pressure, and the residue was purified by silica gel column to obtain MI-S Intermediate-2 (312 mg, yield: 70%).

3. Synthesis of MI-S in QHL-006

MI-S Intermediate-2 (312 mg, 0.87 mmol) was added to a 100 ml single-mouth reaction flask, 10 ml of dichloromethane was added to dissolve, 2 ml of TFA was added drop-wise, 0.15 ml water was added drop-wise, and the reaction was allowed to proceed at room temperature for 30 min. The solvent was washed with methyl tert-butyl ether, and filtered with suction to obtain a solid, which was purified by a reverse phase column to obtain 196 mg of the product. Yield: 75%.

The final product was synthesized by a similar method to QHL-095, and connected with different MI-S (the preparation of MI-S refers to the synthesis process of MI-S in QHL-006)

When A is Leu, the synthetic route is as follows:

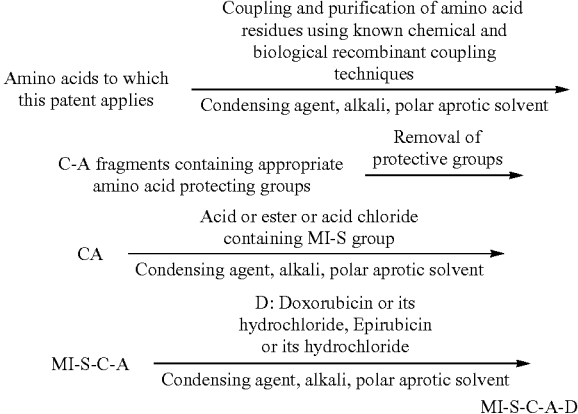

Example 4 Synthesis of QHL-096
As shown in the figure below, taking QHL-096 as an example, the specific synthesis process is as follows:
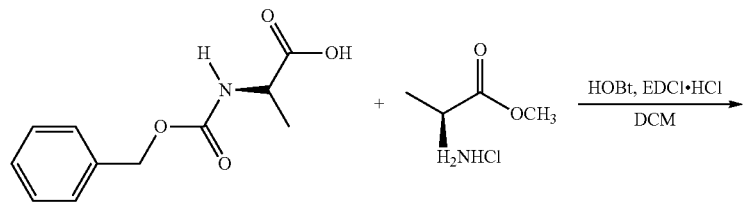
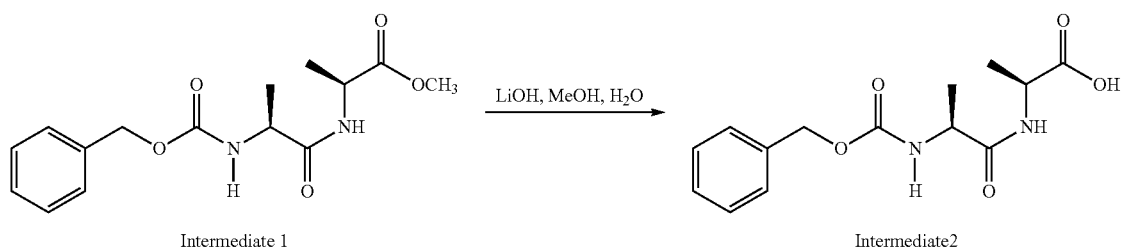
Intermediate 1          Intermediate2
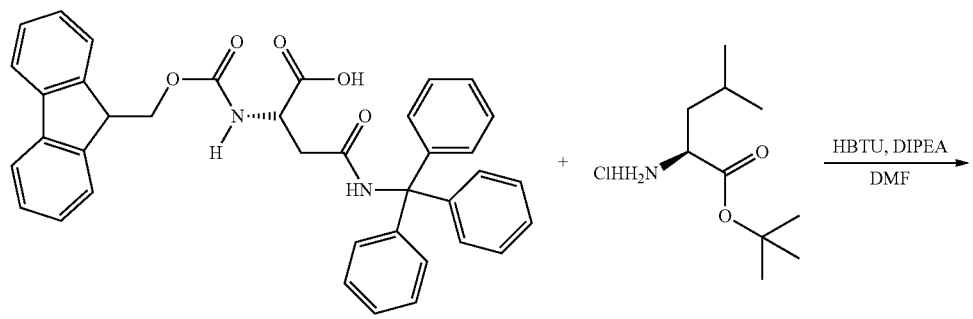
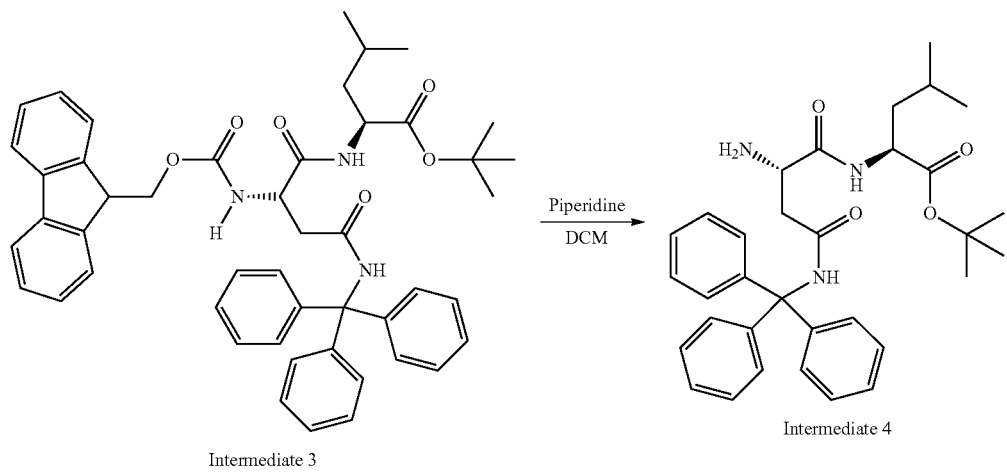
Intermediate 3          Intermediate 4

-continued
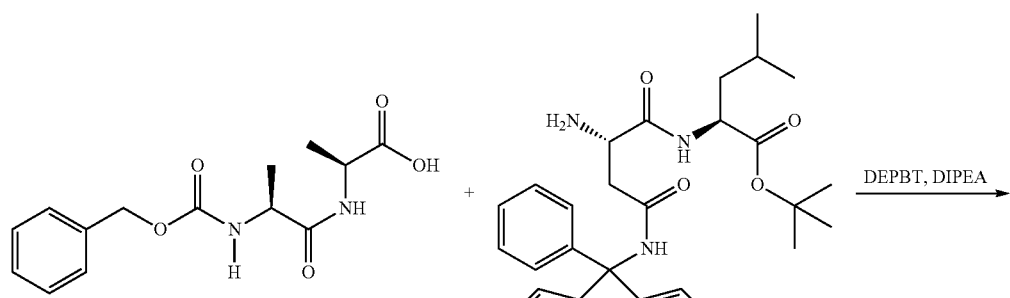
Intermediate2 + Intermediate4 →(DEPBT, DIPEA)
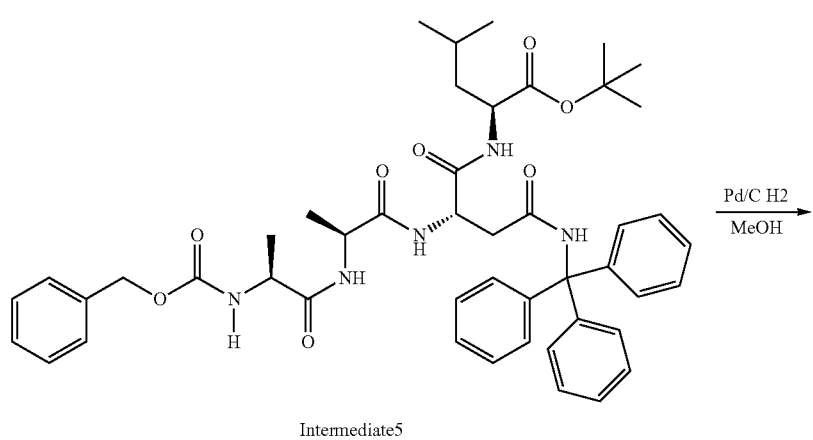
Intermediate5
→(Pd/C H2, MeOH)
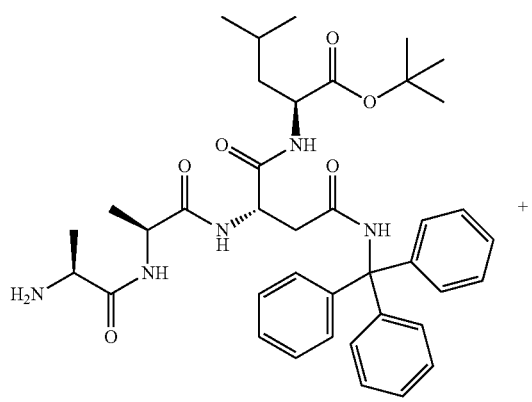
Molecular Weight: 685.87
Intermediate6
+
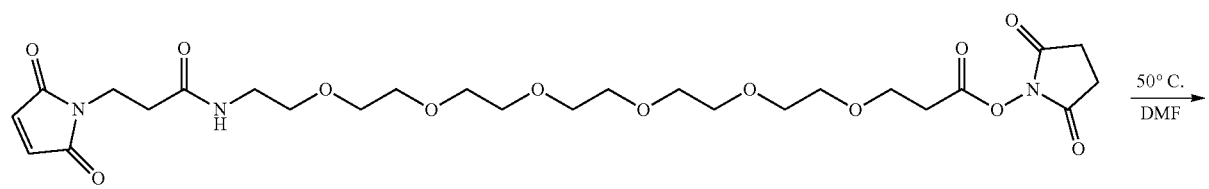
→(50° C., DMF)

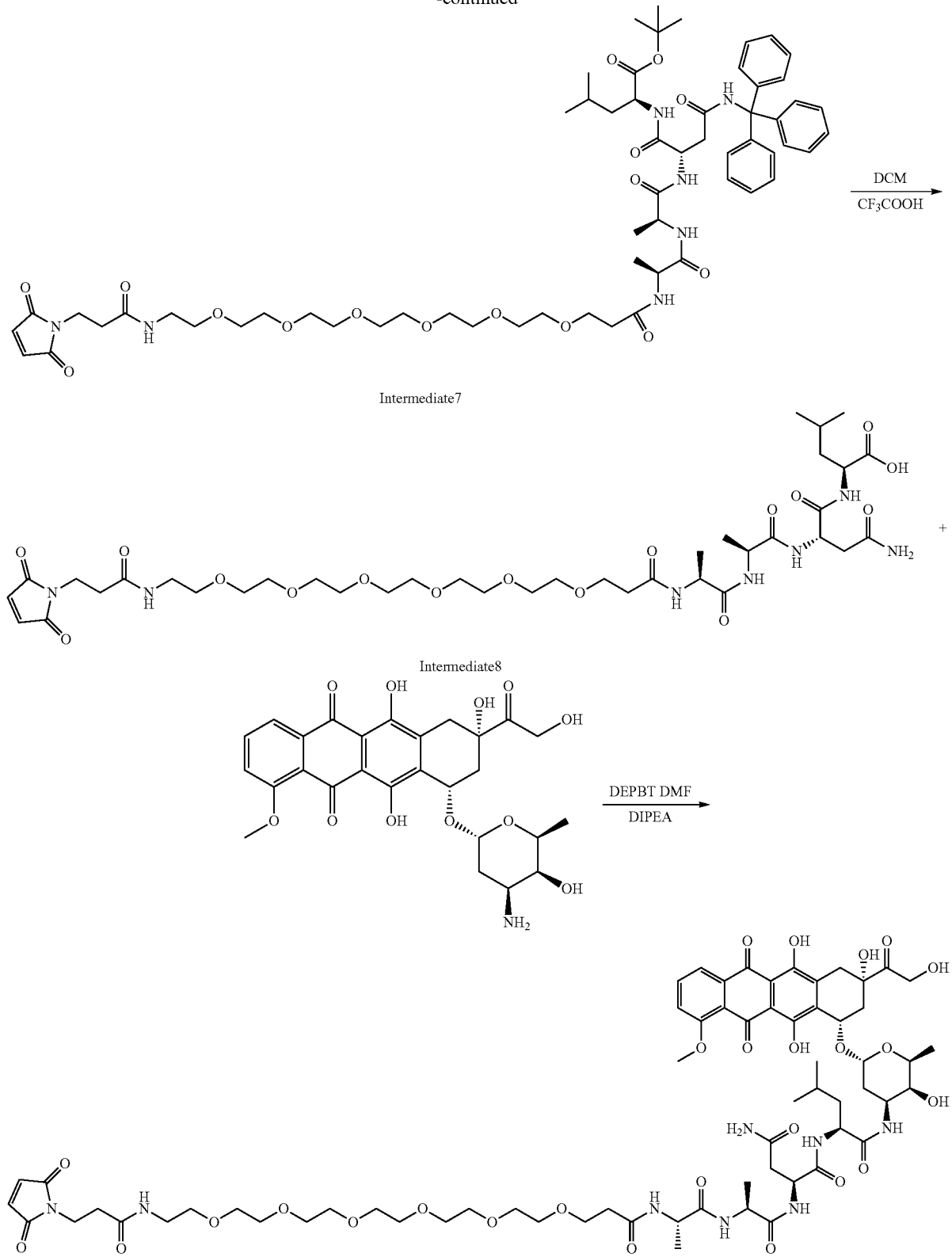

Intermediate7

Intermediate8

1) Synthesis of Intermediate 1

N-benzyloxycarbonyl-L-alanine (100 g, 0.45 mol) is dissolved in dry N, N-dimethylformamide (3 L), 1-hydroxybenzotriazole (72.6 g, 0.54 mol) and 1-ethyl-(3-dimethylaminopropyl) carbodiimide hydro-chloride (103.3 g, 0.54 mol) were added with stirring, After the reaction was stirred for 1 hour, L-alanine methyl ester (46.2 g, 0.45 mol) and N, N-diisopropylethylamine (173.8 g, 1.34 mol) of N were added drop-wise in an ice bath to 0° C. N-dimethylformamide (1 L) solution, after the drop-wise addition was completed, the mixture was stirred at room temperature for 10 hours. The solvent was removed under reduced pressure. The crude product was dissolved in dichloromethane (2 L) and washed with a saturated ammonium chloride solution, water and a saturated sodium chloride solution in this order. The organic phase was dried over anhydrous sodium sulfate, filtered under suction, and the filtrate was evaporated under reduced pressure to remove the solvent. The crude product was recrystallized from ethyl acetate/petroleum ether to obtain the pure product as intermediate I (101 g of white solid, yield: 73.1%).

2) Synthesis of Intermediate 2

Intermediate 1 (100 g, 0.34 mol) was dissolved in a mixed solution of tetrahydrofuran (2 L) and water (1 L), and cooled to 0° C., and a 1 mol/liter lithium hydroxide solution (400 mL) was added dropwise. The reaction was stirred for 10 hours. Added concentrated hydrochloric acid dropwise to neutralize PH<6, tetrahydrofuran was removed under reduced pressure, and the remaining aqueous phase was extracted with dichloromethane (1 L×3). The organic phase was dried over anhydrous sodium sulfate, suction filtered, and the filtrate was evaporated to dryness under reduced pressure to obtain intermediate 2 (88 g of white solid, yield: 92.2%).

3) Synthesis of Intermediate 3

L-leucine tert-butyl ester (22.4 g, 0.1 mol), N-Fmoc-N'-trityl asparagine (59.6 g, 0.1 mol) were dissolved in N, N-dimethylformamide (1000 mL), 1-Hydroxybenzotriazole (14.85 g, 0.11 mol) and 1-ethyl-(3-dimethylaminopropyl) carbodiimide hydrochloride (23 g, 0.12 mol) were added with stirring. The temperature of the reaction was reduced to 0° C. with the ice bath, and N, N-diisopropylethylamine (25.8 g, 0.2 mol) was added. After stirring for 10 hours, the solvent was distilled off under reduced pressure. The crude product was dissolved in chloroform (1000 ml), and the solvent was washed with a saturated ammonium chloride solution, a saturated sodium chloride solution, and water in turn. The organic phase was dried over anhydrous sodium sulfate, filtered, and the filtrate was evaporated under reduced pressure to obtain a crude product which was recrystallized (by volume, methylene chloride):Ethyl acetate=1:1) Intermediate 3 (42.4 g of white solid, yield: 55.4%) was obtained after purification.

4) Synthesis of Intermediate 4

Intermediate 3 (7.65 g, 0.01 mol) was dissolved in a mixed solution of dichloromethane (100 mL) and N, N-dimethylformamide (100 mL), and then piperidine (40 ml) was added, followed by stirring at room temperature for 5 hours. The solvent was distilled off under reduced pressure, and then placed in a vacuum drying box under high vacuum to remove a small amount of piperidine to obtain intermediate 4 as a pale yellow solid, which was directly used in the next step without purification.

5) Synthesis of Intermediate 5

The crude intermediate 4 obtained in the previous step was dissolved in N, N-dimethylformamide (200 mL), and intermediate 2 (2.94 g, 0.012 mol) and HBTU (6.07 g, 0.016 mol) were added. After cooling to 0° C. in an ice bath, N, N-diisopropylethylamine (2.6 g, 0.02 mol) was added, and the mixture was stirred overnight at room temperature. The solvent was distilled off under reduced pressure. The residue was dissolved in chloroform (100 ml) and used successively saturated ammonium chloride solution and saturated sodium chloride solution were washed, dried over anhydrous sodium sulfate, filtered, and the solvent was distilled off. The obtained crude product was purified by silica gel column chromatography to obtain intermediate 5 (3.1 g of white solid, total yield in two steps: 37.8%).

6) Synthesis of Intermediate 6

Cbz-AAN(trt)-L-Otbu (3.00 g, 3.65 mmol) was dissolved in methanol (100 mL), 10% palladium carbon (0.3 g) was added, hydrogen was passed in, and the reaction was stirred at room temperature and pressure for 4 hours, and filtered the palladium-carbon was removed, washed with methanol, and the filtrate and lotions were combined. The solvent was distilled off under reduced pressure to obtain Intermediate 6 (2.38 g of white solid, yield: 95.2%).

7) Synthesis of Intermediate 7

Intermediate 6 (2.38 g, 3.4 mmol) and EMC-6Peg-OSu (2.4 g, 4.08 mmol) were added into a 250 ml single-necked flask, DMF (15 ml) was added to dissolve it, and the mixture was heated to 50° C. for 6 hours to react. The solvent was distilled off under reduced pressure, and the crude product was dissolved in methanol, and purified by reverse-phase high-pressure column to obtain intermediate 7 (2.5 g, yield: 63.2%).

8) Synthesis of Intermediate 8

Intermediate 7 (1.00 g, 0.852 mmol) was dissolved in DCM (20 mL). Trifluoroacetic acid (10 ml) was added dropwise at room temperature, and the reaction was stirred for 2 h. HPLC monitoring showed that the reaction of intermediate 1 was complete, and the solvent was removed under reduced pressure. The crude product was washed twice with methyl tert-butyl ether, the solid was dissolved in methanol, and purified by reverse phase high pressure column to obtain intermediate 8 (721 mg white solid, yield: 96.8%).

9) Synthesis of Final Product QHL-096

10 mL DMF, 63 mg of Doxorubicin hydrochloride (1.0 eq), 95 mg of intermediate 8 (1 eq), and 39 mg of DEPBT (1.2 eq) were sequentially added to a 100 mL reaction flask. 60 ul of DIPEA (3 eq). After 4 hours of reaction at room temperature, the solvent was distilled off under reduced pressure. The crude product was dissolved in methanol and purified by reverse-phase high-pressure column to obtain S (52 mg red solid, yield: 34.2%).

Example 5 Synthesis of QHL-117

The synthesis route of QHL-117 is as follows:

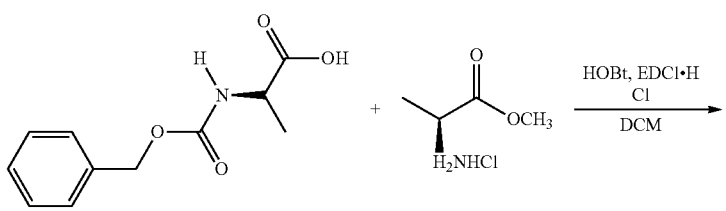

-continued
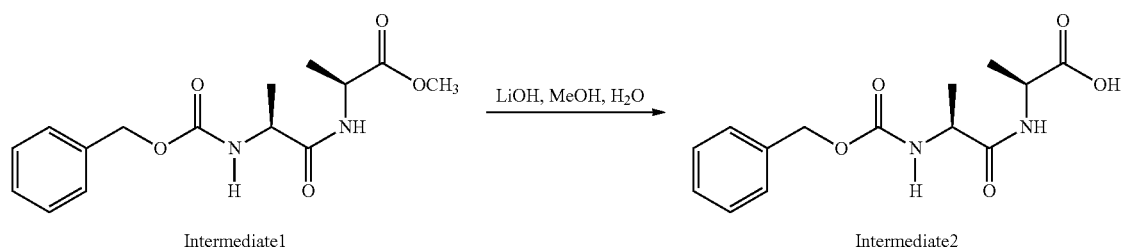
Intermediate1 → Intermediate2
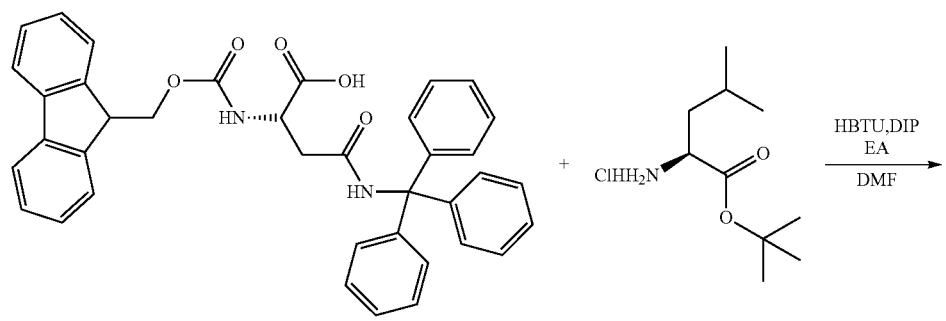
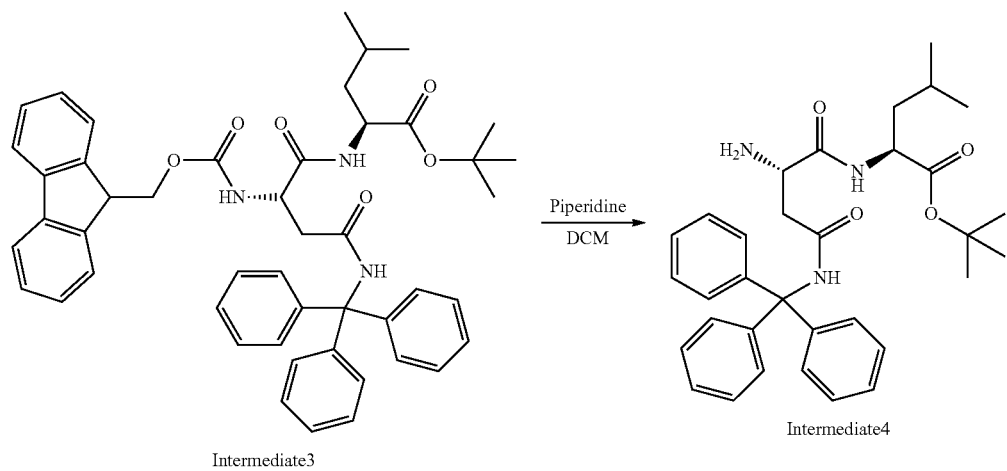
Intermediate3 → Intermediate4
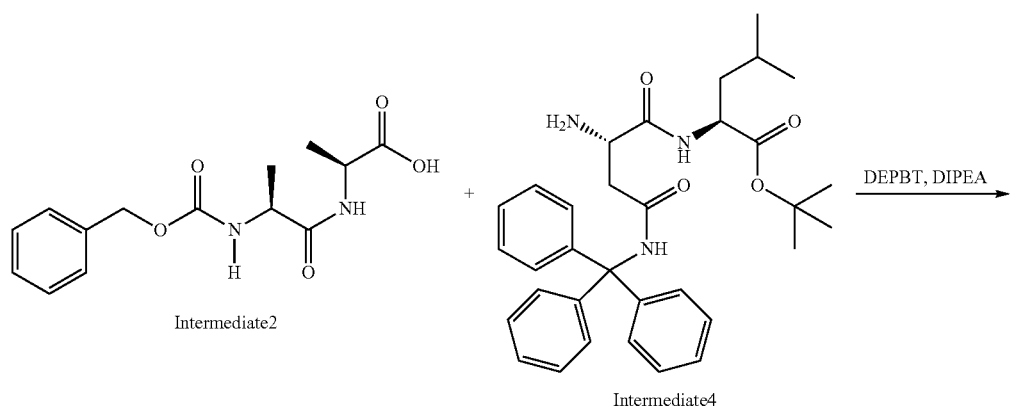
Intermediate2 + Intermediate4

-continued
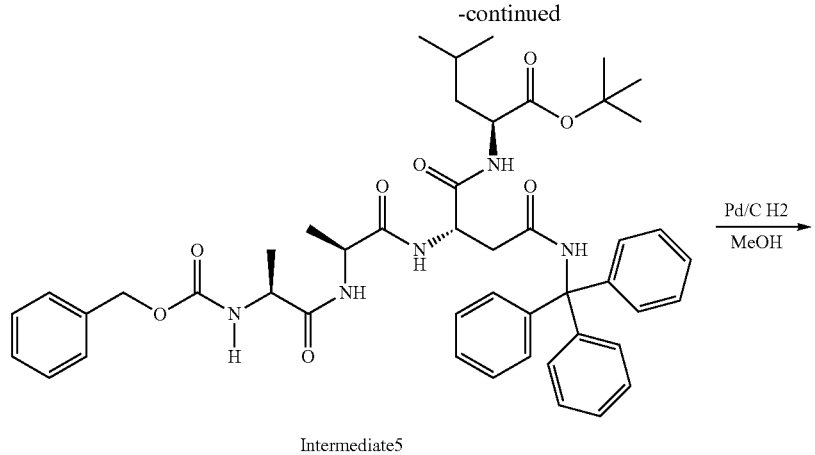
Intermediate5
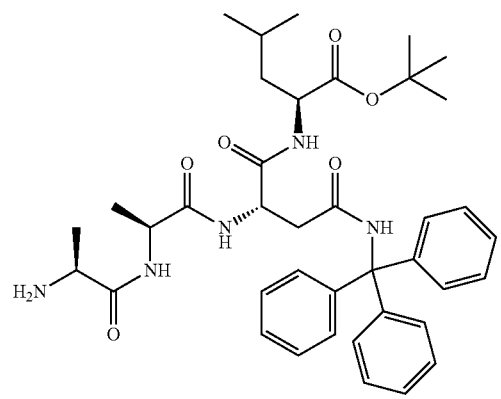
Intermediate6
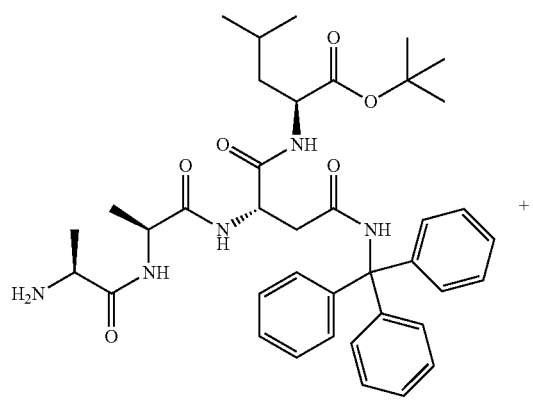
Intermediate6
+
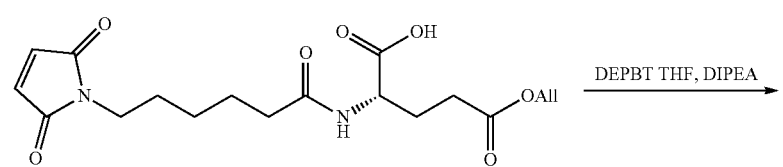

-continued
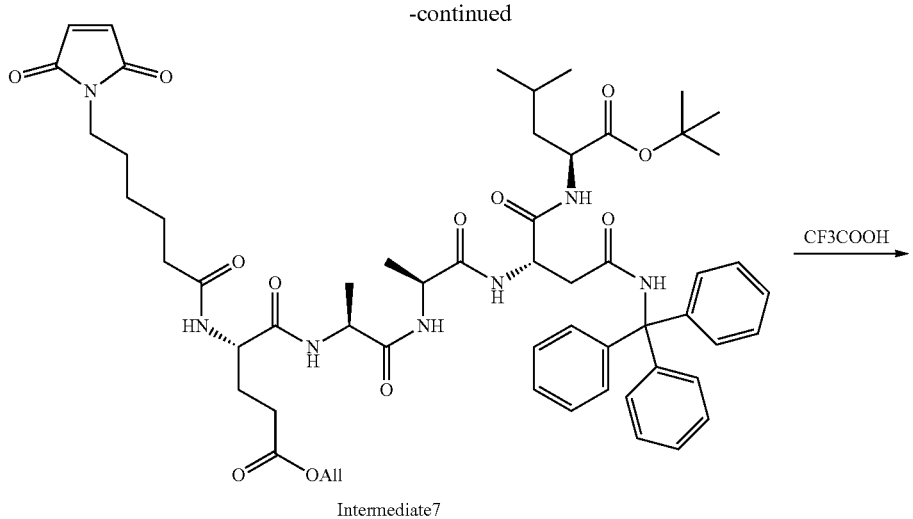
Intermediate7
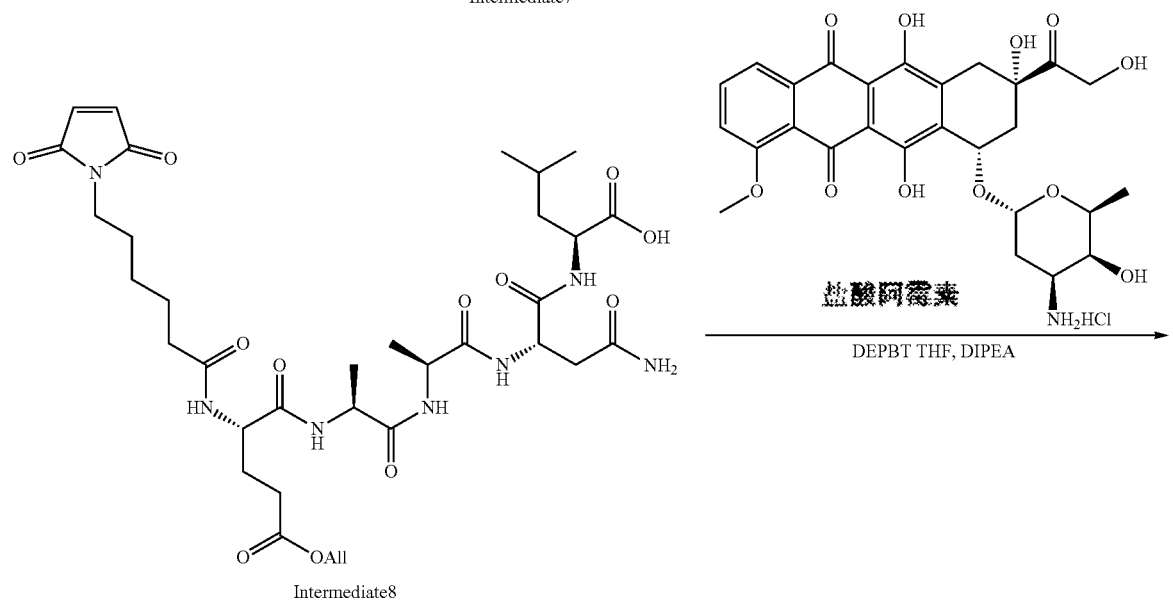
Intermediate8
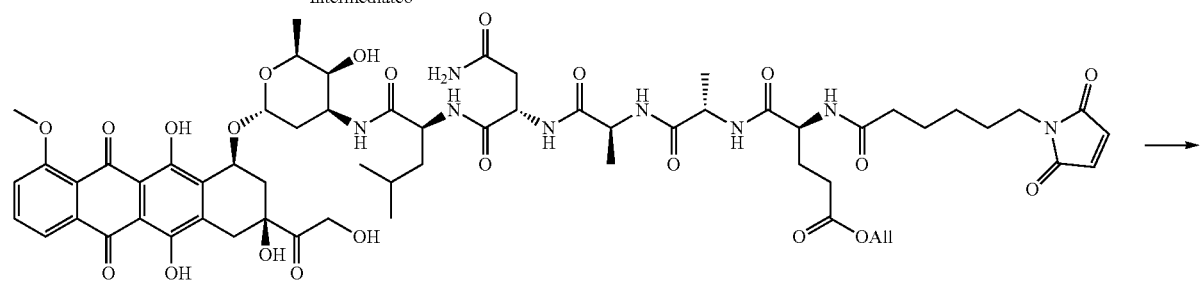
Intermediate9
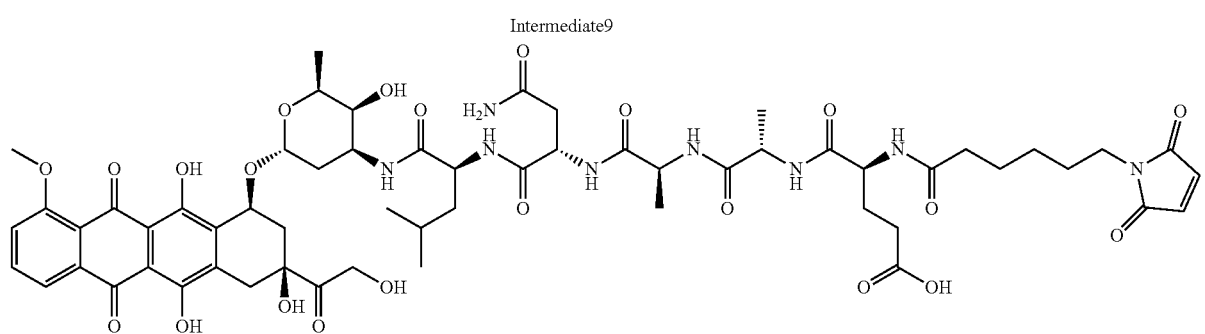

1) Synthesis of Intermediate 1

N-benzyloxycarbonyl-L-alanine (100 g, 0.45 mol) is dissolved in dry N, N-dimethylformamide (3 L), 1-hydroxybenzotriazole (72.6 g, 0.54 mol) and 1-ethyl-(3-dimethylaminopropyl) carbodiimide hydro-chloride (103.3 g, 0.54 mol) were added with stirring, After the reaction was stirred for 1 hour, L-alanine methyl ester (46.2 g, 0.45 mol) and N, N-diisopropylethylamine (173.8 g, 1.34 mol) of N were added drop-wise in an ice bath to 0° C. N-dimethylformamide (1 L) solution, after the drop-wise addition was completed, the mixture was stirred at room temperature for 10 hours. The solvent was removed under reduced pressure. The crude product was dissolved in dichloromethane (2 L) and washed with a saturated ammonium chloride solution, water and a saturated sodium chloride solution in this order. The organic phase was dried over anhydrous sodium sulfate, filtered under suction, and the filtrate was evaporated under reduced pressure to remove the solvent. The crude product was recrystallized from ethyl acetate/petroleum ether to obtain the pure product as intermediate I (101 g of white solid, yield: 73.1%).

2) Synthesis of Intermediate 2

Intermediate 1 (100 g, 0.34 mol) was dissolved in a mixed solution of tetrahydrofuran (2 L) and water (1 L), and cooled to 0° C., and a 1 mol/liter lithium hydroxide solution (400 mL) was added dropwise. The reaction was stirred for 10 hours. Added concentrated hydrochloric acid dropwise to neutralize PH<6, tetrahydrofuran was removed under reduced pressure, and the remaining aqueous phase was extracted with dichloromethane (1 L×3). The organic phase was dried over anhydrous sodium sulfate, suction filtered, and the filtrate was evaporated to dryness under reduced pressure to obtain intermediate 2 (88 g of white solid, yield: 92.2%).

3) Synthesis of Intermediate 3

L-leucine tert-butyl ester (22.4 g, 0.1 mol), N-Fmoc-N'-trityl asparagine (59.6 g, 0.1 mol) were dissolved in N, N-dimethylformamide (1000 mL), 1-Hydroxybenzotriazole (14.85 g, 0.11 mol) and 1-ethyl-(3-dimethylaminopropyl) carbodiimide hydrochloride (23 g, 0.12 mol) were added with stirring. The temperature of the reaction was reduced to 0° C. with the ice bath, and N, N-diisopropylethylamine (25.8 g, 0.2 mol) was added. After stirring for 10 hours, the solvent was distilled off under reduced pressure. The crude product was dissolved in chloroform (1000 ml), and the solvent was washed with a saturated ammonium chloride solution, a saturated sodium chloride solution, and water in turn. The organic phase was dried over anhydrous sodium sulfate, filtered, and the filtrate was evaporated under reduced pressure to obtain a crude product which was recrystallized (by volume, methylene chloride):Ethyl acetate=1:1) Intermediate 3 (42.4 g of white solid, yield: 55.4%) was obtained after purification.

4) Synthesis of Intermediate 4

Intermediate 3 (7.65 g, 0.01 mol) was dissolved in a mixed solution of dichloromethane (100 mL) and N, N-dimethylformamide (100 mL), and then piperidine (40 ml) was added, followed by stirring at room temperature for 5 hours. The solvent was distilled off under reduced pressure, and then placed in a vacuum drying box under high vacuum to remove a small amount of piperidine to obtain intermediate 4 as a pale yellow solid, which was directly used in the next step without purification.

5) Synthesis of Intermediate 5

The crude intermediate 4 obtained in the previous step was dissolved in N, N-dimethylformamide (200 mL), and intermediate 2 (2.94 g, 0.012 mol) and HBTU (6.07 g, 0.016 mol) were added. After cooling to 0° C. in an ice bath, N, N-diisopropylethylamine (2.6 g, 0.02 mol) was added, and the mixture was stirred overnight at room temperature. The solvent was distilled off under reduced pressure. The residue was dissolved in chloroform (100 ml) and used successively saturated ammonium chloride solution and saturated sodium chloride solution were washed, dried over anhydrous sodium sulfate, filtered, and the solvent was distilled off. The obtained crude product was purified by silica gel column chromatography to obtain intermediate 5 (3.1 g of white solid, total yield in two steps: 37.8%).

6) Synthesis of Intermediate 6

Cbz-AAN(trt)-L-Otbu (3.00 g, 3.65 mmol) was dissolved in methanol (100 mL), 10% palladium carbon (0.3 g) was added, hydrogen was passed in, and the reaction was stirred at room temperature and pressure for 4 hours, and filtered the palladium-carbon was removed, washed with methanol, and the filtrate and lotions were combined. The solvent was distilled off under reduced pressure to obtain Intermediate 6 (2.38 g of white solid, yield: 95.2%).

7) Synthesis of Intermediate 7

15 ml THF, Intermediate 6 (2.387 g, 3.4 mmol), and 1.35 g DEPBT were sequentially added to a dry and clean 250 ml single-necked flask, reacted for 10 min at room temperature, EMC-Glu(OAll)-COOH (2.387 g, 3.4 mmol) was added, protected by nitrogen, and reacted for 15 min at room temperature. Protected by nitrogen, 1.8 ml DIPEA was added dropwise, reacted at room temperature for 3 hours, removed the solvent under reduced pressure, washed with water 2-3 times, and filtered with suction to obtain a light yellow solid 700 mg, which was purified by silica gel column to obtain 2.2 g product. Yield: 63.2%.

8). Synthesis of Intermediate 8

Intermediate 7 (1.53 g, 1.46 mmol) was dissolved in DCM (20 mL). Trifluoroacetic acid (10 ml) was added dropwise at room temperature, and the reaction was stirred for 2 h. HPLC monitoring showed that the reaction of intermediate 1 was complete, and the solvent was removed under reduced pressure. The crude product was washed twice with methyl tert-butyl ether, the solid was dissolved in methanol, and purified by reverse phase high pressure column to obtain intermediate 8 (928 mg white solid, yield: 84.8%).

9). Synthesis of Intermediate 9

510.4 mg Doxorubicin hydrochloride (1.0 eq, 0.88 mmol) and 659 mg intermediate 8 (1.0 eq, 0.88 mmol) were added to a 100 mL reaction flask, and reacted at room temperature for 15 minutes under nitrogen protection. DIPEA 460 μl was added drop-wise. After 4 hours of reaction at room temperature the solvent was removed under reduced pressure. The crude product was dissolved in methanol and purified by a reversed-phase high pressure column to obtain intermediate 9 (258 mg of a red solid, yield: 23.8%).

12. Synthesis of End Products 15 ml of THF, intermediate 9 (258 mg, 0.202 mmol), tri-n-butyltin hydrogen (175.7 mg, 0.606 mmol) were sequentially added to a 100 mL reaction flask, and the reaction solution was saturated with nitrogen. Tetrakis (triphenylphosphine) palladium (0) (32.7 mg, 0.028 mmol) was then added, and the mixture was stirred at room temperature overnight. Monitored by TLC until conversion was completely. The contents of the flask were then filtered through celite and the residue was washed with THF. The filtrate was concentrated under reduced pressure. The obtained crude product was purified by a silica gel column to obtain 224 mg (yield: 90%) of the target compound.

For other different C groups, a similar method to QHL-005 was used to connect different amino acid residues to prepare intermediates 6 with different peptide chains.

Other different MI-S groups, Using a similar method to QHL-005 or QHL-006, synthetic intermediate MI-S.

The final product was synthesized by a method similar to that used in Examples 1, 3, 4, 5 and different MI-S was used to prepare all the compounds QHL-001 to QHL-137.

The compounds QHL-001 to QHL-137 were verified by mass spectrometry (MS), and their molecular weights are shown in Table 2, which is consistent with the calculated molecular weights based on their structures.

TABLE 2

| Compound number | Molecular weight | MS | Character | Production |
|---|---|---|---|---|
| QHL-001 | 1143.16 | 1143 | red solid powder | 71 mg |
| QHL-002 | 1187.22 | 1187 | red solid powder | 49 mg |
| QHL-003 | 1231.27 | 1231 | red solid powder | 112 mg |
| QHL-004 | 1319.37 | 1319 | red solid powder | 93 mg |
| QHL-005 | 1144.15 | 1144 | red solid powder | 37 mg |
| QHL-006 | 1188.21 | 1188 | red solid powder | 46 mg |
| QHL-007 | 1232.26 | 1232 | red solid powder | 158 mg |
| QHL-008 | 1320.36 | 1320 | red solid powder | 102 mg |
| QHL-009 | 1152.17 | 1152 | red solid powder | 34 mg |
| QHL-010 | 1196.23 | 1196 | red solid powder | 28 mg |
| QHL-011 | 1240.28 | 1240 | red solid powder | 18 mg |
| QHL-012 | 1328.38 | 1328 | red solid powder | 31 mg |
| QHL-013 | 1272.27 | 1272 | red solid powder | 180 mg |
| QHL-014 | 1316.33 | 1316 | red solid powder | 105 mg |
| QHL-015 | 1360.38 | 1360 | red solid powder | 214 mg |
| QHL-016 | 1448.48 | 1448 | red solid powder | 54 mg |
| QHL-017 | 1273.26 | 1273 | red solid powder | 189 mg |
| QHL-018 | 1317.32 | 1317 | red solid powder | 167 mg |
| QHL-019 | 1361.37 | 1361 | red solid powder | 102 mg |
| QHL-020 | 1449.47 | 1449 | red solid powder | 81 mg |
| QHL-021 | 1281.28 | 1281 | red solid powder | 106 mg |
| QHL-022 | 1325.34 | 1325 | red solid powder | 97 mg |
| QHL-023 | 1369.39 | 1369 | red solid powder | 139 mg |
| QHL-024 | 1457.49 | 1457 | red solid powder | 76 mg |
| QHL-025 | 1258.24 | 1258 | red solid powder | 143 mg |
| QHL-026 | 1302.3 | 1302 | red solid powder | 125 mg |
| QHL-027 | 1346.35 | 1346 | red solid powder | 136 mg |
| QHL-028 | 1434.45 | 1434 | red solid powder | 121 mg |
| QHL-029 | 1259.23 | 1259 | red solid powder | 223 mg |
| QHL-030 | 1303.29 | 1303 | red solid powder | 184 mg |
| QHL-031 | 1347.34 | 1347 | red solid powder | 98 mg |
| QHL-032 | 1435.44 | 1435 | red solid powder | 131 mg |
| QHL-033 | 1267.25 | 1267 | red solid powder | 135 mg |
| QHL-034 | 1311.31 | 1311 | red solid powder | 154 mg |
| QHL-035 | 1355.36 | 1355 | red solid powder | 164 mg |
| QHL-036 | 1443.46 | 1443 | red solid powder | 182 mg |
| QHL-037 | 1343.35 | 1343 | red solid powder | 155 mg |
| QHL-038 | 1344.34 | 1344 | red solid powder | 169 mg |
| QHL-039 | 1352.36 | 1352 | red solid powder | 156 mg |
| QHL-040 | 1329.32 | 1329 | red solid powder | 231 mg |
| QHL-041 | 1330.31 | 1330 | red solid powder | 143 mg |
| QHL-042 | 1338.33 | 1338 | red solid powder | 157 mg |
| QHL-043 | 1387.41 | 1387 | red solid powder | 241 mg |
| QHL-044 | 1388.4 | 1388 | red solid powder | 185 mg |
| QHL-045 | 1396.42 | 1396 | red solid powder | 174 mg |
| QHL-046 | 1373.38 | 1373 | red solid powder | 169 mg |
| QHL-047 | 1374.37 | 1374 | red solid powder | 64 mg |
| QHL-048 | 1382.39 | 1382 | red solid powder | 105 mg |
| QHL-049 | 1431.46 | 1431 | red solid powder | 98 mg |
| QHL-050 | 1432.45 | 1432 | red solid powder | 216 mg |
| QHL-051 | 1440.47 | 1440 | red solid powder | 198 mg |
| QHL-052 | 1417.43 | 1417 | red solid powder | 183 mg |
| QHL-053 | 1418.42 | 1418 | red solid powder | 175 mg |
| QHL-054 | 1426.44 | 1426 | red solid powder | 168 mg |
| QHL-055 | 1519.56 | 1520 | red solid powder | 156 mg |
| QHL-056 | 1520.55 | 1521 | red solid powder | 141 mg |
| QHL-057 | 1528.57 | 1529 | red solid powder | 139 mg |
| QHL-058 | 1505.53 | 1506 | red solid powder | 145 mg |
| QHL-059 | 1506.52 | 1507 | red solid powder | 182 mg |
| QHL-060 | 1514.54 | 1515 | red solid powder | 163 mg |
| QHL-061 | 1357.38 | 1357 | red solid powder | 196 mg |
| QHL-062 | 1358.37 | 1358 | red solid powder | 175 mg |
| QHL-063 | 1366.39 | 1366 | red solid powder | 154 mg |
| QHL-064 | 1343.35 | 1343 | red solid powder | 139 mg |
| QHL-065 | 1344.34 | 1344 | red solid powder | 28 mg |
| QHL-066 | 1352.36 | 1352 | red solid powder | 18 mg |
| QHL-067 | 1401.44 | 1401 | red solid powder | 31 mg |
| QHL-068 | 1402.43 | 1402 | red solid powder | 164 mg |
| QHL-069 | 1410.45 | 1410 | red solid powder | 84 mg |
| QHL-070 | 1387.41 | 1387 | red solid powder | 115 mg |
| QHL-071 | 1388.4 | 1388 | red solid powder | 54 mg |
| QHL-072 | 1396.42 | 1396 | red solid powder | 189 mg |
| QHL-073 | 1445.49 | 1445 | red solid powder | 167 mg |
| QHL-074 | 1446.48 | 1446 | red solid powder | 102 mg |
| QHL-075 | 1454.5 | 1455 | red solid powder | 81 mg |
| QHL-076 | 1431.46 | 1431 | red solid powder | 106 mg |
| QHL-077 | 1432.45 | 1432 | red solid powder | 97 mg |
| QHL-078 | 1440.47 | 1440 | red solid powder | 139 mg |
| QHL-079 | 1533.59 | 1534 | red solid powder | 76 mg |
| QHL-080 | 1534.58 | 1535 | red solid powder | 143 mg |
| QHL-081 | 1542.6 | 1543 | red solid powder | 125 mg |
| QHL-082 | 1519.56 | 1520 | red solid powder | 136 mg |
| QHL-083 | 1520.55 | 1521 | red solid powder | 121 mg |
| QHL-084 | 1528.57 | 1529 | red solid powder | 223 mg |
| QHL-085 | 1214.24 | 1214 | red solid powder | 184 mg |
| QHL-086 | 1215.23 | 1215 | red solid powder | 74 mg |
| QHL-087 | 1223.25 | 1223 | red solid powder | 121 mg |
| QHL-088 | 1258.3 | 1258 | red solid powder | 157 mg |
| QHL-089 | 1259.29 | 1259 | red solid powder | 84 mg |
| QHL-090 | 1267.31 | 1267 | red solid powder | 164 mg |
| QHL-091 | 1302.35 | 1302 | red solid powder | 182 mg |
| QHL-092 | 1303.34 | 1303 | red solid powder | 155 mg |
| QHL-093 | 1311.36 | 1311 | red solid powder | 169 mg |
| QHL-094 | 1390.45 | 1390 | red solid powder | 156 mg |
| QHL-095 | 1391.44 | 1391 | red solid powder | 49 mg |
| QHL-096 | 1399.46 | 1399 | red solid powder | 52 mg |
| QHL-097 | 1228.27 | 1228 | red solid powder | 157 mg |
| QHL-098 | 1229.26 | 1229 | red solid powder | 137 mg |
| QHL-099 | 1237.28 | 1237 | red solid powder | 49 mg |
| QHL-100 | 1272.33 | 1272 | red solid powder | 67 mg |
| QHL-101 | 1273.32 | 1273 | red solid powder | 71 mg |
| QHL-102 | 1281.34 | 1281 | red solid powder | 49 mg |
| QHL-103 | 1316.38 | 1316 | red solid powder | 86 mg |
| QHL-104 | 1317.37 | 1317 | red solid powder | 93 mg |
| QHL-105 | 1325.39 | 1325 | red solid powder | 37 mg |
| QHL-106 | 1404.48 | 1404 | red solid powder | 46 mg |
| QHL-107 | 1405.47 | 1405 | red solid powder | 158 mg |
| QHL-108 | 1413.49 | 1413 | red solid powder | 102 mg |
| QHL-109 | 1184.17 | 1184 | red solid powder | 34 mg |
| QHL-110 | 1185.16 | 1185 | red solid powder | 28 mg |
| QHL-111 | 1193.18 | 1193 | red solid powder | 38 mg |
| QHL-112 | 1170.14 | 1170 | red solid powder | 31 mg |
| QHL-113 | 1171.13 | 1171 | red solid powder | 104 mg |
| QHL-114 | 1179.15 | 1179 | red solid powder | 170 mg |
| QHL-115 | 1226.25 | 1226 | red solid powder | 118 mg |
| QHL-116 | 1227.24 | 1227 | red solid powder | 100 mg |
| QHL-117 | 1235.26 | 1235 | red solid powder | 224 mg |
| QHL-118 | 1212.22 | 1212 | red solid powder | 167 mg |
| QHL-119 | 1213.21 | 1213 | red solid powder | 102 mg |
| QHL-120 | 1221.23 | 1221 | red solid powder | 81 mg |
| QHL-121 | 1163.18 | 1163 | red solid powder | 106 mg |
| QHL-122 | 1177.22 | 1177 | red solid powder | 97 mg |
| QHL-123 | 1205.28 | 1205 | red solid powder | 139 mg |
| QHL-124 | 1219.31 | 1219 | red solid powder | 76 mg |
| QHL-125 | 1219.31 | 1219 | red solid powder | 143 mg |
| QHL-126 | 1237.34 | 1237 | red solid powder | 125 mg |
| QHL-127 | 1239.3 | 1239 | red solid powder | 136 mg |
| QHL-128 | 1278.33 | 1278 | red solid powder | 121 mg |
| QHL-129 | 1193.22 | 1193 | red solid powder | 64 mg |
| QHL-130 | 1207.25 | 1207 | red solid powder | 184 mg |
| QHL-131 | 1209.28 | 1209 | red solid powder | 164 mg |
| QHL-132 | 1269.32 | 1269 | red solid powder | 144 mg |
| QHL-133 | 1220.25 | 1220 | red solid powder | 104 mg |
| QHL-134 | 1234.28 | 1234 | red solid powder | 95 mg |
| QHL-135 | 1234.32 | 1234 | red solid powder | 164 mg |
| QHL-136 | 1262.33 | 1262 | red solid powder | 182 mg |
| QHL-137 | 1243.29 | 1243 | red solid powder | 155 mg |

The disclosure also provides the following comparative compounds, the structural formula is as follows:

Compound C1
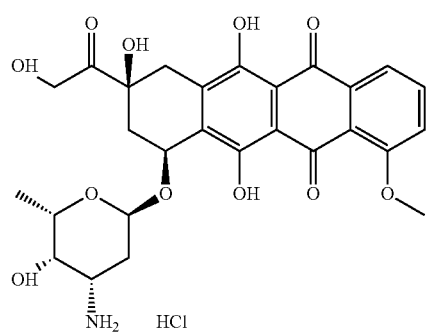
Doxorubicin
Compound C2
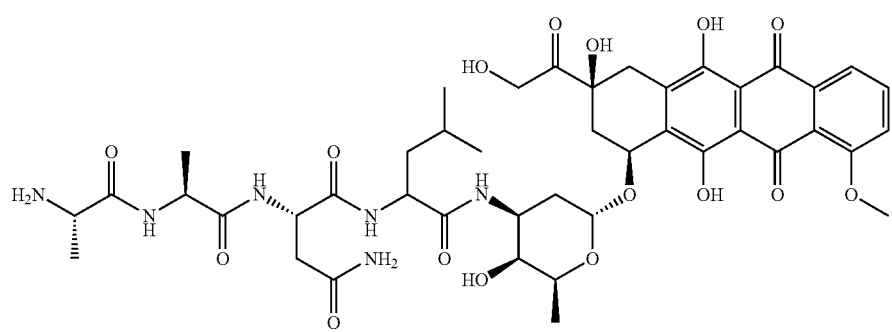
AANL-DOX
Compound C3
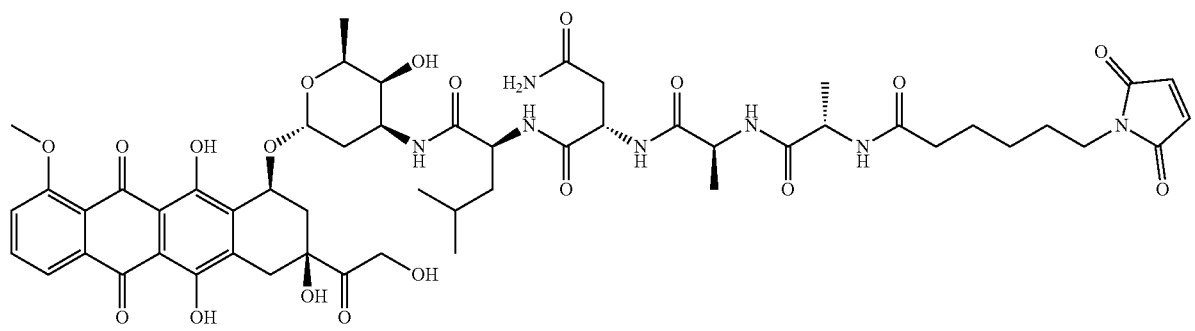
EMC-AANL-Doxorubicin
Compound C4
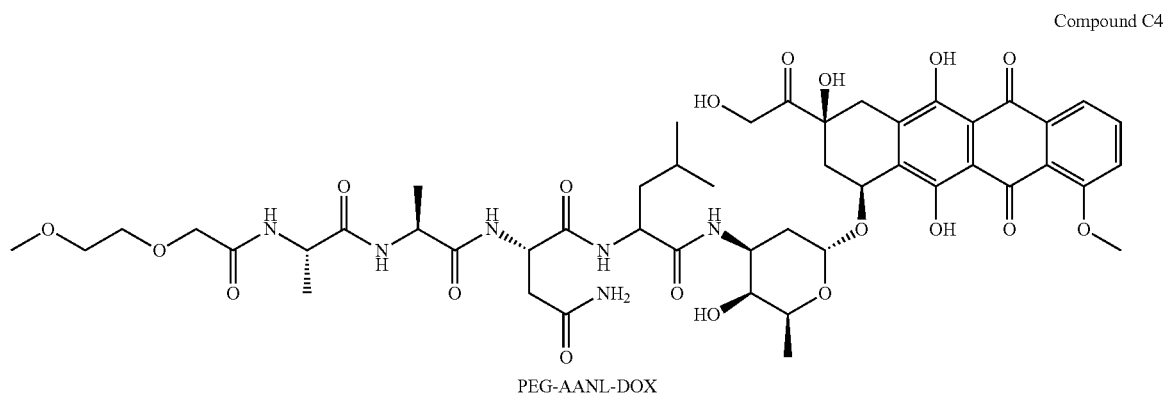
PEG-AANL-DOX Example 6: Comparison of the Water Solubility of the Adriamycin Derivative of the Present Invention and a Control Compound Compounds of QHL-001~QHL-137 prepared in the examples of the present invention, Compounds and the reference compounds C1, C2, C3 and C4 prepared above were freeze-dried (−70° C.). Compounds were dissolved in water with different concentration to check water solubility by observation and HPLC test (>95%).

TABLE 3

Screening drug solubility test

| Compound number | S1 | S2 | S3 | A | Solubility |
|---|---|---|---|---|---|
| C1: DOX | / | / | / | | <1 mg/ml |
| C2: AANL-DOX | / | / | / | Leu | <1 mg/ml |
| C3: EMC-AANL-DOX | $C_6$—COOH | / | / | Leu | <5 mg/ml |
| C4: PEG-AANL-DOX | / | 1peg | / | Leu | <5 mg/ml |
| QHL-001 | / | 2peg | / | PABC-$NH_2$ | >10 mg/ml |
| QHL-002 | / | 3peg | / | PABC-$NH_2$ | >10 mg/ml |
| QHL-003 | / | 4peg | / | PABC-$NH_2$ | >15 mg/ml |
| QHL-004 | / | 6peg | / | PABC-$NH_2$ | >20 mg/ml |
| QHL-005 | / | 2peg | / | PABC-OH | >10 mg/ml |
| QHL-006 | / | 3peg | / | PABC-OH | >10 mg/ml |
| QHL-007 | / | 4peg | / | PABC-OH | >15 mg/ml |
| QHL-008 | / | 6peg | / | PABC-OH | >20 mg/ml |
| QHL-009 | / | 2peg | / | Leu | >10 mg/ml |
| QHL-010 | / | 3peg | / | Leu | >10 mg/ml |
| QHL-011 | / | 4peg | / | Leu | >15 mg/ml |
| QHL-012 | / | 6peg | / | Leu | >20 mg/ml |
| QHL-013 | / | 2peg | Glu | PABC-$NH_2$ | >20 mg/ml |
| QHL-014 | / | 3peg | Glu | PABC-$NH_2$ | >20 mg/ml |
| QHL-015 | / | 4peg | Glu | PABC-$NH_2$ | >25 mg/ml |
| QHL-016 | / | 6peg | Glu | PABC-$NH_2$ | >30 mg/ml |
| QHL-017 | / | 2peg | Glu | PABC-OH | >20 mg/ml |
| QHL-018 | / | 3peg | Glu | PABC-OH | >20 mg/ml |
| QHL-019 | / | 4peg | Glu | PABC-OH | >25 mg/ml |
| QHL-020 | / | 6peg | Glu | PABC-OH | >30 mg/ml |
| QHL-021 | / | 2peg | Glu | Leu | >20 mg/ml |
| QHL-022 | / | 3peg | Glu | Leu | >20 mg/ml |
| QHL-023 | / | 4peg | Glu | Leu | >25 mg/ml |
| QHL-024 | / | 6peg | Glu | Leu | >30 mg/ml |
| QHL-025 | / | 2peg | ASP | PABC-$NH_2$ | >20 mg/ml |
| QHL-026 | / | 3peg | ASP | PABC-$NH_2$ | >20 mg/ml |
| QHL-027 | / | 4peg | ASP | PABC-$NH_2$ | >25 mg/ml |
| QHL-028 | / | 6peg | ASP | PABC-$NH_2$ | >30 mg/ml |
| QHL-029 | / | 2peg | ASP | PABC-OH | >20 mg/ml |
| QHL-030 | / | 3peg | ASP | PABC-OH | >20 mg/ml |
| QHL-031 | / | 4peg | ASP | PABC-OH | >25 mg/ml |
| QHL-032 | / | 6peg | ASP | PABC-OH | >30 mg/ml |
| QHL-033 | / | 2peg | ASP | Leu | >20 mg/ml |
| QHL-034 | / | 3peg | ASP | Leu | >20 mg/ml |
| QHL-035 | / | 4peg | ASP | Leu | >25 mg/ml |
| QHL-036 | / | 6peg | ASP | Leu | >30 mg/ml |
| QHL-037 | $C_2$—COOH | 2peg | Glu | PABC-$NH_2$ | >20 mg/ml |
| QHL-038 | $C_2$—COOH | 2peg | Glu | PABC-OH | >20 mg/ml |
| QHL-039 | $C_2$—COOH | 2peg | Glu | Leu | >20 mg/ml |
| QHL-040 | $C_2$—COOH | 2peg | ASP | PABC-$NH_2$ | >20 mg/ml |
| QHL-041 | $C_2$—COOH | 2peg | ASP | PABC-OH | >20 mg/ml |
| QHL-042 | $C_2$—COOH | 2peg | ASP | Leu | >20 mg/ml |
| QHL-043 | $C_2$—COOH | 3peg | Glu | PABC-$NH_2$ | >20 mg/ml |
| QHL-044 | $C_2$—COOH | 3peg | Glu | PABC-OH | >20 mg/ml |
| QHL-045 | $C_2$—COOH | 3peg | Glu | Leu | >20 mg/ml |
| QHL-046 | $C_2$—COOH | 3peg | ASP | PABC-$NH_2$ | >20 mg/ml |
| QHL-047 | $C_2$—COOH | 3peg | ASP | PABC-OH | >20 mg/ml |
| QHL-048 | $C_2$—COOH | 3peg | ASP | Leu | >20 mg/ml |
| QHL-049 | $C_2$—COOH | 4peg | Glu | PABC-$NH_2$ | >25 mg/ml |
| QHL-050 | $C_2$—COOH | 4peg | Glu | PABC-OH | >25 mg/ml |
| QHL-051 | $C_2$—COOH | 4peg | Glu | Leu | >25 mg/ml |
| QHL-052 | $C_2$—COOH | 4peg | ASP | PABC-$NH_2$ | >25 mg/ml |
| QHL-053 | $C_2$—COOH | 4peg | ASP | PABC-OH | >25 mg/ml |
| QHL-054 | $C_2$—COOH | 4peg | ASP | Leu | >25 mg/ml |
| QHL-055 | $C_2$—COOH | 6peg | Glu | PABC-$NH_2$ | >25 mg/ml |
| QHL-056 | $C_2$—COOH | 6peg | Glu | PABC-OH | >25 mg/ml |
| QHL-057 | $C_2$—COOH | 6peg | Glu | Leu | >25 mg/ml |
| QHL-058 | $C_2$—COOH | 6peg | ASP | PABC-$NH_2$ | >25 mg/ml |
| QHL-059 | $C_2$—COOH | 6peg | ASP | PABC-OH | >25 mg/ml |
| QHL-060 | $C_2$—COOH | 6peg | ASP | Leu | >25 mg/ml |
| QHL-061 | $C_3$—COOH | 2peg | Glu | PABC-$NH_2$ | >15 mg/ml |
| QHL-062 | $C_3$—COOH | 2peg | Glu | PABC-OH | >15 mg/ml |
| QHL-063 | $C_3$—COOH | 2peg | Glu | Leu | >15 mg/ml |
| QHL-064 | $C_3$—COOH | 2peg | ASP | PABC-$NH_2$ | >15 mg/ml |
| QHL-065 | $C_3$—COOH | 2peg | ASP | PABC-OH | >15 mg/ml |
| QHL-066 | $C_3$—COOH | 2peg | ASP | Leu | >15 mg/ml |
| QHL-067 | $C_3$—COOH | 3peg | Glu | PABC-$NH_2$ | >15 mg/ml |
| QHL-068 | $C_3$—COOH | 3peg | Glu | PABC-OH | >15 mg/ml |
| QHL-069 | $C_3$—COOH | 3peg | Glu | Leu | >25 mg/ml |
| QHL-070 | $C_3$—COOH | 3peg | ASP | PABC-$NH_2$ | >25 mg/ml |
| QHL-071 | $C_3$—COOH | 3peg | ASP | PABC-OH | >25 mg/ml |
| QHL-072 | $C_3$—COOH | 3peg | ASP | Leu | >25 mg/ml |
| QHL-073 | $C_3$—COOH | 4peg | Glu | PABC-$NH_2$ | >25 mg/ml |
| QHL-074 | $C_3$—COOH | 4peg | Glu | PABC-OH | >25 mg/ml |
| QHL-075 | $C_3$—COOH | 4peg | Glu | Leu | >25 mg/ml |
| QHL-076 | $C_3$—COOH | 4peg | ASP | PABC-$NH_2$ | >25 mg/ml |
| QHL-077 | $C_3$—COOH | 4peg | ASP | PABC-OH | >25 mg/ml |
| QHL-078 | $C_3$—COOH | 4peg | ASP | Leu | >25 mg/ml |
| QHL-079 | $C_3$—COOH | 6peg | Glu | PABC-$NH_2$ | >25 mg/ml |
| QHL-080 | $C_3$—COOH | 6peg | Glu | PABC-OH | >25 mg/ml |
| QHL-081 | $C_3$—COOH | 6peg | Glu | Leu | >30 mg/ml |
| QHL-082 | $C_3$—COOH | 6peg | ASP | PABC-$NH_2$ | >30 mg/ml |
| QHL-083 | $C_3$—COOH | 6peg | ASP | PABC-OH | >30 mg/ml |
| QHL-084 | $C_3$—COOH | 6peg | ASP | Leu | >30 mg/ml |
| QHL-085 | $C_2$—COOH | 2peg | / | PABC-$NH_2$ | >10 mg/ml |
| QHL-086 | $C_2$—COOH | 2peg | / | PABC-OH | >15 mg/ml |
| QHL-087 | $C_2$—COOH | 2peg | / | Leu | >10 mg/ml |
| QHL-088 | $C_2$—COOH | 3peg | / | PABC-$NH_2$ | >10 mg/ml |
| QHL-089 | $C_2$—COOH | 3peg | / | PABC-OH | >15 mg/ml |
| QHL-090 | $C_2$—COOH | 3peg | / | Leu | >10 mg/ml |
| QHL-091 | $C_2$—COOH | 4peg | / | PABC-$NH_2$ | >20 mg/ml |
| QHL-092 | $C_2$—COOH | 4peg | / | PABC-OH | >25 mg/ml |
| QHL-093 | $C_2$—COOH | 4peg | / | Leu | >20 mg/ml |
| QHL-094 | $C_2$—COOH | 6peg | / | PABC-$NH_2$ | >20 mg/ml |
| QHL-095 | $C_2$—COOH | 6peg | / | PABC-OH | >20 mg/ml |
| QHL-096 | $C_2$—COOH | 6peg | / | Leu | >20 mg/ml |
| QHL-097 | $C_3$—COOH | 2peg | / | PABC-$NH_2$ | >20 mg/ml |
| QHL-098 | $C_3$—COOH | 2peg | / | PABC-OH | >10 mg/ml |
| QHL-099 | $C_3$—COOH | 2peg | / | Leu | >20 mg/ml |
| QHL-100 | $C_3$—COOH | 3peg | / | PABC-$NH_2$ | >25 mg/ml |
| QHL-101 | $C_3$—COOH | 3peg | / | PABC-OH | >20 mg/ml |
| QHL-102 | $C_3$—COOH | 3peg | / | Leu | >10 mg/ml |
| QHL-103 | $C_3$—COOH | 4peg | / | PABC-$NH_2$ | >15 mg/ml |
| QHL-104 | $C_3$—COOH | 4peg | / | PABC-OH | >20 mg/ml |
| QHL-105 | $C_3$—COOH | 4peg | / | Leu | >10 mg/ml |
| QHL-106 | $C_3$—COOH | 6peg | / | PABC-$NH_2$ | >20 mg/ml |
| QHL-107 | $C_3$—COOH | 6peg | / | PABC-OH | >25 mg/ml |
| QHL-108 | $C_3$—COOH | 6peg | / | Leu | >20 mg/ml |
| QHL-109 | $C_3$—COOH | / | Glu | PABC-$NH_2$ | >10 mg/ml |
| QHL-110 | $C_3$—COOH | / | Glu | PABC-OH | >15 mg/ml |
| QHL-111 | $C_3$—COOH | / | Glu | Leu | >10 mg/ml |
| QHL-112 | $C_3$—COOH | / | ASP | PABC-$NH_2$ | >10 mg/ml |
| QHL-113 | $C_3$—COOH | / | ASP | PABC-OH | >15 mg/ml |
| QHL-114 | $C_3$—COOH | / | ASP | Leu | >15 mg/ml |
| QHL-115 | $C_6$—COOH | / | Glu | PABC-$NH_2$ | >10 mg/ml |
| QHL-116 | $C_6$—COOH | / | Glu | PABC-OH | >15 mg/ml |
| QHL-117 | $C_6$—COOH | / | Glu | Leu | >10 mg/ml |
| QHL-118 | $C_6$—COOH | / | ASP | PABC-$NH_2$ | >15 mg/ml |
| QHL-119 | $C_6$—COOH | / | ASP | PABC-OH | >15 mg/ml |
| QHL-120 | $C_6$—COOH | / | ASP | Leu | >10 mg/ml |
| QHL-121 | $C_6$—COOH | / | Gly | Leu | >10 mg/ml |
| QHL-122 | $C_6$—COOH | / | Ala | Leu | >10 mg/ml |
| QHL-123 | $C_6$—COOH | / | Val | Leu | >2 mg/ml |
| QHL-124 | $C_6$—COOH | / | Leu | Leu | >5 mg/ml |
| QHL-125 | $C_6$—COOH | / | Ile | Leu | >2 mg/ml |
| QHL-126 | $C_6$—COOH | / | Met | Leu | >2 mg/ml |
| QHL-127 | $C_6$—COOH | / | Phe | Leu | >10 mg/ml |

TABLE 3-continued

Screening drug solubility test

| Compound number | S1 | S2 | S3 | A | Solubility |
|---|---|---|---|---|---|
| QHL-128 | C$_6$—COOH | / | Trp | Leu | >2 mg/ml |
| QHL-129 | C$_6$—COOH | / | Ser | Leu | >5 mg/ml |
| QHL-130 | C$_6$—COOH | / | Thr | Leu | >2 mg/ml |
| QHL-131 | C$_6$—COOH | / | Cys | Leu | >10 mg/ml |
| QHL-132 | C$_6$—COOH | / | Tyr | Leu | >2 mg/ml |
| QHL-133 | C$_6$—COOH | / | Asn | Leu | >2 mg/ml |
| QHL-134 | C$_6$—COOH | / | Gln | Leu | >5 mg/ml |
| QHL-135 | C$_6$—COOH | / | Lys | Leu | >5 mg/ml |
| QHL-136 | C$_6$—COOH | / | Arq | Leu | >2 mg/ml |
| QHL-137 | C$_6$—COOH | / | His | Leu | >5 mg/ml |

Example 7: Chemical Modified Linker is Selected to Acquire High Activation Efficiency Comparing with the native peptide sequence linker by cleaved by Legumain, The S-C-A is a chemical modified linker and shows high activation efficiency. When the C selected AAN, The activation of different S-C-A linker and control linker was evaluated in the activation assay, The S-C-A conjugate was used to dissolve and they were diluted for ten times to a concentration of 0.1 mM/ml. At 37° C., sample compounds were added into 100 μg acidized human breast cancer (MDA-MB435) tumor tissue homogenates (pH6.0) in a concentration of 1 mg/ml. The enzyme in tumor tissue homogenates could release and detected by HPLC, thereby comparing the activation efficiency of the linker by the tumor tissue. Results were showed in table 4.

TABLE 4-1

Activation efficiency of the linker by the tumor tissue

| | S | | | | Activation |
|---|---|---|---|---|---|
| | S1 | S2 | S3 | A | (%) |
| C2: AANL-DOX | / | / | / | | 42.1 |
| C3: EMC-AANL-DOX | C$_6$—COOH | / | / | | 56.4 |
| QHL-087 | C$_2$—COOH | 2peg | / | Leu | 96.4 |
| QHL-090 | C$_2$—COOH | 3peg | / | Leu | 93.4 |
| QHL-093 | C$_2$—COOH | 4peg | / | Leu | 90.1 |
| QHL-096 | C$_2$—COOH | 6peg | / | Leu | 82.6 |

In same cleaving condition, 2 or 3 peg linker has higher Activation rate than others.

TABLE 4-2

Activation efficiency of the linker by the tumor tissue

| | S | | | | Activation |
|---|---|---|---|---|---|
| Compound name | S1 | S2 | S3 | A | (%) |
| Control compound | / | Peg | / | PABC-NH$_2$ | 66.9 |
| QHL-085 | C$_2$—COOH | 2peg | / | PABC-NH$_2$ | 93.5 |
| QHL-088 | C$_2$—COOH | 3peg | / | PABC-NH$_2$ | 99.6 |
| QHL-086 | C$_2$—COOH | 2peg | / | PABC-OH | 94.5 |
| QHL-089 | C$_2$—COOH | 3peg | / | PABC-OH | 98.6 |
| QHL-087 | C$_2$—COOH | 2peg | / | Leu | 82.4 |
| QHL-090 | C$_2$—COOH | 3peg | / | Leu | 93.4 |
| QHL-037 | C$_2$—COOH | 2peg | Glu | PABC-NH$_2$ | 76.1 |
| QHL-043 | C$_2$—COOH | 3peg | Glu | PABC-NH$_2$ | 88.4 |
| QHL-038 | C$_2$—COOH | 2peg | Glu | PABC-OH | 91.5 |
| QHL-044 | C$_2$—COOH | 3peg | Glu | PABC-OH | 92.4 |

TABLE 4-2-continued

Activation efficiency of the linker by the tumor tissue

| | S | | | | Activation |
|---|---|---|---|---|---|
| Compound name | S1 | S2 | S3 | A | (%) |
| QHL-039 | C$_2$—COOH | 2peg | Glu | Leu | 85.4 |
| QHL-045 | C$_2$—COOH | 3peg | Glu | Leu | 84.6 |

In same cleaving condition, PABC-OH linker has higher Activation rate than leu.

In same cleaving condition, 3peg+PABC-OH linker has highest activation rate.

Example 8: Study on Efficacy of C3 and Different Linker Compounds in Breast Cancer 4T1 Tumor Model Test purpose: to investigate the anti-tumor efficacy of QHL-086, QHL-087, QHL-092, QHL-095 in mice model for tumor treatment.

Test drug: QHL-086, QHL-087, QHL-092, QHL-095 and EMC-AANL-DOX injections and mitomycin injection, diluted to corresponding concentrations by physiological saline when testing.

Method and Results:

1. Animal: C57 mice of 6-8 weeks old, all female.
2. Production of tumor model 1) 4T1 tumor cells were purchased from American type culture collection (ATCC) and identified according the specification provided by ATCC. Cells were cultivated in DMEM culture solution containing 10% fetal bovine serum at 37° C. and 5% CO$_2$. The cells were passaged for every three days and cells within the 15th passage were used.

2) Production of tumor. 5×10$^6$ 4 T1 cells were subcutaneously injected to the back of the nude mice. Mice were randomly grouped after the tumor reached at least 100 mm$^3$. Then treatment began and the day on which the treatment began was day 1.

3) Course of Treatment

According to the clinical application of QHL-086, QHL-087, QHL-092, QHL-095 and EMC-AANL-DOX were intravenously injected (IV) in a same dose of 36 umol/kg. The control group was administered by physiological saline. Drugs were administered once weekly for 3 weeks.

4) Results and discussions: As shown in FIG. 1, the 2 PEG linker has better efficacy than other linker in 4T1 tumor model.

Example 9: Study on Efficacy of C3 and Different Linker Compounds in HT1080 Tumor Model Test purpose: to investigate the anti-tumor efficacy of QHL-086, QHL-092, QHL-095, QHL-087, QHL-010, QHL-117 in mice model for tumor treatment.

Test drug: C3, QHL-086, QHL-092, QHL-095, QHL-087, QHL-010, QHL-117 injections and mitomycin injection, diluted to corresponding concentrations by physiological saline when testing.

Method and Results:

1. Animal: nude mice of 6-8 weeks old, all female.
2. Production of tumor model

1) HT1080 cells were purchased from American type culture collection (ATCC) and identified according the specification provided by ATCC. Cells were cultivated in DMEM culture solution containing 10% fetal bovine serum at 37° C. and 5% $CO_2$. The cells were passaged for every three days and cells within the 15th passage were used.

2) Production of tumor. $5 \times 10^6$ HT1080 cells were subcutaneously injected to the back of the nude mice. Mice were randomly grouped after the tumor reached at least 100 $mm^3$. Then treatment began and the day on which the treatment began was day 1.

3) Course of Treatment

According to the clinical application of C3, QHL-086, QHL-092, QHL-095, QHL-087, QHL-010, QHL-117 were intravenously injected (IV). C3, QHL-086, QHL-092, QHL-095, QHL-087, QHL-010, QHL-117 were administered in a low and same dose of 18 umol/kg. The control group was administered by physiological saline. Drugs were administered once weekly for 3 weeks.

4) Grouping and test results are shown in Table 5. The PEG linker has better efficacy than EMC-AANL-DOX in HT1080 tumor model.

TABLE 5

C3, QHL-086, QHL-092, QHL-095, QHL-087, QHL-010, QHL-117, mitomycin and control group on tumor treatment in nude mice

| Group | Number of animal | Size of tumor ($mm^3$) Day 28 | inhibitory rate on tumor Day 28 |
|---|---|---|---|
| Saline | 6 | 1746.6 ± 673.4 | 0 |
| QHL-086 | 6 | 0 | 100% |
| QHL-092 | 6 | 0 | 100% |
| QHL-095 | 6 | 0 | 100% |
| QHL-087 | 6 | 0 | 100% |
| QHL-010 | 6 | 0 | 100% |
| QHL-117 | 6 | 0 | 100% |
| C1 DOX | 6 | 754.4 ± 587.4 | 56.8% |
| C2 AANL-DOX | 6 | 318.5 ± 197.6 | 81.8% |
| C3 EMC-AANL-DOX | 6 | 138.3 ± 124.6 | 92.1% |
| C4 PEG-AANL-DOX | 6 | 548.4 ± 153.1 | 68.6% |

Example 10: Study on Efficacy of Some Compounds of the Invention Injections on Human Liver Cancer HepG2 Cells in Nude Mice Test purpose: to investigate the anti-tumor efficacy of some compounds of the invention in mice model for tumor treatment.

Test drug: QHL-095, QHL-008, QHL-086, QHL-116, QHL-119, QHL-092, QHL-006, QHL-089, QHL-005, QHL-007, QHL-096, QHL-012, QHL-087, QHL-117, QHL-120, QHL-093, QHL-010, QHL-090, QHL-009, QHL-011 injections and control group injection, diluted to corresponding concentrations by physiological saline when testing.

Method and Results:
1. Animal: nude mice of 6-8 weeks old, all female.
2. Production of tumor model
1) Human liver cancer HepG2 cells were purchased from American type culture collection (ATCC) and identified according the specification provided by ATCC. Cells were cultivated in DMEM culture solution containing 10% fetal bovine serum at 37° C. and 5% $CO_2$. The cells were passaged for every three days and cells within the 15th passage were used.
2) Production of tumor. $5 \times 10^6$ HegG2 cells were subcutaneously injected to the back of the nude mice. Mice were randomly grouped after the tumor reached at least 100 $mm^3$. Then treatment began and the day on which the treatment began was day 1.

3) Course of Treatment

According to the clinical application of QHL-095, QHL-008, QHL-086, QHL-116, QHL-119, QHL-092, QHL-006, QHL-089, QHL-005, QHL-007, QHL-096, QHL-012, QHL-087, QHL-117, QHL-120, QHL-093, QHL-010, QHL-090, QHL-009, QHL-011, drugs were intravenously injected (IV). Compounds and control groups were administered in a dose of 54 umol/kg. The control group was administered by physiological saline. Drugs were administered once weekly for four weeks.

4) Grouping and test results are shown in Table 6.

TABLE 6

Effect of some compounds of the invention, and control groups on tumor treatment in nude mice

| Group | Number of animal | Size of tumor ($mm^3$) Day 28 | inhibitory rate on tumor Day 28 |
|---|---|---|---|
| Saline | 6 | 2897.9 ± 1948.6 | 0 |
| QHL-095 | 6 | 208.7 ± 164.7 | 92.8% |
| QHL-008 | 6 | 148.1 ± 84.6 | 94.9% |
| QHL-086 | 6 | 0 | 100% |
| QHL-116 | 6 | 0 | 100% |
| QHL-119 | 6 | 292.68 ± 196.80 | 89.9% |
| QHL-092 | 6 | 69.5 ± 46.7 | 97.6% |
| QHL-006 | 6 | 0 | 100% |
| QHL-089 | 6 | 0 | 100% |
| QHL-005 | 6 | 0 | 100% |
| QHL-007 | 6 | 148.1 ± 84.6 | 94.9% |
| QHL-096 | 6 | 0 | 100% |
| QHL-012 | 6 | 197.4 ± 104.5 | 93.2% |
| QHL-087 | 6 | 0 | 100% |
| QHL-117 | 6 | 0 | 100% |
| QHL-120 | 6 | 208.1 ± 164.8 | 92.8% |
| QHL-093 | 6 | 168.49 ± 98.4 | 94.2% |
| QHL-010 | 6 | 0 | 100% |
| QHL-090 | 6 | 0 | 100% |
| QHL-009 | 6 | 0 | 100% |
| QHL-011 | 6 | 98.1 ± 48.4 | 96.6% |
| C1 DOX | 6 | 1683.4 ± 1087.4 | 41.9% |
| C2 AANL-DOX | 6 | 1564 ± 689.4 | 46.0% |
| C3 EMC-AANL-DOX | 6 | 218.3 ± 167.7 | 92.5% |
| C4 PEG-AANL-DOX | 6 | 548.7 ± 347.5 | 81.1% |

5) Results and discussions: As shown in Table 6, inhibition on tumor growth by compounds of the invention were greatly improved as compared with the control groups by using the same molar dosage.

Example 11: Study on Tissue Distribution of QHL-087 and EMC-AANL-DOX in Orthotopic Transplantation CT26 Tumor in Liver Test purpose: to investigate active drug tissue distribution of liver tumor.

Animal: BALB/c mice of 6-8 weeks old, all female.

Production of tumor model: CT26 tumor cells were purposed from ATCC. Cells were cultivated in DMEM culture solution containing 10% fetal bovine serum at 37° C. and 5% $CO_2$. The cells were passaged for every three days and cells within the 15th passage were used.

Figure 2:
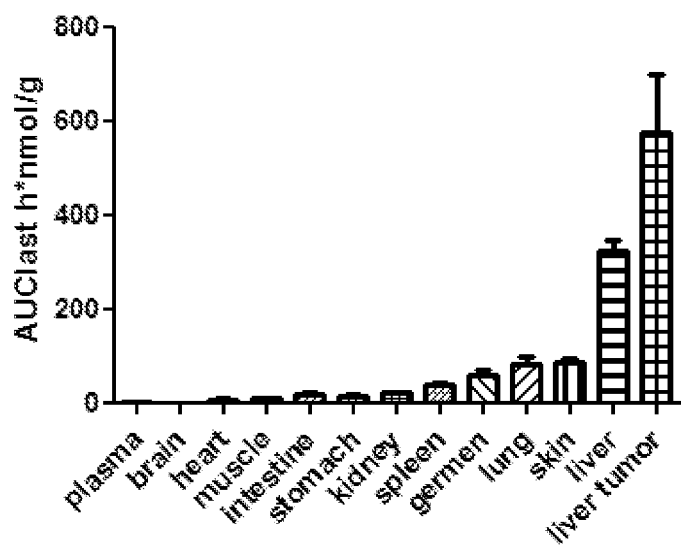
FIG. 2: The tissue distribution of EMC-AANL-DOX in orthotopic transplantation tumor in liver.
Figure 3:
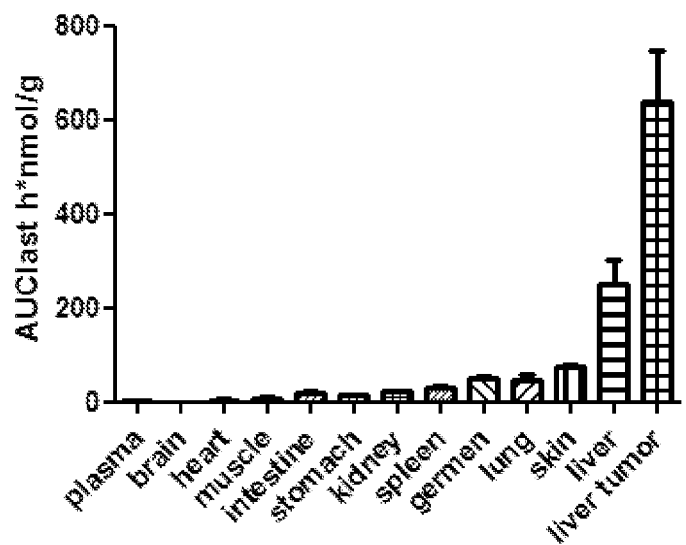
FIG. 3: The tissue distribution of S3 in orthotopic transplantation tumor in liver.

$5 \times 10^5$ CT26 cancer cells were subcutaneously injected to the back of the nude mice. Mice were randomly grouped after the tumor reached 800-1000 $mm^3$. Then extract the tumor tissue and cleave to 100 mm3 tumor tissue block and orthotopic transplant into BALB/c mice liver. After 14 days, when orthotopic transplantation tumor grow up, 36 mice with orthotopic transplantation tumor for a group are treated with drug. Then collect the different tissue at 1, 6, 12, 24, 36, 72 hr to detect the concentration of releasing doxorubicin in different tissue. The $AUC_{last}$h*nmol/g were calculated and shown in FIG. 2, FIG. 3 in mean and SEM. Results and discussions: As shown in FIG. 2 and FIG. 3. the active doxorubicine distribute of QHL-087 and EMC-AANL-DOX are major in orthotopic tumor in liver.

Example 12: Study of QHL-087 in Orthotopic Transplantation CT26 Tumor in Liver Test purpose: to investigate efficacy of QHL-087, PD-1 and combination in orthotopic transplantation CT26 tumor.

Test drug: QHL-087 in 18 umol/kg, mouse PD-1 in 5 mg/kg

Animal: BALB/c mice of 6-8 weeks old, all female.

Figure 4:
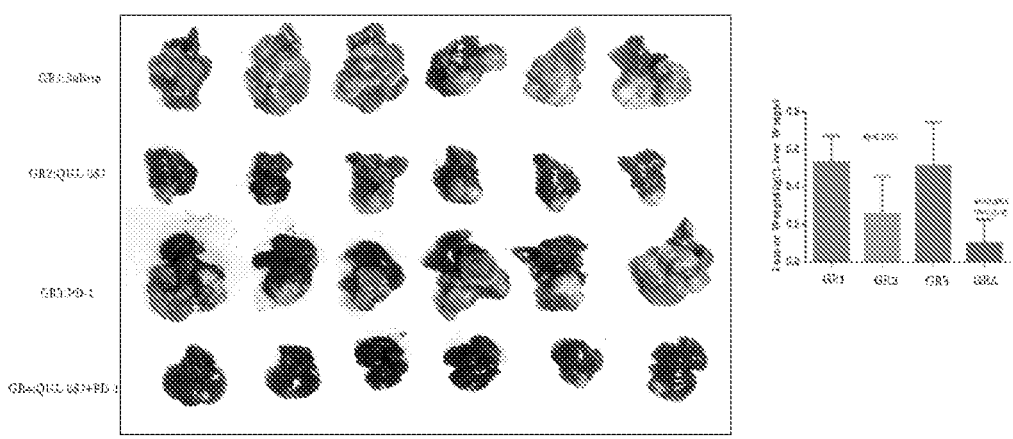
FIG. 4: The efficacy of EMC-AANL-DOX in orthotopic transplantation tumor in liver.

Production of tumor model: CT26 tumor cells were purposed from ATCC. Cells were cultivated in DMEM culture solution containing 10% fetal bovine serum at 37° C. and 5% $CO_2$. The cells were passaged for every three days and cells within the 15th passage were used. $5\times10^5$ CT26 cancer cells were subcutaneously injected to the back of the nude mice. Mice were randomly grouped after the tumor reached 800-1000 $mm^3$. Then extract the tumor tissue and cleave to 100 mm3 tumor tissue block and orthotopic transplant into BALB/c mice liver. After one week, when orthotopic transplantation tumor grow up, Mice with orthotopic transplantation tumor were randomly grouped. 6 mice for one group are treated with drug. The treatment began and the day on which the treatment began was day 1. According to the clinical application of QHL-087, drugs were intravenously injected (IV) once weekly for 3 weeks. Mouse PD-1 antibody were intravenously injected (IV) twice weekly for 3 weeks. Grouping and test results are shown in FIG. 4.

Results and discussions: As shown in FIG. 4, the single agent of QHL-087 have a great effect in inhibition the tumor growth. QHL-087+PD-1 show a better efficacy comparing with QHL-087 or PD-1 single agent.

Example 13: Study on Efficacy of Different Compounds in CT26 Tumor Immune Model Test purpose: to investigate the anti-tumor efficacy of different compounds in CT26 cancer model for immune treatment.

Test drug: QHL-096, QHL-087, QHL-090, QHL-093, QHL-117 and controls, all used in 18 μmol/kg; mouse PD-1 antibody, 5 mg/kg.

Animal: BALB/c mice of 6-8 weeks old, all female.

Production of Tumor Model:

1) CT26 tumor cells were purposed from ATCC. Cells were cultivated in DMEM culture solution containing 10% fetal bovine serum at 37° C. and 5% $CO_2$. The cells were passaged for every three days and cells within the 15th passage were used.

2) $5\times10^5$ CT26 cancer cells were subcutaneously injected to the back of the nude mice. Mice were randomly grouped after the tumor reached at least 100 $mm^3$ Then treatment began and the day on which the treatment began was day 1.

3) Analysis on tumor CD8+ T cells. The tumor tissue was homogenated and individual cells in the tumor were filtered, separated and washed by buffer twice, then cultivated with the leucocyte common antigen CD45-PE and CD8-FITC marked antibodies for 1 hour at ambient temperature. The cells were washed by phosphate buffer containing 1% fetal bovine serum twice and then analyzed for the ratio of the T lymphocyte antigen (CD8) positive cells in the leucocyte common antigen (CD45) positive cells by flow cytometry. Increasement of the ratio indicates increased T lymphocyte cells and thus the animal immunity against the tumor was improved.

5) Grouping and test results are shown in Table 7.

TABLE 7

Effect on inhibition of tumor and immune activation of different compounds and control

| Group | Number of animal | Size of tumor ($mm^3$) Day 28 | inhibitory rate on tumor % Day 18 | CD8:CD45 (%) |
|---|---|---|---|---|
| Saline | 6 | 1887.6 ± 646.8 | 0 | 5.2 |
| PD-1 | 6 | 1574.6 ± 474.5 | 16.6% | 6.1 |
| C3 EMC-AANL-DOX | | 624.5 ± 313.6 | 66.9% | 8.9 |
| QHL-096 | 6 | 347.7 ± 207.1 | 81.6% | 11.8 |
| QHL-087 | 6 | 214.8 ± 134.2 | 88.6% | 12.5 |
| QHL-090 | 6 | 335.7 ± 257.8 | 82.2% | 15.2 |
| QHL-093 | 6 | 323.7 ± 242.8 | 82.9% | 11.3 |
| QHL-117 | 6 | 306.4 ± 197.8 | 83.8% | 9.5 |
| C3 + PD-1 | 6 | 74.3 ± 45.8 | 96.1% | 11.7 |
| QHL-096 + PD-1 | 6 | 44.3 ± 25.6 | 97.7% | 18.4 |
| QHL-087 + PD-1 | 6 | 0 | 100% | 19.7 |
| QHL-090 + PD-1 | 6 | 0 | 100% | 21.7 |
| QHL-093 + PD-1 | 6 | 0 | 100% | 18.4 |
| QHL-117 + PD-1 | 6 | 64.6 ± 42.6 | 96.6% | 20.2 |

6) Results and discussion. Treatment effects of these compounds above combined with PD-1 were greatly improved as compared to the single agent group, and C3+PD-1 treatment groups. They show an excellent synergistic effect in promoting PD-1 effect in a low dosage.

Example 14: Study on Efficacy of QHL-087 Injection in Multiple Tumor Models

Test purpose: to investigate the anti-tumor spectrum of S3 through multiple tumor models from mice Test drug: QHL-087 injection, diluted to corresponding concentrations by physiological saline when testing.

Method and Results:

1. Animal: nude mice of 6-8 weeks old, all female.

2. Production of tumor model

1) Corresponding tumor cells were purchased from American type culture collection (ATCC) and identified according the specification provided by ATCC. Cells were cultivated in DMEM culture solution containing 10% fetal bovine serum at 37° C. and 5% $CO_2$. The cells were passaged for every three days and cells within the 15th passage were used.

2) Production of tumor. $5\times10^6$ corresponding cells were subcutaneously injected to the back of the nude mice. Mice were randomly grouped after the tumor reached at least 100 $mm^3$. Then treatment began and the day on which the treatment began was day 1.

3) Course of treatment. According to the clinical application of S3, S3 was administered in a dose of 36 umol/kg. The control group was administered by physiological saline. Animals were administered once weekly for three weeks.

4) Grouping and test results are shown in Table 9

TABLE 8

Treatment effect of QHL-087 in multiple tumor models

| Group | Tumor cell | inhibitory rate on tumor (Day 26) |
|---|---|---|
| Human breast cancer | MDA-MB435 | 91.5% |
| Human ovarian cancer | SK-OV-3 | 78.7% |
| Human colon cancer | HT-29 | 85.3% |
| Human chronic leukemia | K562 | 79.4% |
| Human colon caner | HT1080 | 90.5% |
| Human pancreatic cancer | Panc-1 | 75.7% |
| Human non-small cell lung cancer | A549 | 75.8% |
| Human renal cancer | OS-RC-2 | 87.4% |

5) Results and discussion. QHL-087 shows an excellent efficacy in multiple tumor models, demonstrating that the drug has a wide anti-tumor spectrum.

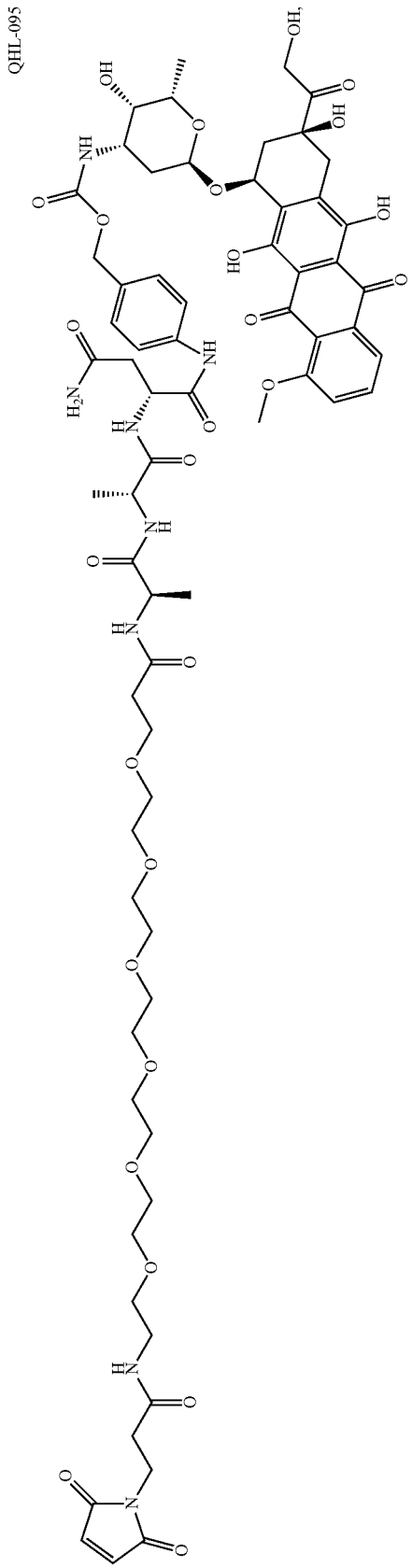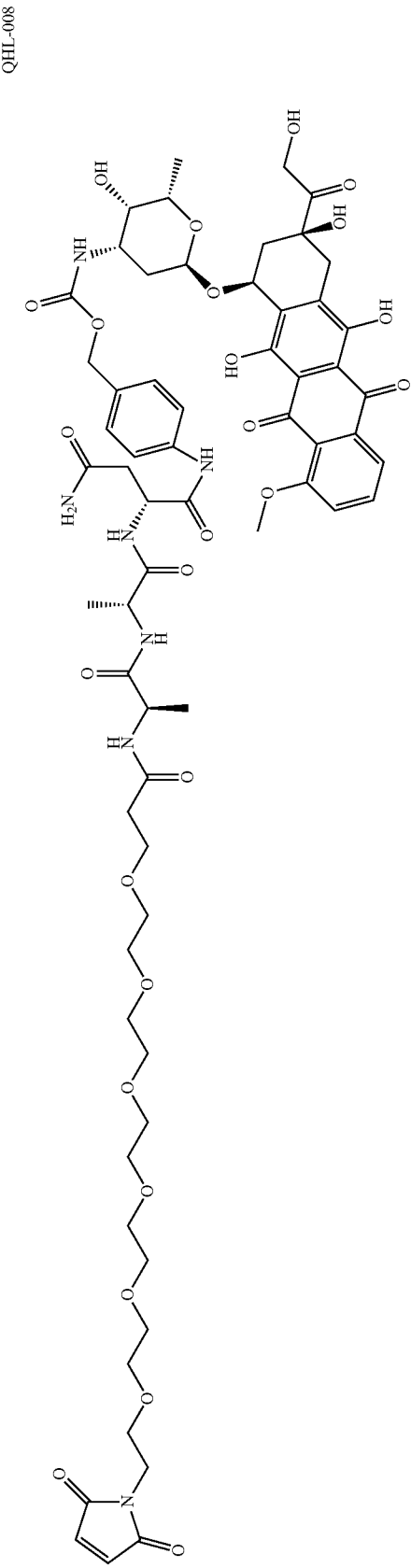

-continued
QHL-086
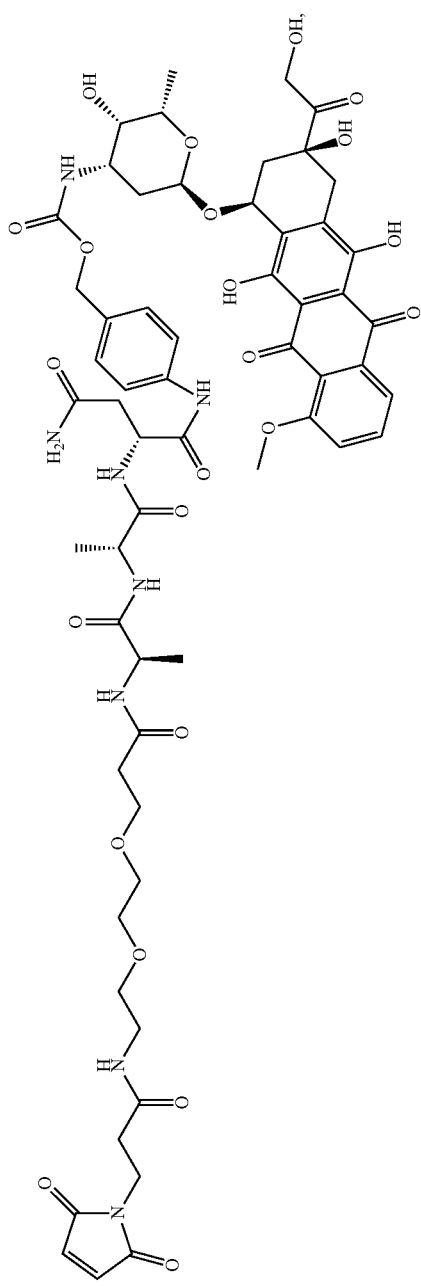
QHL-116
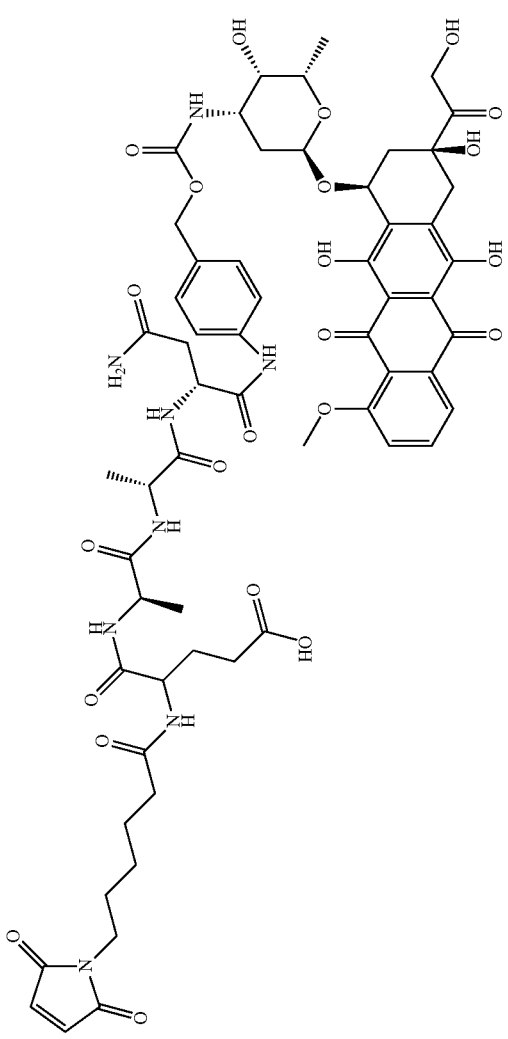

-continued
QHL-119
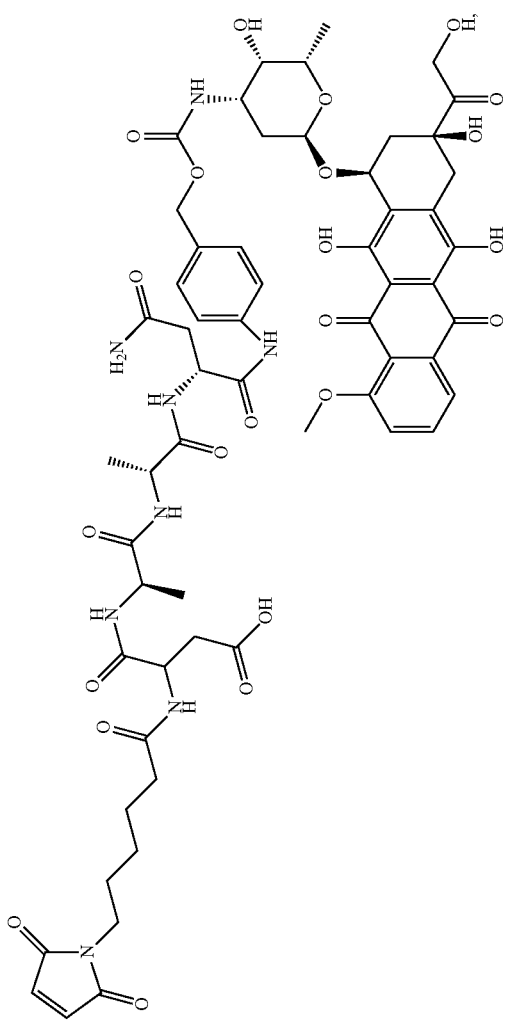
QHL-092
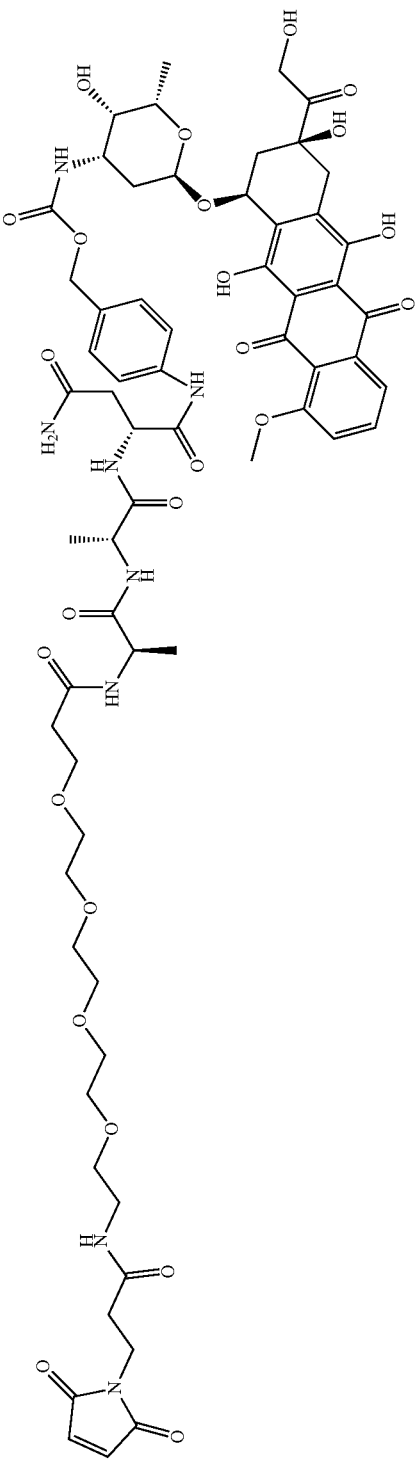

-continued
QHL-006
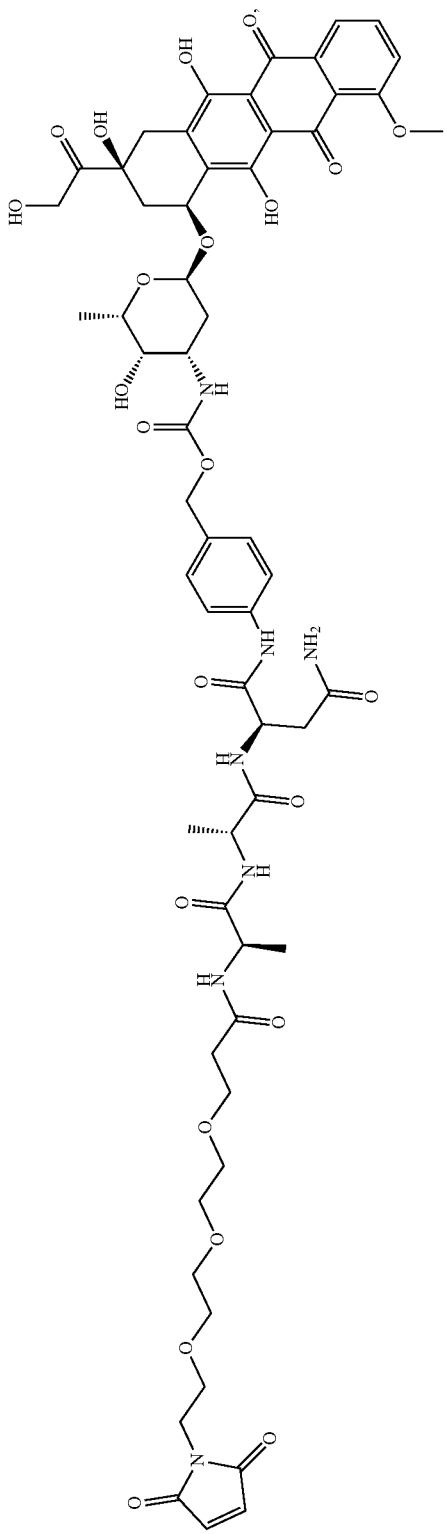
QHL-089
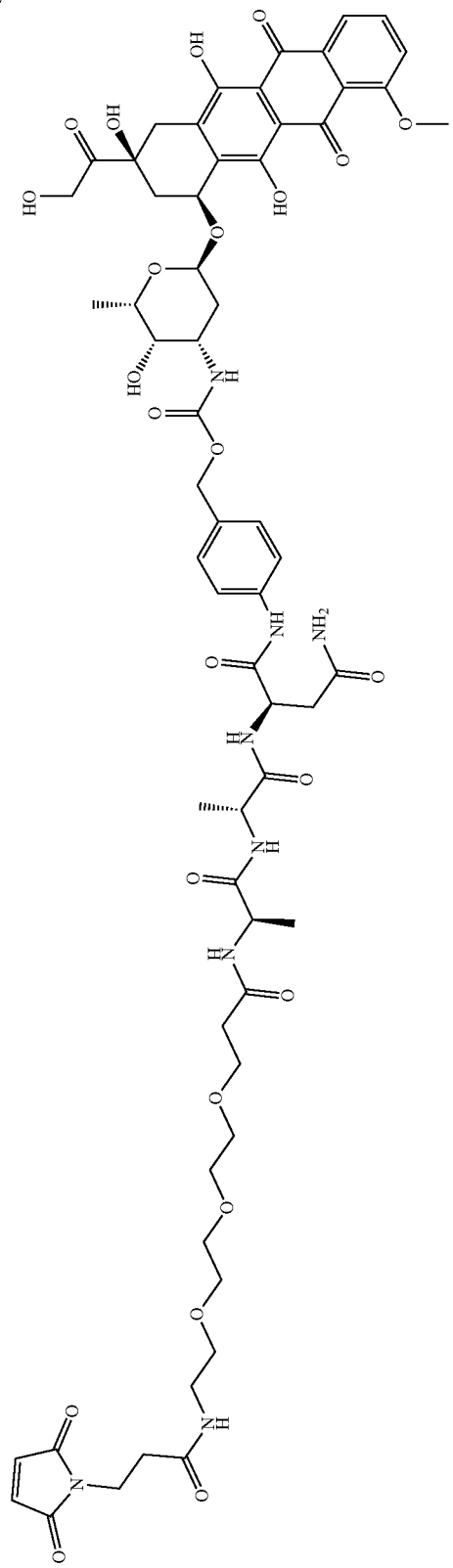

QHL-005
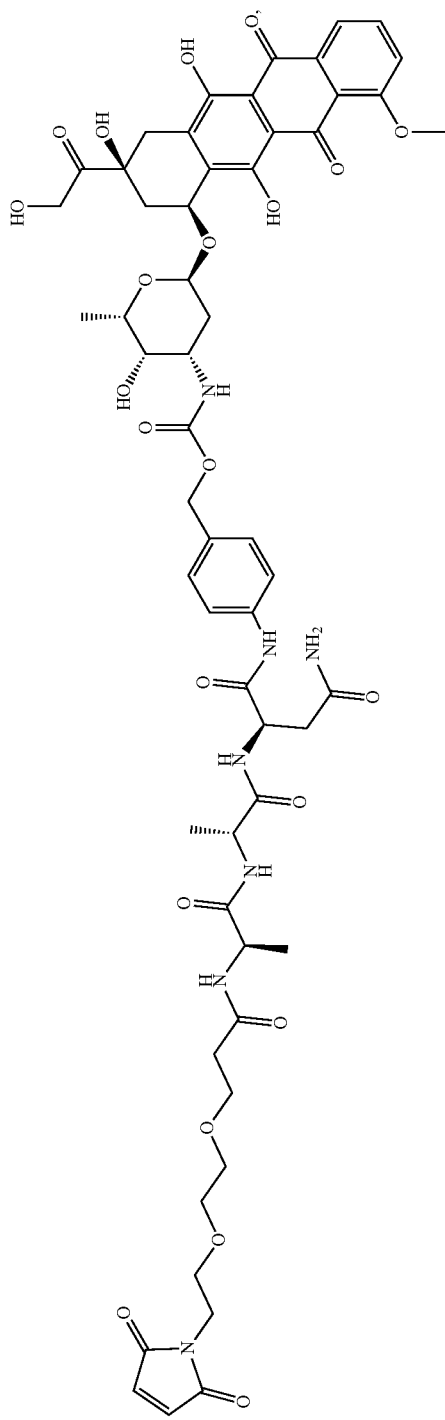
QHL-007
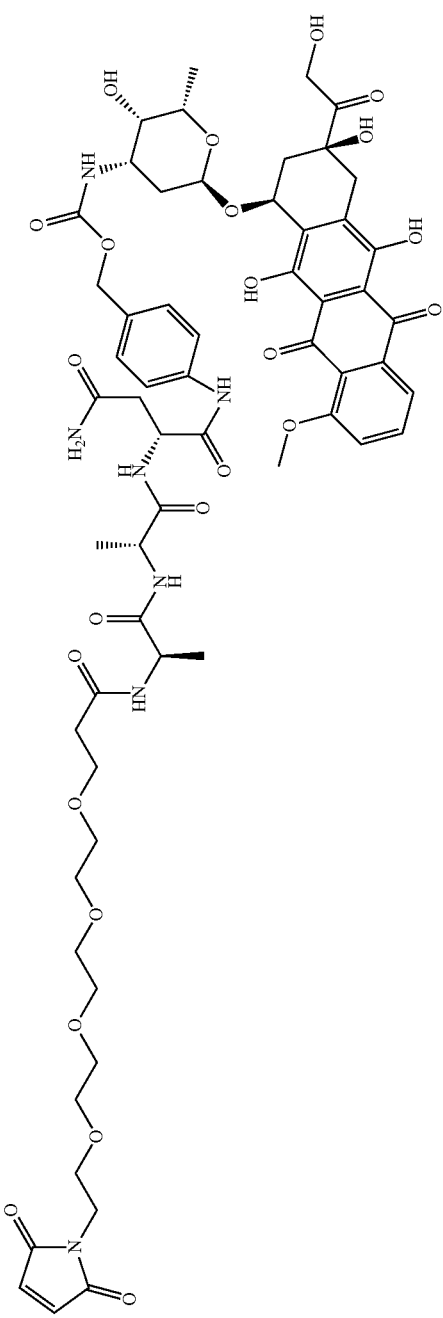

QHL-096
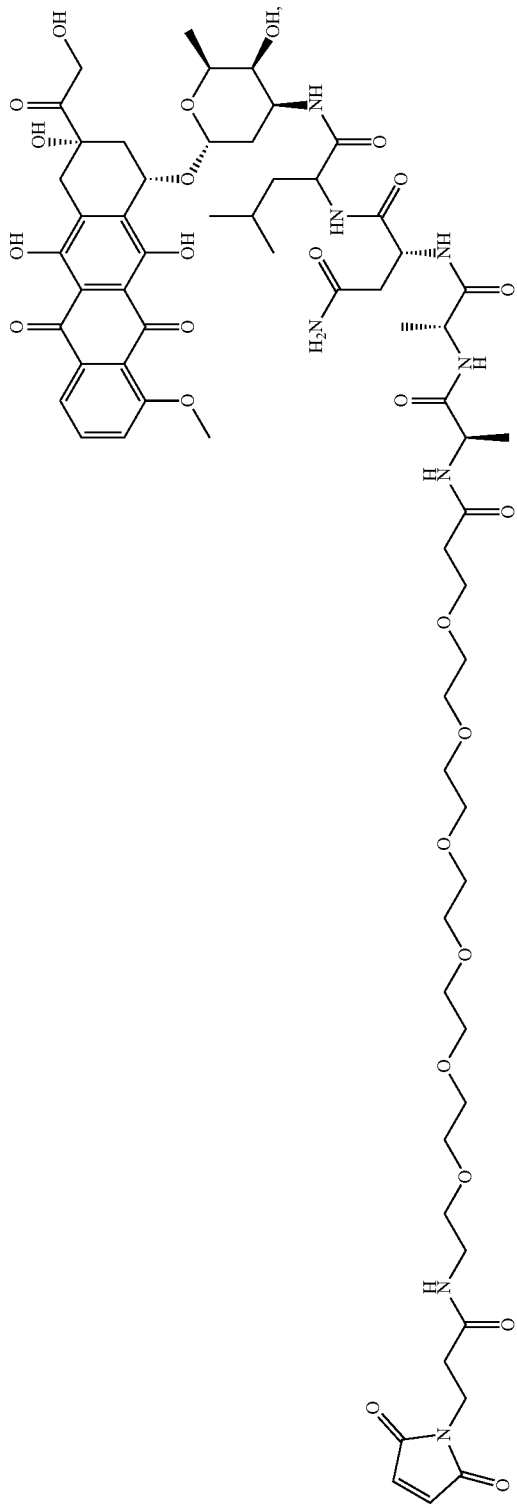
QHL-012
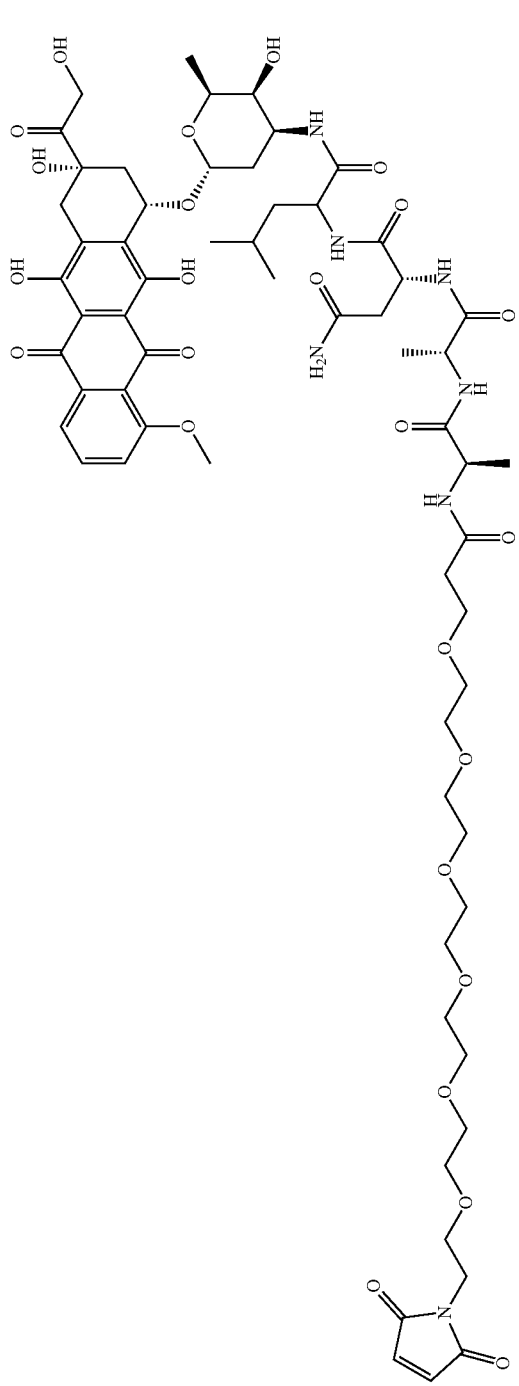

QHL-087
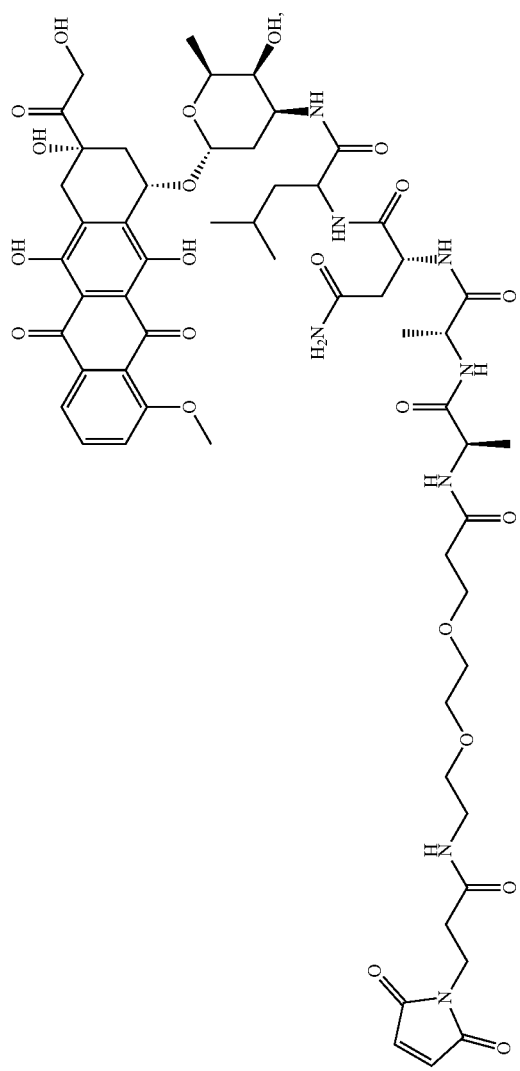

QHL-117
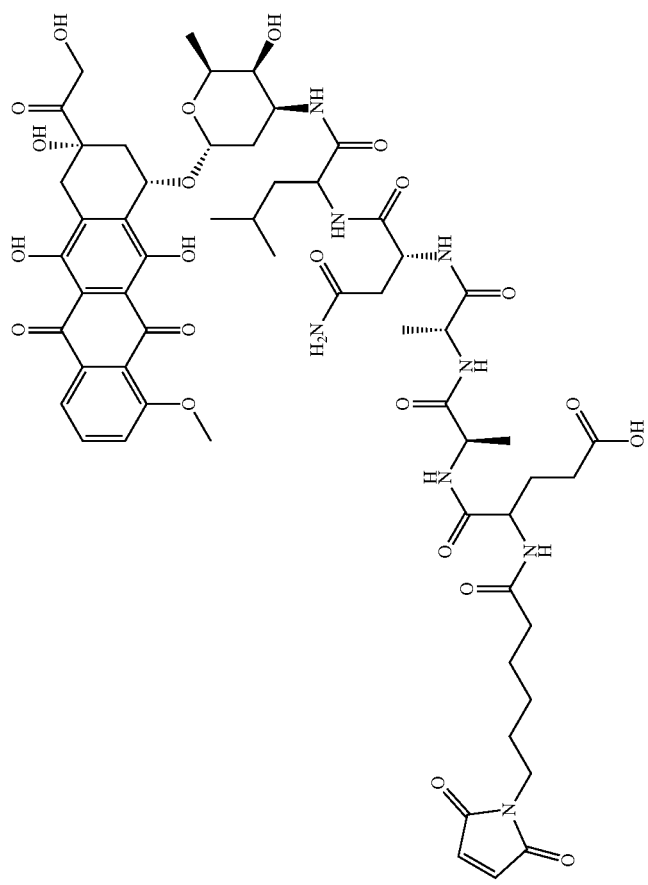

QHL-120
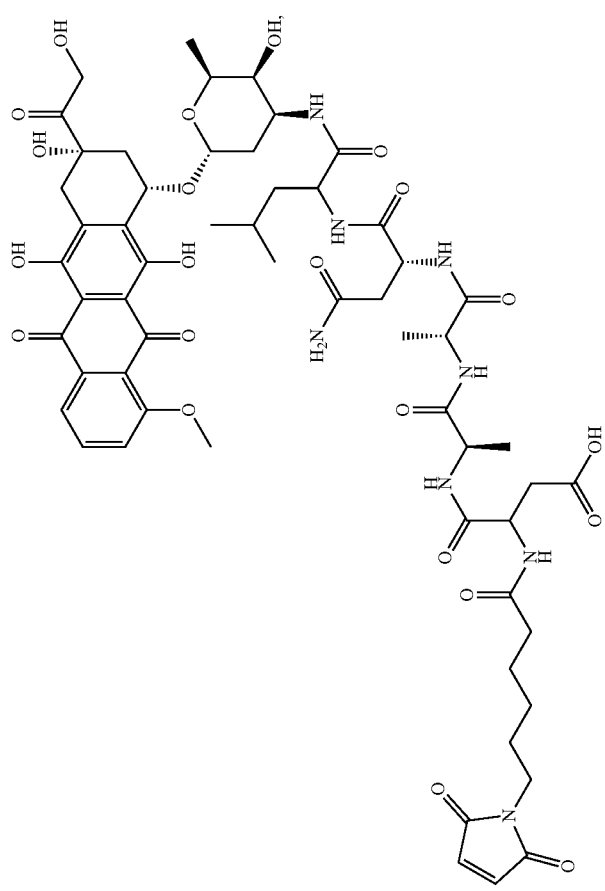

-continued
QHL-093
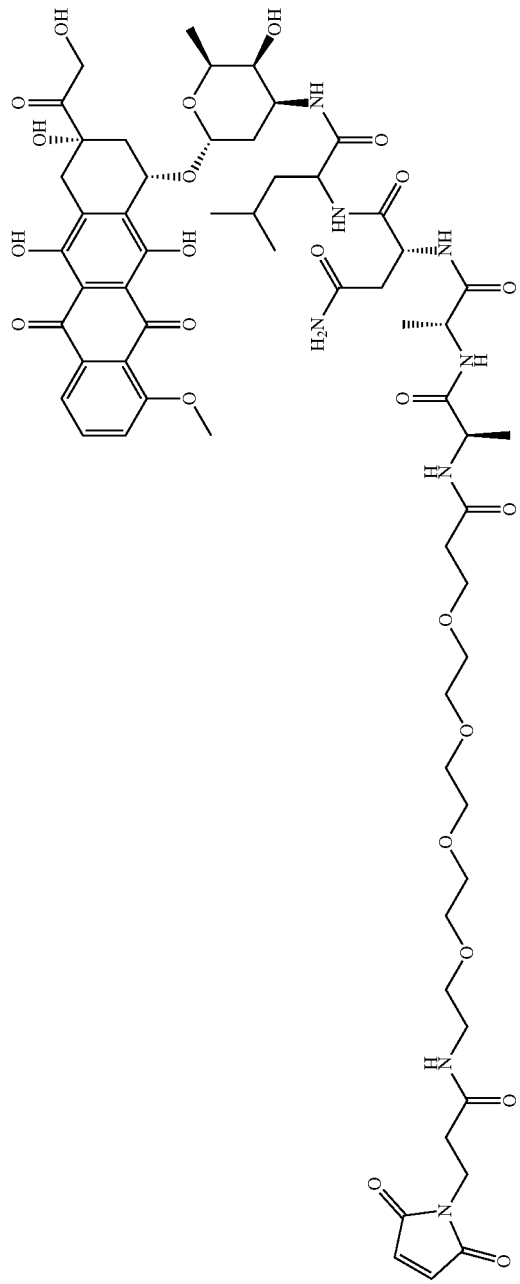
QHL-010
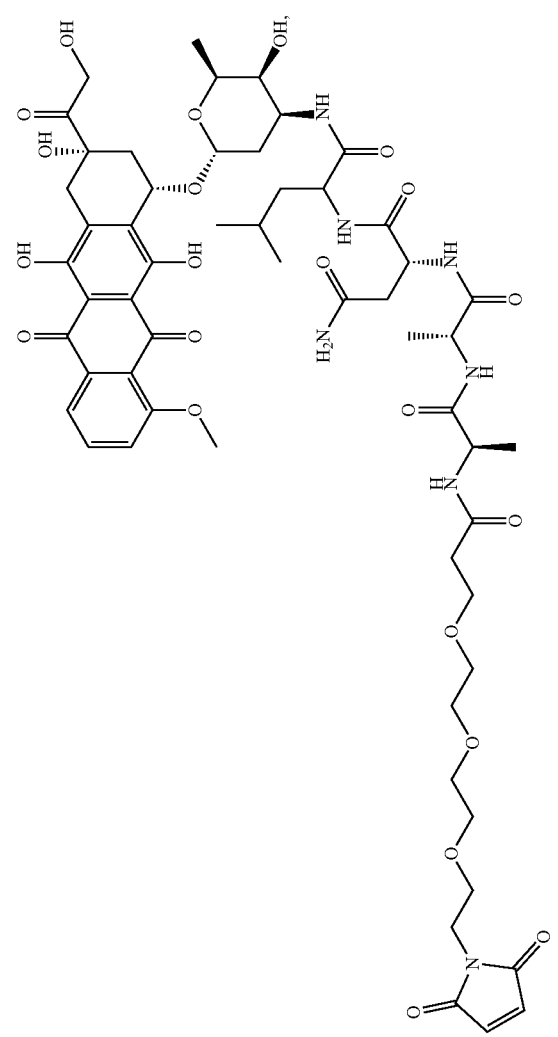

QHL-090
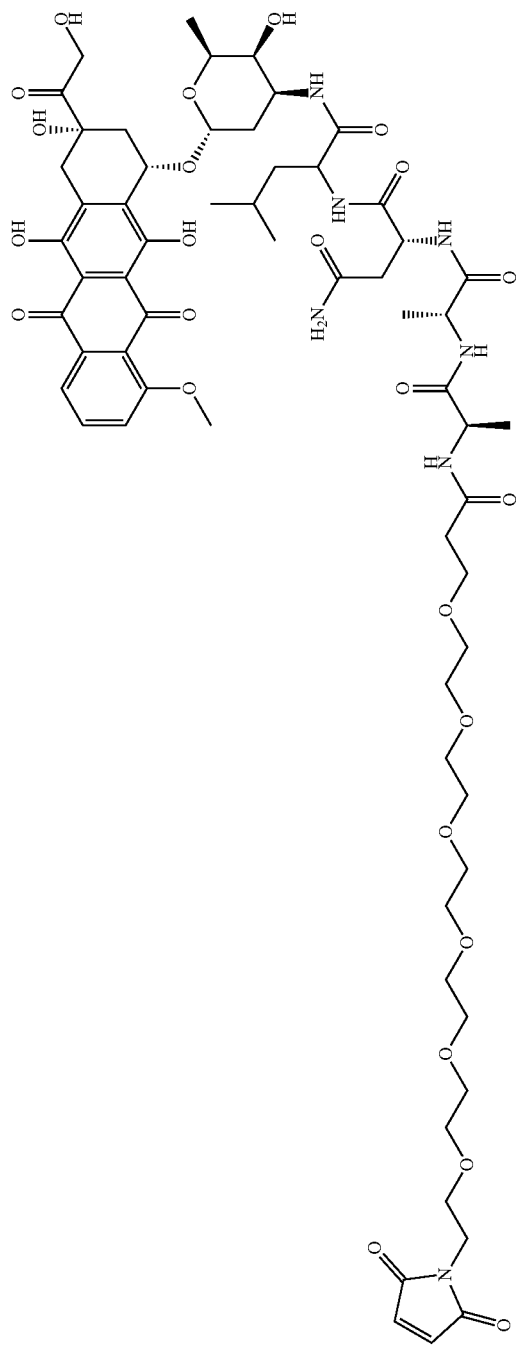
QHL-009
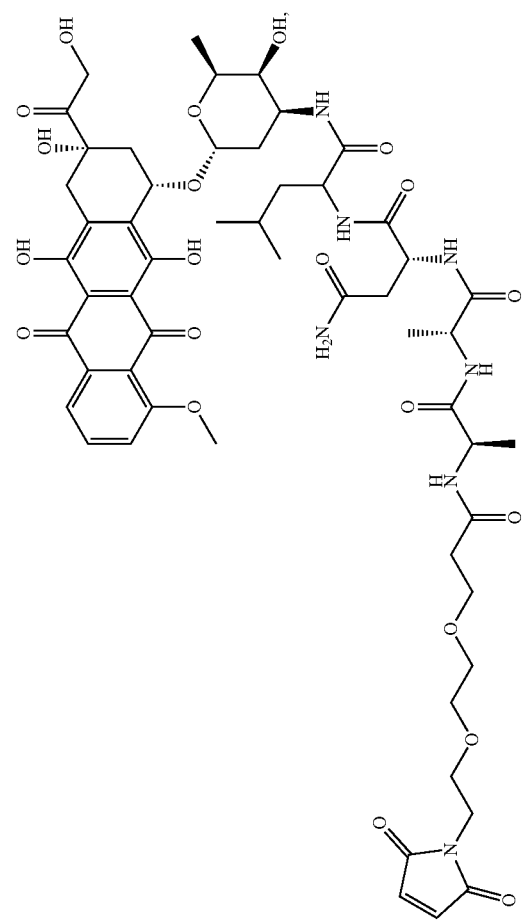

QHL-011
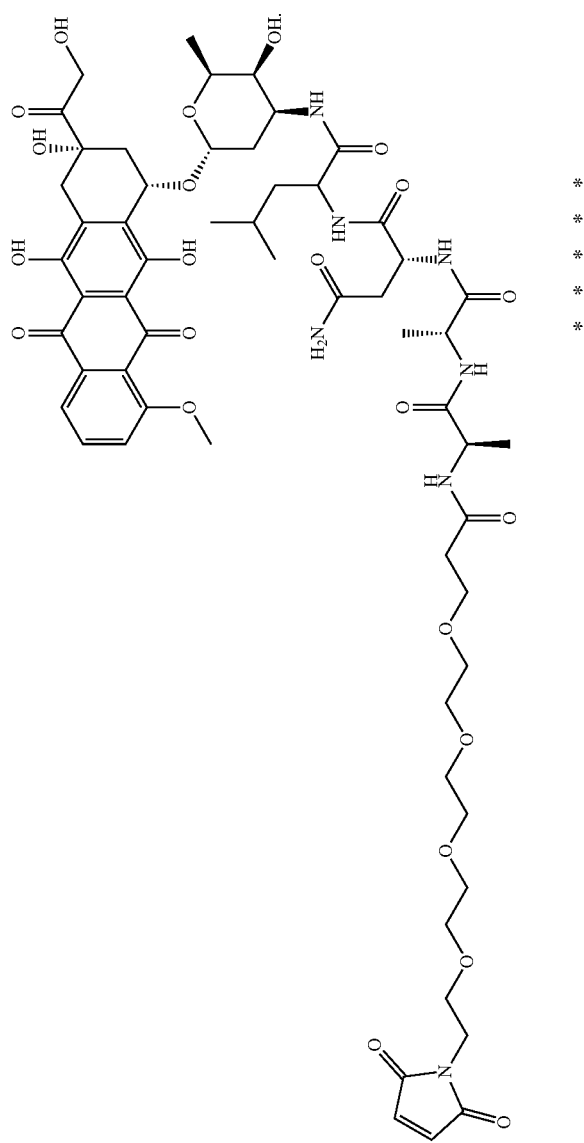

The invention claimed is:

1. A compound represented by the following formula I or a pharmaceutically acceptable salt thereof:

MI-S-C-A-D     (I)

wherein,

MI represents a maleimide group covalently coupled to plasma albumin;

S represents a selective group wherein the selective group improves the efficiency of enzyme digestion or selectivity;

C represents a cleaving group wherein the cleaving group is an amino acid linker that a proteolytic enzyme can break and wherein C is selected from the following group consisting of: Ala-Ala-Asn, Thr-Ala-Asn, Val-Ala-Asn, Asn-Ala-Asn, Thr-Thr-Asn, Val-Thr-Asn, Asn-Thr-Asn, Ala-Val-Asn, Thr-Val-Asn, Val-Val-Asn, Asn-Val-Asn, Ala-Ile-Asn, Thr-Ile-Asn, Val-Ile-Asn, Asn-Ile-Asn, Ala-Thr-Asn, D-Thr-L-Val-L-Asn, D-Thr-L-Ala-L-Asn, D-Ala-L-Val-L-Asn, L-Thr-D-Val-L-Asn, L-Thr-D-Ala-L-Asn, L-Ala-D-Val-L-Asn, D-Thr-D-Val-L-Asn, D-Thr-D-Ala-L-Asn, and D-Ala-D-Val-L-Asn;

A represents an auxiliary connecting arm; and

D is a Doxorubicin or Epirubicin.

2. The compound according to claim 1, characterized in that the MI is limited to a maleimide group

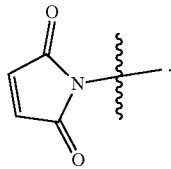 [SMILES: *N1C(=O)C=CC1=O]

3. The compound according to claim 1, wherein MI-S can be represented as:

MI-S1-S2-S3-S4 wherein S1 is selected from the group consisting of:

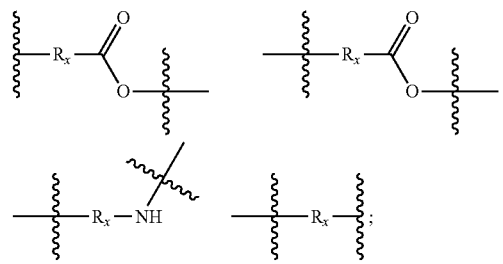

Rx is absent or selected from the group consisting of: $C_{1-6}$ alkyl, $C_{1-6}$ alkylamino, and $C_{1-6}$ alkylcarboxy;

S2 is absent or is selected from the group consisting of:

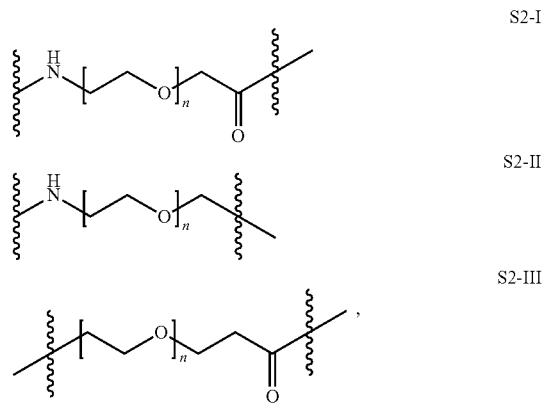

wherein n is an integer from 1 to 15;

S3 is absent or is selected from the group consisting of: Glutamic acid (Glu), aspartic acid (Asp), serine (Ser), threonine (Thr), cystine (Cys), tyrosine (Tyr), aspartic acid (Asn), and glutamic acid Glycine (Gln); and S4 can be represented by a structure selected from the group consisting of:

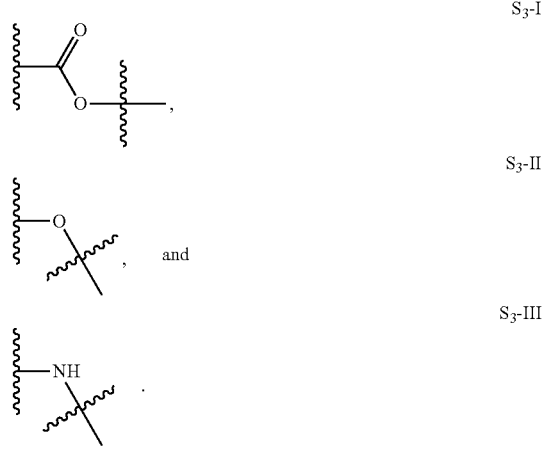

4. The compound according to claim 3, wherein MI-S is selected from:

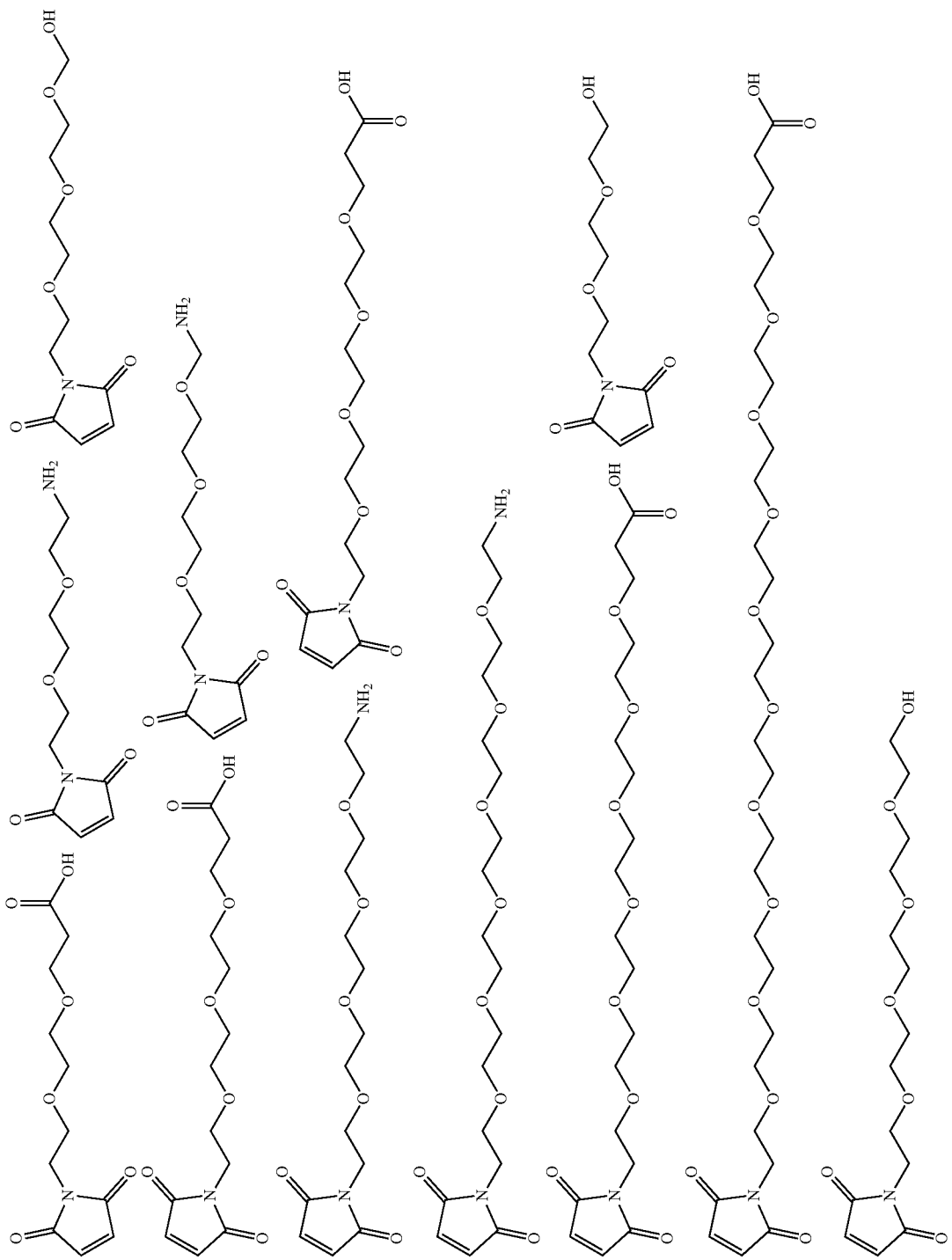

-continued
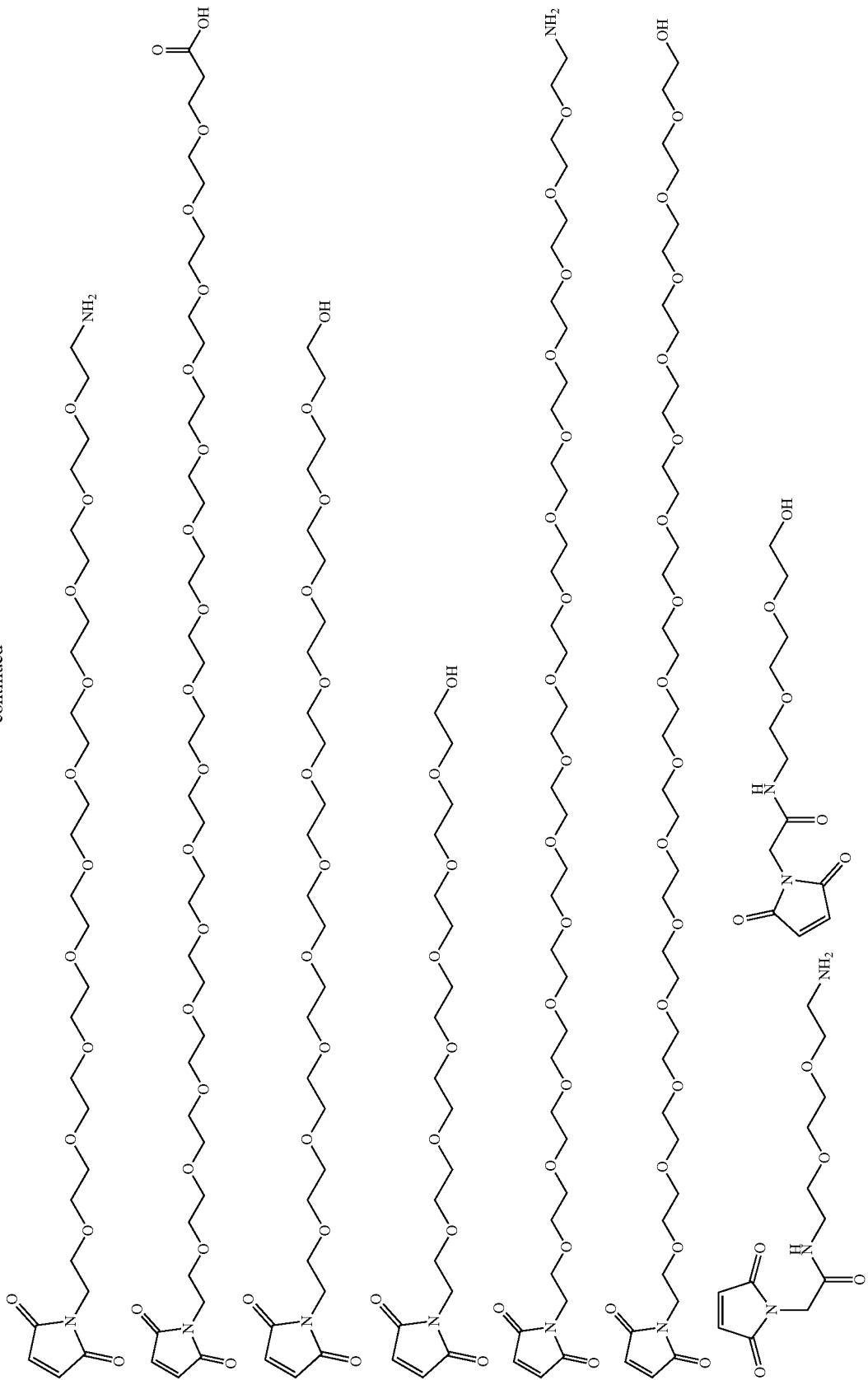

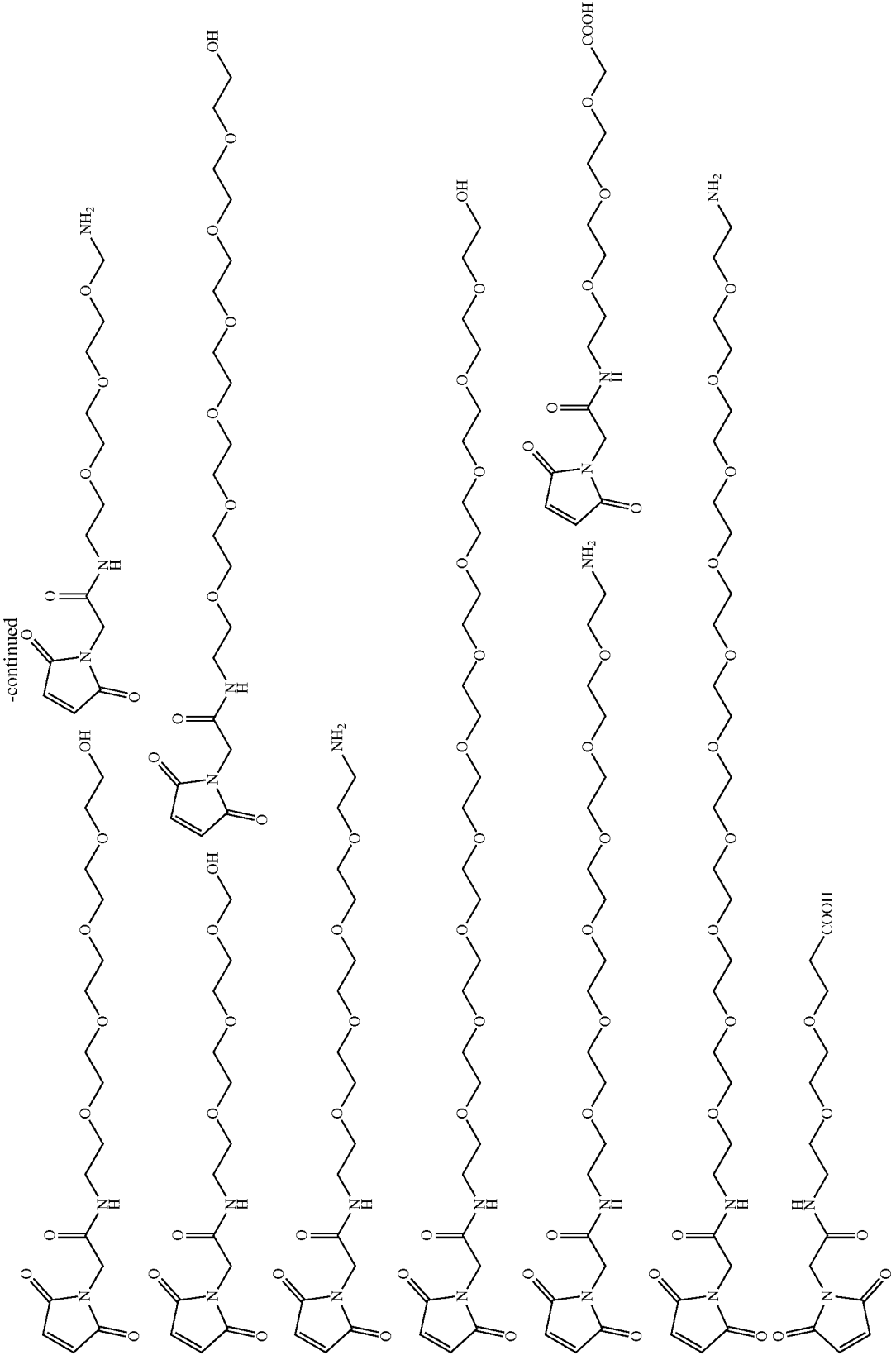

-continued
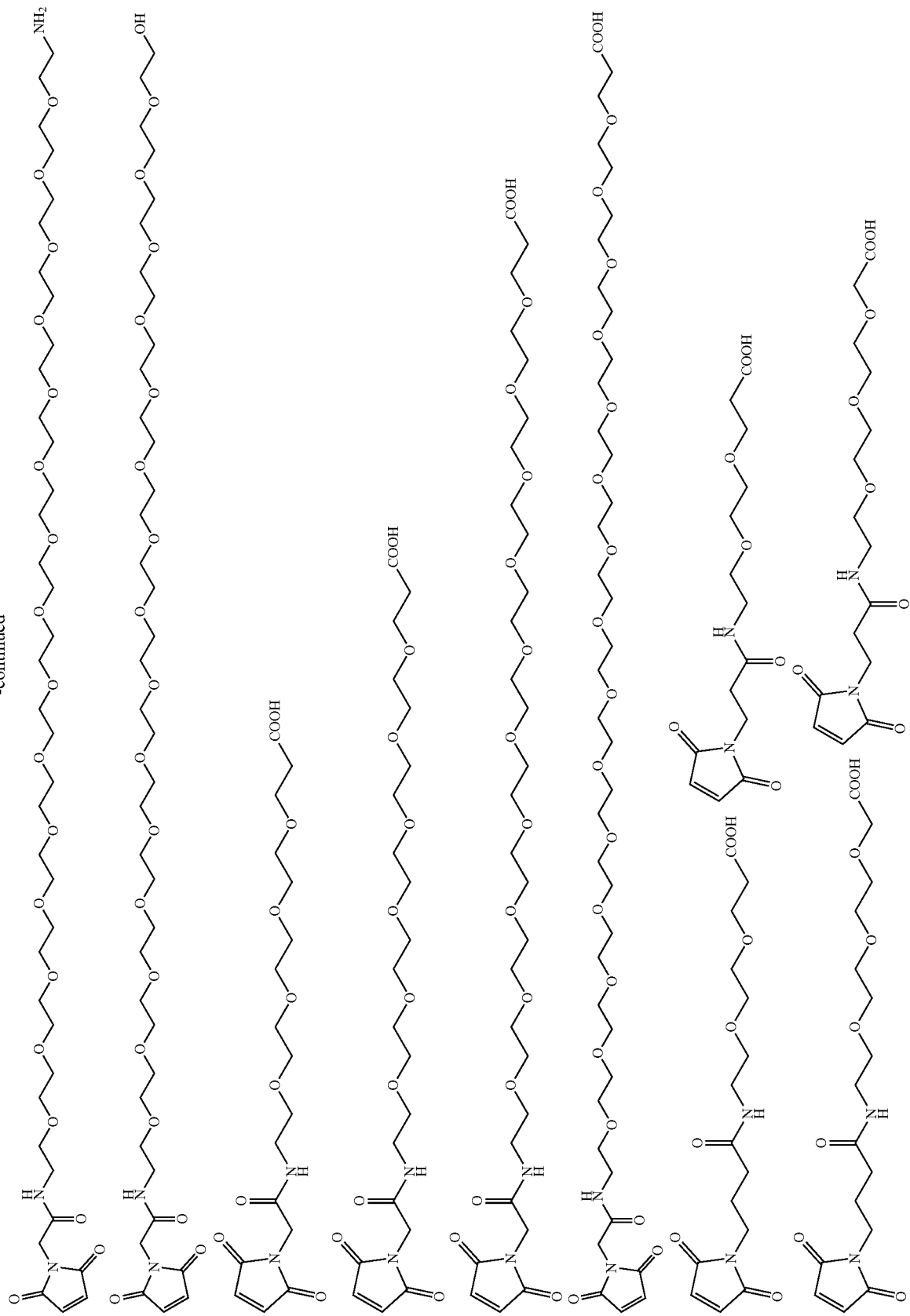

-continued
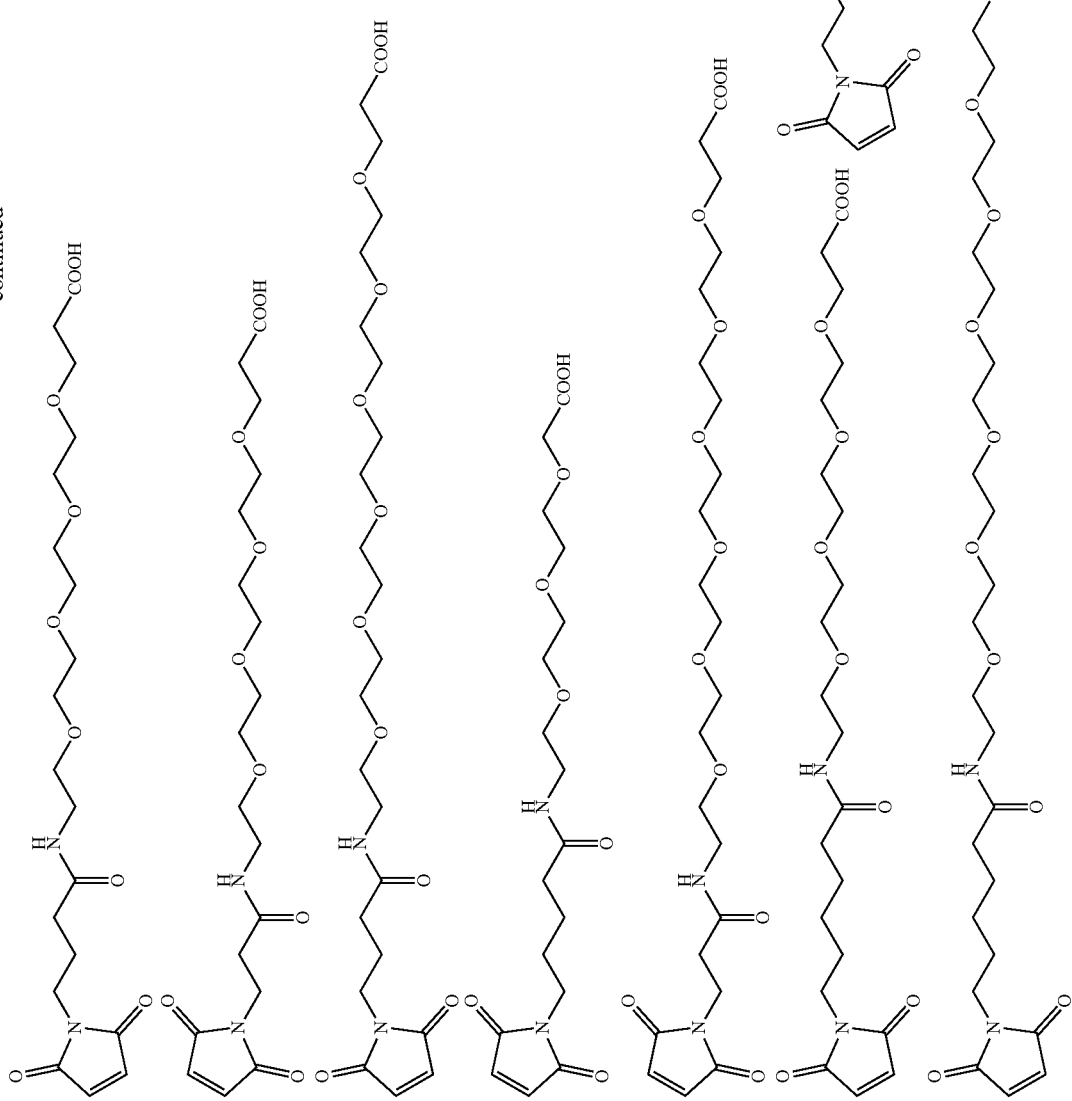

-continued
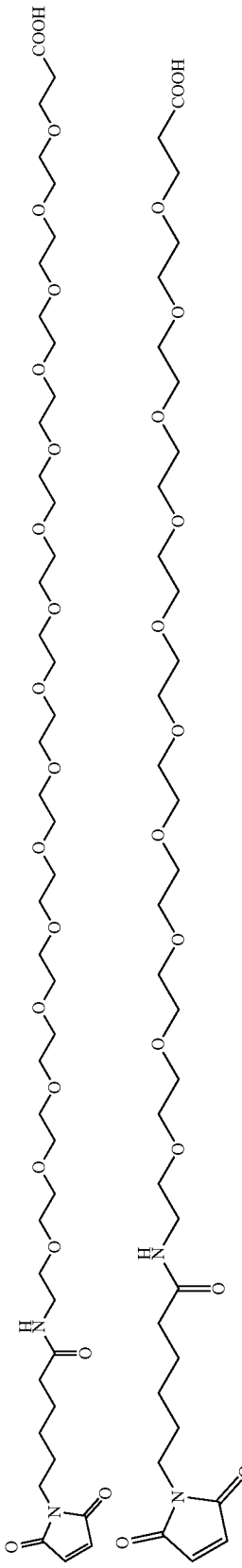
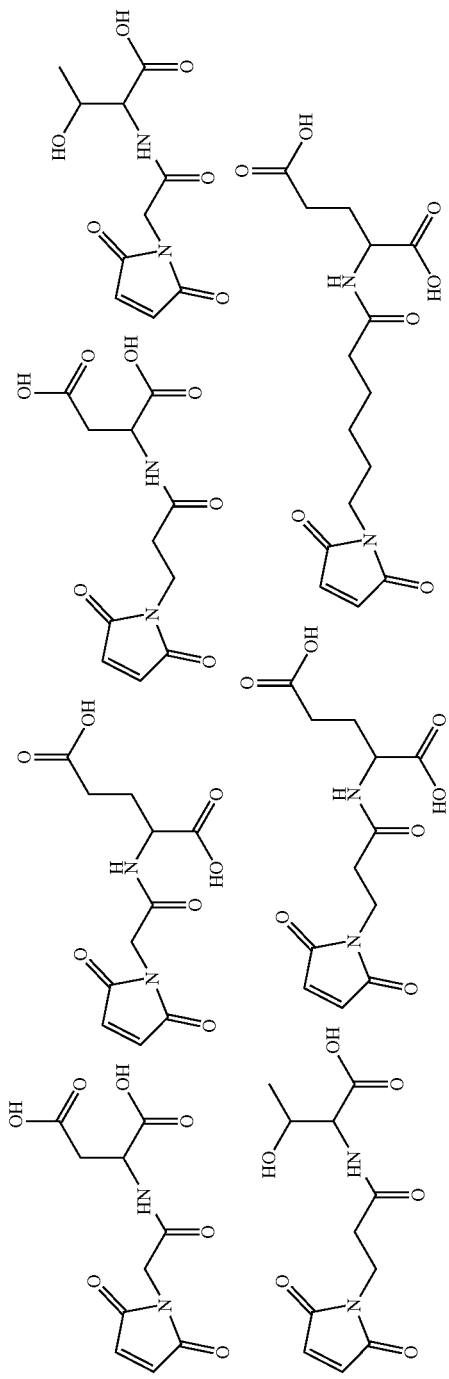
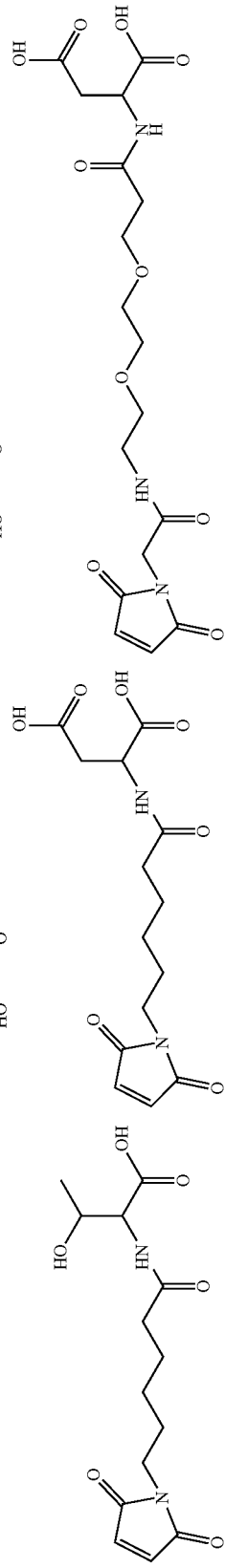

-continued
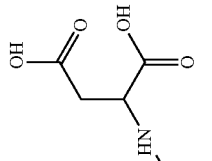
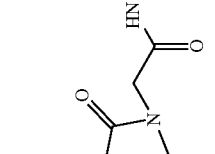
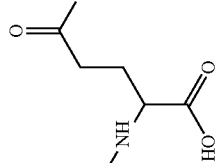
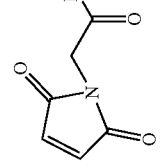
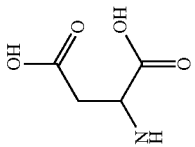
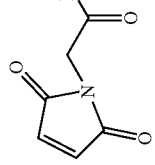
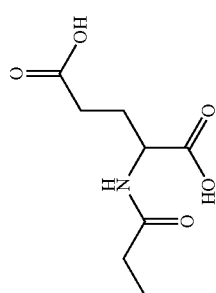
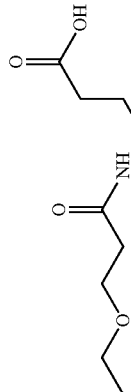
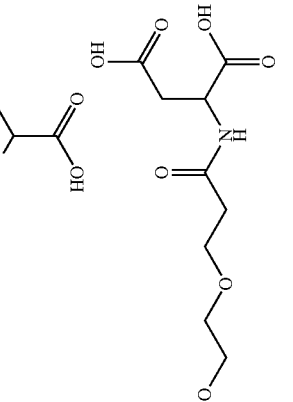
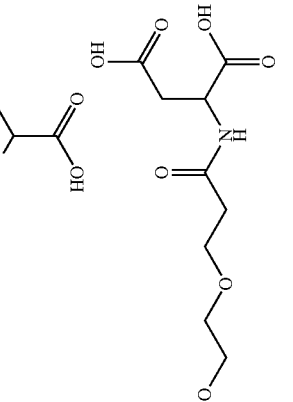
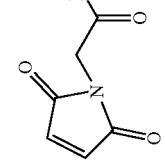
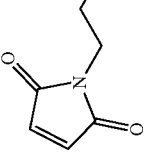

-continued
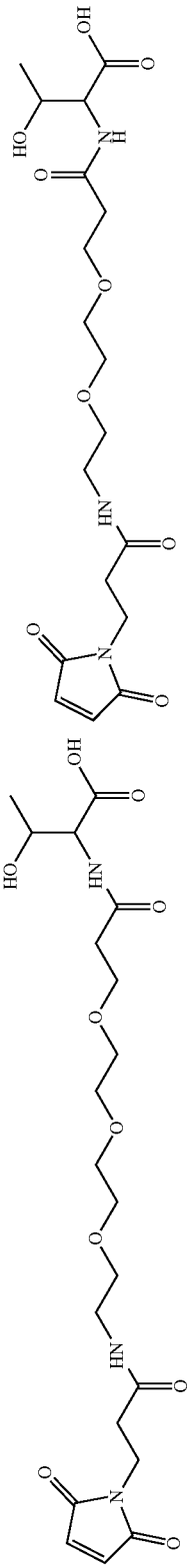 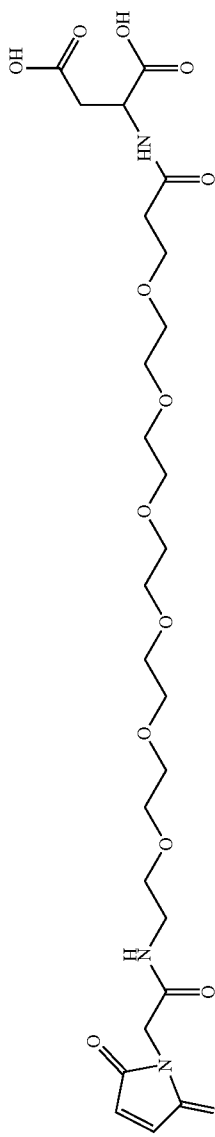 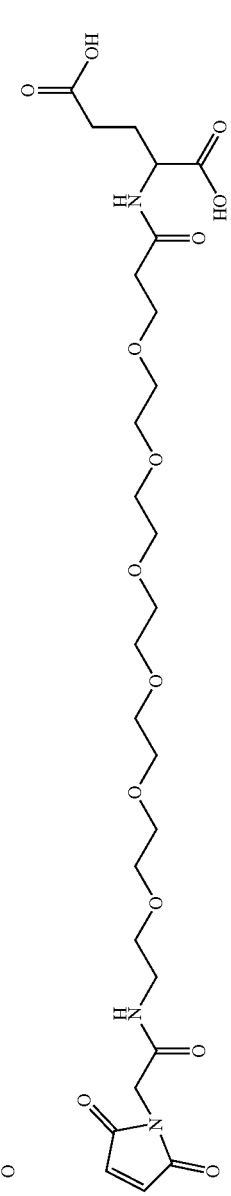 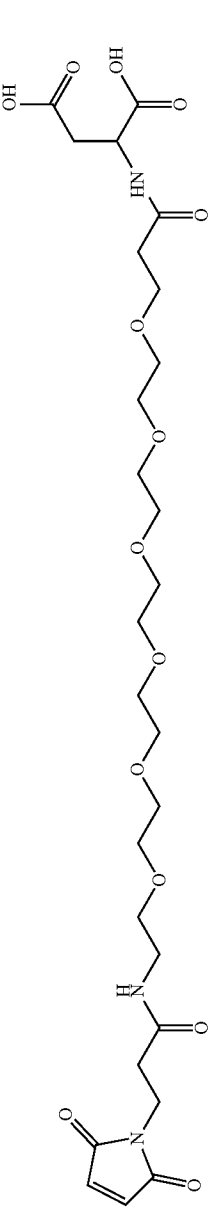 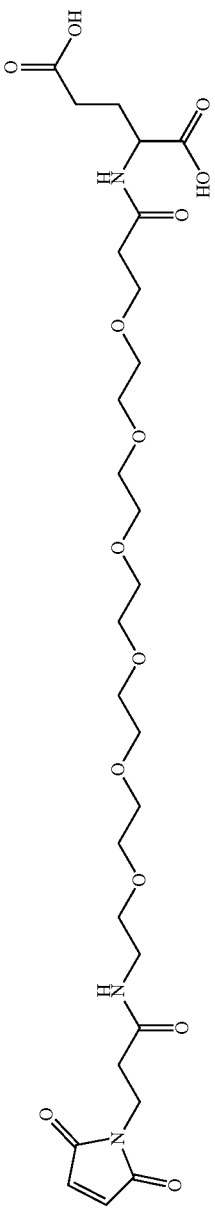

-continued
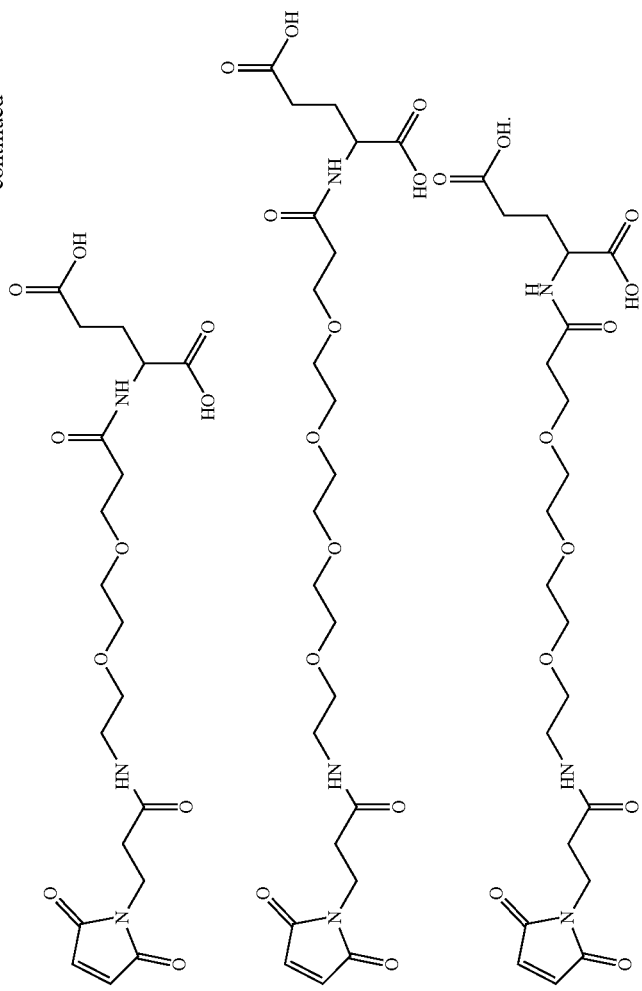

5. The compound according to claim 1, wherein A is selected from the group consisting of:

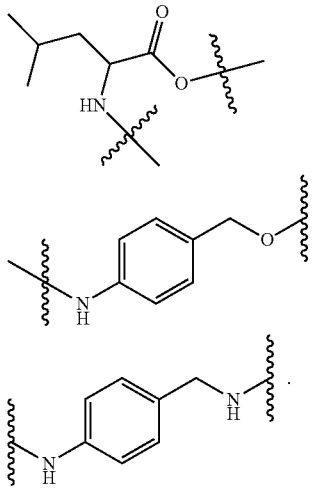

6. The compound according to claim 1, wherein MI represents a maleimide group covalently coupled to plasma albumin; C is AAN; D is a Doxorubicin, wherein the S and A is selected from the following table:

| Compound number | S1 | S2 | S3 | A |
|---|---|---|---|---|
| QHL-001 | / | 2peg | / | PABC-NH$_2$ |
| QHL-002 | / | 3peg | / | PABC-NH$_2$ |
| QHL-003 | / | 4peg | / | PABC-NH$_2$ |
| QHL-004 | / | 6peg | / | PABC-NH$_2$ |
| QHL-005 | / | 2peg | / | PABC-OH |
| QHL-006 | / | 3peg | / | PABC-OH |
| QHL-007 | / | 4peg | / | PABC-OH |
| QHL-008 | / | 6peg | / | PABC-OH |
| QHL-009 | / | 2peg | / | Leu |
| QHL-010 | / | 3peg | / | Leu |
| QHL-011 | / | 4peg | / | Leu |
| QHL-012 | / | 6peg | / | Leu |
| QHL-013 | / | 2peg | Glu | PABC-NH$_2$ |
| QHL-014 | / | 3peg | Glu | PABC-NH$_2$ |
| QHL-015 | / | 4peg | Glu | PABC-NH$_2$ |
| QHL-016 | / | 6peg | Glu | PABC-NH$_2$ |
| QHL-017 | / | 2peg | Glu | PABC-OH |
| QHL-018 | / | 3peg | Glu | PABC-OH |
| QHL-019 | / | 4peg | Glu | PABC-OH |
| QHL-020 | / | 6peg | Glu | PABC-OH |
| QHL-021 | / | 2peg | Glu | Leu |
| QHL-022 | / | 3peg | Glu | Leu |
| QHL-023 | / | 4peg | Glu | Leu |
| QHL-024 | / | 6peg | Glu | Leu |
| QHL-025 | / | 2peg | ASP | PABC-NH$_2$ |
| QHL-026 | / | 3peg | ASP | PABC-NH$_2$ |
| QHL-027 | / | 4peg | ASP | PABC-NH$_2$ |
| QHL-028 | / | 6peg | ASP | PABC-NH$_2$ |
| QHL-029 | / | 2peg | ASP | PABC-OH |
| QHL-030 | / | 3peg | ASP | PABC-OH |
| QHL-031 | / | 4peg | ASP | PABC-OH |
| QHL-032 | / | 6peg | ASP | PABC-OH |
| QHL-033 | / | 2peg | ASP | Leu |
| QHL-034 | / | 3peg | ASP | Leu |
| QHL-035 | / | 4peg | ASP | Leu |
| QHL-036 | / | 6peg | ASP | Leu |
| QHL-037 | C$_2$—COOH | 2peg | Glu | PABC-NH$_2$ |
| QHL-038 | C$_2$—COOH | 2peg | Glu | PABC-OH |
| QHL-039 | C$_2$—COOH | 2peg | Glu | Leu |
| QHL-040 | C$_2$—COOH | 2peg | ASP | PABC-NH$_2$ |
| QHL-041 | C$_2$—COOH | 2peg | ASP | PABC-OH |
| QHL-042 | C$_2$—COOH | 2peg | ASP | Leu |
| QHL-043 | C$_2$—COOH | 3peg | Glu | PABC-NH$_2$ |
| QHL-044 | C$_2$—COOH | 3peg | Glu | PABC-OH |
| QHL-045 | C$_2$—COOH | 3peg | Glu | Leu |
| QHL-046 | C$_2$—COOH | 3peg | ASP | PABC-NH$_2$ |
| QHL-047 | C$_2$—COOH | 3peg | ASP | PABC-OH |
| QHL-048 | C$_2$—COOH | 3peg | ASP | Leu |
| QHL-049 | C$_2$—COOH | 4peg | Glu | PABC-NH$_2$ |
| QHL-050 | C$_2$—COOH | 4peg | Glu | PABC-OH |
| QHL-051 | C$_2$—COOH | 4peg | Glu | Leu |
| QHL-052 | C$_2$—COOH | 4peg | ASP | PABC-NH$_2$ |
| QHL-053 | C$_2$—COOH | 4peg | ASP | PABC-OH |
| QHL-054 | C$_2$—COOH | 4peg | ASP | Leu |
| QHL-055 | C$_2$—COOH | 6peg | Glu | PABC-NH$_2$ |
| QHL-056 | C$_2$—COOH | 6peg | Glu | PABC-OH |
| QHL-057 | C$_2$—COOH | 6peg | Glu | Leu |
| QHL-058 | C$_2$—COOH | 6peg | ASP | PABC-NH$_2$ |
| QHL-059 | C$_2$—COOH | 6peg | ASP | PABC-OH |
| QHL-060 | C$_2$—COOH | 6peg | ASP | Leu |
| QHL-061 | C$_3$—COOH | 2peg | Glu | PABC-NH$_2$ |
| QHL-062 | C$_3$—COOH | 2peg | Glu | PABC-OH |
| QHL-063 | C$_3$—COOH | 2peg | Glu | Leu |
| QHL-064 | C$_3$—COOH | 2peg | ASP | PABC-NH$_2$ |
| QHL-065 | C$_3$—COOH | 2peg | ASP | PABC-OH |
| QHL-066 | C$_3$—COOH | 2peg | ASP | Leu |
| QHL-067 | C$_3$—COOH | 3peg | Glu | PABC-NH$_2$ |
| QHL-068 | C$_3$—COOH | 3peg | Glu | PABC-OH |
| QHL-069 | C$_3$—COOH | 3peg | Glu | Leu |
| QHL-070 | C$_3$—COOH | 3peg | ASP | PABC-NH$_2$ |
| QHL-071 | C$_3$—COOH | 3peg | ASP | PABC-OH |
| QHL-072 | C$_3$—COOH | 3peg | ASP | Leu |
| QHL-073 | C$_3$—COOH | 4peg | Glu | PABC-NH$_2$ |
| QHL-074 | C$_3$—COOH | 4peg | Glu | PABC-OH |
| QHL-075 | C$_3$—COOH | 4peg | Glu | Leu |
| QHL-076 | C$_3$—COOH | 4peg | ASP | PABC-NH$_2$ |
| QHL-077 | C$_3$—COOH | 4peg | ASP | PABC-OH |
| QHL-078 | C$_3$—COOH | 4peg | ASP | Leu |
| QHL-079 | C$_3$—COOH | 6peg | Glu | PABC-NH$_2$ |
| QHL-080 | C$_3$—COOH | 6peg | Glu | PABC-OH |
| QHL-081 | C$_3$—COOH | 6peg | Glu | Leu |
| QHL-082 | C$_3$—COOH | 6peg | ASP | PABC-NH$_2$ |
| QHL-083 | C$_3$—COOH | 6peg | ASP | PABC-OH |
| QHL-084 | C$_3$—COOH | 6peg | ASP | Leu |
| QHL-085 | C$_2$—COOH | 2peg | / | PABC-NH$_2$ |
| QHL-086 | C$_2$—COOH | 2peg | / | PABC-OH |
| QHL-087 | C$_2$—COOH | 2peg | / | Leu |
| QHL-088 | C$_2$—COOH | 3peg | / | PABC-NH$_2$ |
| QHL-089 | C$_2$—COOH | 3peg | / | PABC-OH |
| QHL-090 | C$_2$—COOH | 3peg | / | Leu |
| QHL-091 | C$_2$—COOH | 4peg | / | PABC-NH$_2$ |
| QHL-092 | C$_2$—COOH | 4peg | / | PABC-OH |
| QHL-093 | C$_2$—COOH | 4peg | / | Leu |
| QHL-094 | C$_2$—COOH | 6peg | / | PABC-NH$_2$ |
| QHL-095 | C$_2$—COOH | 6peg | / | PABC-OH |
| QHL-096 | C$_2$—COOH | 6peg | / | Leu |
| QHL-097 | C$_3$—COOH | 2peg | / | PABC-NH$_2$ |
| QHL-098 | C$_3$—COOH | 2peg | / | PABC-OH |
| QHL-099 | C$_3$—COOH | 2peg | / | Leu |
| QHL-100 | C$_3$—COOH | 3peg | / | PABC-NH$_2$ |
| QHL-101 | C$_3$—COOH | 3peg | / | PABC-OH |
| QHL-102 | C$_3$—COOH | 3peg | / | Leu |
| QHL-103 | C$_3$—COOH | 4peg | / | PABC-NH$_2$ |
| QHL-104 | C$_3$—COOH | 4peg | / | PABC-OH |
| QHL-105 | C$_3$—COOH | 4peg | / | Leu |
| QHL-106 | C$_3$—COOH | 6peg | / | PABC-NH$_2$ |
| QHL-107 | C$_3$—COOH | 6peg | / | PABC-OH |
| QHL-108 | C$_3$—COOH | 6peg | / | Leu |
| QHL-109 | C$_3$—COOH | / | Glu | PABC-NH$_2$ |
| QHL-110 | C$_3$—COOH | / | Glu | PABC-OH |
| QHL-111 | C$_3$—COOH | / | Glu | Leu |
| QHL-112 | C$_3$—COOH | / | ASP | PABC-NH$_2$ |
| QHL-113 | C$_3$—COOH | / | ASP | PABC-OH |
| QHL-114 | C$_3$—COOH | / | ASP | Leu |
| QHL-115 | C$_6$—COOH | / | Glu | PABC-NH$_2$ |
| QHL-116 | C$_6$—COOH | / | Glu | PABC-OH |

-continued

| Compound number | S1 | S2 | S3 | A |
|---|---|---|---|---|
| QHL-117 | C$_6$—COOH | / | Glu | Leu |
| QHL-118 | C$_6$—COOH | / | ASP | PABC-NH$_2$ |
| QHL-119 | C$_6$—COOH | / | ASP | PABC-OH |
| QHL-120 | C$_6$—COOH | / | ASP | Leu |
| QHL-121 | C$_6$—COOH | / | Gly | Leu |
| QHL-122 | C$_6$—COOH | / | Ala | Leu |
| QHL-123 | C$_6$—COOH | / | Val | Leu |
| QHL-124 | C$_6$—COOH | / | Leu | Leu |
| QHL-125 | C$_6$—COOH | / | Ile | Leu |
| QHL-126 | C$_6$—COOH | / | Met | Leu |
| QHL-127 | C$_6$—COOH | / | Phe | Leu |
| QHL-128 | C$_6$—COOH | / | Trp | Leu |
| QHL-129 | C$_6$—COOH | / | Ser | Leu |
| QHL-130 | C$_6$—COOH | / | Thr | Leu |
| QHL-131 | C$_6$—COOH | / | Cys | Leu |
| QHL-132 | C$_6$—COOH | / | Tyr | Leu |
| QHL-133 | C$_6$—COOH | / | Asn | Leu |
| QHL-134 | C$_6$—COOH | / | Gln | Leu |
| QHL-135 | C$_6$—COOH | / | Lys | Leu |
| QHL-136 | C$_6$—COOH | / | Arq | Leu |
| QHL-137 | C$_6$—COOH | / | His | Leu |

7. The compound according to claim 1, wherein the compound is selected from the group consisting of: